US007947733B2

(12) United States Patent
Robbins et al.

(10) Patent No.: US 7,947,733 B2
(45) Date of Patent: *May 24, 2011

(54) PHOSPHORYLATED PYRONE ANALOGS AND METHODS

(75) Inventors: Wendye Robbins, San Francisco, CA (US); Ving Lee, Los Altos, CA (US)

(73) Assignee: Limerick BioPharma, South San Francisco, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 12/182,992

(22) Filed: Jul. 30, 2008

(65) Prior Publication Data

US 2009/0069273 A1 Mar. 12, 2009

Related U.S. Application Data

(60) Provisional application No. 60/953,188, filed on Jul. 31, 2007, provisional application No. 61/076,608, filed on Jun. 27, 2008.

(51) Int. Cl.
*A01N 43/16* (2006.01)
*A61K 31/35* (2006.01)
*C07D 311/00* (2006.01)
(52) U.S. Cl. ...................... 514/456; 549/409
(58) Field of Classification Search .............. 514/456; 549/409
See application file for complete search history.

(56) References Cited

U.S. PATENT DOCUMENTS

| | | | |
|---|---|---|---|
| 2,764,596 A | 9/1956 | Avakian et al. | |
| 4,530,844 A | 7/1985 | Smerbeck et al. | 514/458 |
| 5,342,625 A | 8/1994 | Hauer et al. | 424/455 |
| 5,348,966 A | 9/1994 | Starzl et al. | 514/326 |
| 5,643,901 A | 7/1997 | Honbo et al. | 514/183 |
| 5,817,333 A | 10/1998 | Kagayama et al. | 424/450 |
| 5,866,159 A | 2/1999 | Hauer et al. | 424/450 |
| 5,916,589 A | 6/1999 | Hauer et al. | 424/450 |
| 5,939,427 A | 8/1999 | Kagayama et al. | 514/291 |
| 5,962,014 A | 10/1999 | Hauer et al. | 424/450 |
| 5,962,017 A | 10/1999 | Hauer et al. | 424/450 |
| 5,972,598 A | 10/1999 | Chaudhary et al. | 435/6 |
| 6,007,840 A | 12/1999 | Hauer et al. | 424/450 |
| 6,013,621 A | 1/2000 | Nishi et al. | 514/2 |
| 6,022,852 A | 2/2000 | Klokkers et al. | 514/11 |
| 6,024,978 A | 2/2000 | Hauer et al. | 424/450 |
| 6,333,334 B1 | 12/2001 | Koshika et al. | 514/291 |
| 6,362,160 B1 | 3/2002 | Dawson et al. | 514/2 |
| 6,384,073 B1 | 5/2002 | Sakuma | 514/455 |
| 6,440,458 B1 | 8/2002 | Yamashita et al. | 424/468 |
| 6,489,340 B1 | 12/2002 | Nishigaki et al. | 514/321 |
| 6,492,513 B1 | 12/2002 | Nishihara et al. | 540/456 |
| 6,576,259 B2 | 6/2003 | Yamashita et al. | 424/468 |
| 6,673,768 B1 | 1/2004 | Grant et al. | 514/11 |
| 6,673,807 B1 | 1/2004 | Sakai et al. | 514/290 |
| 6,774,142 B2 | 8/2004 | Lathey et al. | |
| 6,833,353 B1 | 12/2004 | Yamamoto et al. | 514/9 |
| 6,864,232 B1 | 3/2005 | Ueno | 514/9 |
| 6,884,433 B2 | 4/2005 | Yamashita et al. | 424/468 |
| 6,916,785 B2 | 7/2005 | Patel | 514/11 |
| 6,965,039 B2 | 11/2005 | Gesson et al. | |
| 6,984,397 B2 | 1/2006 | Fujisaki et al. | 424/450 |
| 7,531,646 B2 | 5/2009 | Burton | |
| 2002/0106338 A1 | 8/2002 | Pfluecker et al. | |
| 2003/0036560 A1 | 2/2003 | Sonis et al. | 514/420 |
| 2003/0166584 A1 | 9/2003 | Hu et al. | 514/27 |
| 2004/0048789 A1 | 3/2004 | Patel | 514/11 |
| 2004/0053860 A1 | 3/2004 | Buchholz et al. | 514/27 |
| 2004/0059136 A1 | 3/2004 | Gesson et al. | |
| 2004/0091477 A1 | 5/2004 | Haines et al. | |
| 2004/0102386 A1 | 5/2004 | Lahey et al. | |
| 2004/0209825 A1 | 10/2004 | Lahey et al. | |
| 2004/0209850 A1 | 10/2004 | Babul | 514/165 |
| 2004/0235081 A1 | 11/2004 | Burton et al. | |
| 2005/0008640 A1 | 1/2005 | Waegell et al. | 424/145.1 |
| 2005/0020614 A1 | 1/2005 | Prescott et al. | 514/291 |
| 2005/0080021 A1 | 4/2005 | Tucker et al. | |
| 2005/0080024 A1 | 4/2005 | Tucker et al. | |
| 2005/0107291 A1 | 5/2005 | Hunter et al. | 514/11 |
| 2006/0014677 A1 | 1/2006 | Mayo | 514/11 |
| 2006/0030542 A1 | 2/2006 | Frey et al. | |
| 2006/0069042 A1 | 3/2006 | Hu et al. | |
| 2006/0100179 A1 | 5/2006 | Pero et al. | 514/130 |

(Continued)

FOREIGN PATENT DOCUMENTS

CN 1666987 A 9/2005

(Continued)

OTHER PUBLICATIONS

Dorwald, F. ed. Side reactions in organic synthesis: a guide to successful synthesis design. Weinheim: Wiley-VCH Verlag GmbH & Co. KGaA, 2005. Preface.
International search report dated Oct. 16, 2008 for PCT Application No. US2008/71606.
International search report dated Nov. 6, 2008 for PCT Application No. US2008/71557.
Jordan, V. Tamoxifen: a most unlikely pioneering medicine. Nat Rev Drug Discov. Mar. 2003;2(3):205-13.
Beutler, et al. Structure-activity requirements for flavone cytotoxicity and binding to tubulin. J Med Chem. Jun. 18, 1998;41(13):2333-8.
Ellemose, et al. Synthesis of 3-Acyl- and 3-Carbamoylflavones. Acta Chemica Scandinavica. 1995; 49(7), 524-9.

(Continued)

*Primary Examiner* — Sreeni Padmanabhan
*Assistant Examiner* — Sarah Pihonak
(74) *Attorney, Agent, or Firm* — Seed IP Law Group PLLC

(57) ABSTRACT

The invention relates to phosphorylated polyphenols, phosphorylated flavonoids, and phosphorylated pyrone analogs. Methods and compositions for the modulation of side effects of substances using such phosphorylated compounds are described. Methods and compositions are described for the modulation of blood-tissue barrier (BTB) transporter activity to increase the efflux of drugs and other compounds out of a physiological compartment and into an external environment. In particular, the methods and compositions disclosed herein provide lowered side effects when phosphorylated pyrone analogs are coadministered with therapeutic agents.

44 Claims, 2 Drawing Sheets

U.S. PATENT DOCUMENTS

| | | |
|---|---|---|
| 2006/0111307 A1 | 5/2006 | Robbins |
| 2006/0111308 A1 | 5/2006 | Robbins |
| 2006/0124903 A1 | 6/2006 | Ito et al. .................... 252/372 |
| 2006/0205767 A1 | 9/2006 | Wong et al. |
| 2007/0087977 A1 | 4/2007 | Robbins |
| 2007/0099826 A1 | 5/2007 | Wong et al. |
| 2007/0161605 A1 | 7/2007 | Cheng et al. |
| 2008/0095866 A1 | 4/2008 | Declercq et al. |
| 2008/0153819 A1 | 6/2008 | Bingaman et al. ......... 514/233.8 |
| 2008/0161248 A1 | 7/2008 | Robbins ...................... 514/27 |
| 2009/0029987 A1 | 1/2009 | Wong et al. ............. 514/233.8 |
| 2009/0069273 A1 | 3/2009 | Robbins et al. ............ 514/100 |
| 2009/0076053 A1 | 3/2009 | Robbins ..................... 514/282 |
| 2009/0082400 A1 | 3/2009 | Lee et al. ................... 514/326 |
| 2009/0088394 A1 | 4/2009 | Robbins ...................... 514/27 |
| 2009/0130051 A1 | 5/2009 | Jarrott et al. |
| 2009/0258939 A1 | 10/2009 | Robbins |
| 2009/0325906 A1 | 12/2009 | Robbins et al. ............ 514/100 |
| 2010/0144612 A1 | 6/2010 | Robbins et al. ............. 514/11 |
| 2010/0189653 A1 | 7/2010 | Robbins et al. ............ 424/9.2 |
| 2010/0297020 A1 | 11/2010 | Lee et al. .................... 424/9.2 |

FOREIGN PATENT DOCUMENTS

| | | |
|---|---|---|
| EP | 0543555 A1 | 5/1993 |
| EP | 1 036 562 A1 | 9/2000 |
| EP | 1393733 A1 | 3/2004 |
| EP | 1 183 261 B1 | 9/2004 |
| EP | 1 093 371 B1 | 5/2005 |
| EP | 1438423 B1 | 12/2007 |
| FR | 837.588 | 6/1961 |
| JP | 1153695 | 6/1989 |
| JP | 01308476 | 12/1989 |
| JP | 1308476 | 12/1989 |
| JP | 7002826 | 1/1995 |
| WO | WO 93/09786 A1 | 5/1993 |
| WO | WO 96/21440 A1 | 7/1996 |
| WO | WO 00/23102 A1 | 4/2000 |
| WO | WO 00/44757 A1 | 8/2000 |
| WO | WO 01/49285 * | 7/2001 |
| WO | WO 03/022994 A2 | 3/2003 |
| WO | WO 03/035900 A1 | 5/2003 |
| WO | WO 03/022994 A3 | 10/2003 |
| WO | WO 2005/032559 A1 | 4/2005 |
| WO | WO 2005/034960 A1 | 4/2005 |
| WO | WO 2005/068484 A1 | 7/2005 |
| WO | WO 2006/008092 A1 | 1/2006 |
| WO | WO 2006/055672 A2 | 5/2006 |
| WO | WO 2006/094357 A1 | 9/2006 |
| WO | WO 2006/119406 A2 | 11/2006 |
| WO | WO 2007/016525 A2 | 2/2007 |
| WO | WO 2007/016525 A3 | 5/2007 |
| WO | WO 2007/084857 A2 | 7/2007 |
| WO | WO 2007/084857 A3 | 7/2007 |
| WO | WO 2007/124252 A2 | 11/2007 |
| WO | WO 2007/124252 A3 | 3/2008 |
| WO | WO 2008/032105 A2 | 3/2008 |
| WO | WO 2008/070346 A2 | 6/2008 |
| WO | WO 2006/119406 A3 | 7/2008 |
| WO | WO 2008/083160 A2 | 7/2008 |
| WO | WO 2008/032105 A3 | 10/2008 |
| WO | WO 2009/018320 A1 | 2/2009 |
| WO | WO 2009/018326 A2 | 2/2009 |
| WO | WO 2009/018338 A2 | 2/2009 |
| WO | WO 2009/018350 A1 | 2/2009 |
| WO | WO 2009/158007 A2 | 12/2009 |
| WO | WO 2009/158031 A2 | 12/2009 |
| WO | WO 2010/042886 A2 | 4/2010 |
| WO | WO 2010/129138 A2 | 11/2010 |

OTHER PUBLICATIONS

Hu, et al. Anti-AIDS agents, 10. Acacetin-7-O-beta-D-galactopyranoside, an anti-HIV principle from *Chrysanthemum morifolium* and a structure-activity correlation with some related flavonoids. J Nat Prod. Jan. 1994;57(1):42-51.

Katsuyama, et al. Synthesis of unnatural flavonoids and stilbenes by exploiting the plant biosynthetic pathway in *Escherichia coli*. Chem Biol. Jun. 2007;14(6):613-21.

Krishnamachari, et al. In vitro flavon-3-ol oxidation mediated by a B ring hydroxylation pattern. Chem Res Toxicol. Jun. 2004;17(6):795-804.

Lee, et al. U.S. Appl. No. 61/076,612, entitled "Soluble pyrone analogs methods and compositions," filed Jun. 27, 2008.

Robbins, et al. U.S. Appl. No. 61/076,578, entitled "Methods and compositions for therapeutic treatment," filed Jun. 27, 2008.

Robbins, et al. U.S. Appl. No. 61/076,587, entitled "Methods and compositions for therapeutic treatment," filed Jun. 27, 2008.

Robbins, et al. U.S. Appl. No. 61/076,591, entitled "Methods and compositions for therapeutic treatment," filed Jun. 27, 2008.

Robbins, et al. U.S. Appl. No. 61/076,608, entitled "Phosphorylated pyrone analogs an dmethods," filed Jun. 27, 2008.

Calias, et al. Synthesis of inositol 2-phosphate-quercetin conjugates. Carbohydr Res. Oct. 4, 1996;292:83-90.

Boucher, et al. Phenytoin prodrug 3-phosphoryloxymethyl phenytoin (ACC-9653): pharmacokinetics in patients following intravenous and intramuscular administration. J Pharm Sci. Nov. 1989;78(11):929-32.

Chemical Database: 4H-1-Benzopyran-4-one, 2-(3,4-dihydroxyphenyl)-3,5,7-trihydroxy-, phosphate, potassium salt. Http://envirpnmentalchemistry.org Accessed on Feb. 28, 2007.

Corbett, et al. Fosamprenavir. Vertex Pharmaceuticals/GlaxoSmithKline. Curr Opin Investig Drugs. Mar. 2002;3(3):384-90.

Duan, et al. Effects of Potassium quercetin phosphate on cerebral reperfusion injury. Shanxi Medical University. 1997; 28(2): 90-92. (English abstract only).

Falcoz, et al. Pharmacokinetics of GW433908, a prodrug of amprenavir, in healthy male volunteers. J Clin Pharmacol. Aug. 2002;42(8):887-98.

Feng, et al. The Protection of PP against acute cerebral ischemia-reperfusion injuries in rats. Zhongguo Yaolixue Tongbao. 1994; 10(3): 204-206. (in English abstract only).

Gatell, J. M. From amprenavir to GW433908. J HIV Ther. Nov. 2001;6(4):95-9.

Jamerson, et al. Absolute bioavailability of phenytoin after 3-phosphoryloxymethyl phenytoin disodium (ACC-9653) administration to humans. Epilepsia. Sep.-Oct. 1990;31(5):592-7.

Lu, et al. Protection of potassium quercetin phosphate combined with chlorpromazine on cerebral ischemia-reperfusion injury in rats. Shanxi Medical University. 1999; 30(3): 203-205. (in Chinese with English translation).

Murdock, et al. N-phosphoryl derivatives of bisantrene. Antitumor prodrugs with enhanced solubility and reduced potential for toxicity. J Med Chem. Jul. 23, 1993;36(15):2098-101.

Quercetin Dihydrate. Http://www.chemicalland21.com/lifescience/foco/QUERCETIN.htm. Accessed on Feb. 28, 2007.

Tang, et al. Effect of Potassium quercetin phosphate (PQP) on coronary blood flowand myocardial oxygen consumption. Zhongguo Yaoxue Zazhi. 1992; 27(12): 722-724. (in English abstract).

Allen et al., "The Mouse *Bcrp1/Mxr/Abcp* Gene: Amplification and Overexpression in Cell Lines Selected for Resistance to Topotecan, Mitoxantrone, or Doxorubicin," *Cancer Research* 59:4237-4241, Sep. 1, 1999.

Allikmets et al., "A Human Placenta-specific ATP-Binding Cassette Gene (*ABCP*) on Chromosome 4q22 That Is Involved in Multidrug Resistance," *Cancer Research* 58:5337-5339, Dec. 1, 1998.

Arts et al., "The type of sugar moiety is a major determinant of the small intestinal uptake and subsequent biliary excretion of dietary quercetin glycosides," *British Journal of Nutrition* 91:841-847, 2004.

Balczon et al., "The Identification, Purification, and Characterization of a Pancreatic β-Cell Form of the Microtubule Adenosine Triphosphatase Kinesin," *Endocrinology* 131(1):331-336, 1992.

Balkovetz et al., "A Proton Gradient Is the Driving Force for Uphill Transport of Lactate in Human Placental Brush-Border Membrane Vesicles," *The Journal of Biological Chemistry*, 263(27):13823-13830, Sep. 25, 1988.

Bissonnette, "Placental Transport of Carbohydrates," Mead Johnson Symposium on Perinatal and Developmental Medicine No. 18, Vail, Colorado May 31-Jun. 4, 1981, pp. 21-23 (4 pages total).

Borst et al., "A Family of Drug Transporters: the Multidrug Resistance-Associated Proteins," *Journal of the National Cancer Institute* 92(16):1295-1302, Aug. 16, 2000.

Boyer et al., "In vitro digestion and lactase treatment influence uptake of quercetin and quercetin glucoside by the Caco-2 cell monolayer," *Nutrition Journal* 4(1), Jan. 11, 2005 (15 pages).

Cermak et al., "The Bioavailability of Quercetin in Pigs Depends on the Glycoside Moiety and on Dietary Factors," *J. Nutr.* 133:2802-2807, 2003.

Chaudhary et al., "Expression and Activity of the Multidrug Resistance P-Glycoprotein in Human Peripheral Blood Lymphocytes," *Blood* 80(11):2735-2739, Dec. 1, 1992.

Choi et al., "Effect of quercetin on the pharmacokinetics of oral cyclosporine," *Am J Health-Syst Pharm* 61(22):2406-2409, Nov. 15, 2004.

Cordon-Cardo et al., "Expression of the Multidrug Resistance Gene Product (*P*-Glycoprotein) in Human Normal and Tumor Tissues," *J Histochem Cytochem* 38(9):1277-1287, 1990.

Critchfield et al., "Modulation of Adriamycin® Accumulation and Efflux by Flavonoids in HCT-15 Colon Cells," *Biochemical Pharmacology* 48(7):1437-1445, 1994.

Cui et al., "Drug Resistance and ATP-Dependent Conjugate Transport Mediated by the Apical Multidrug Resistance Protein, MRP2, Permanently Expressed in Human and Canine Cells," *Molecular Pharmacology* 55:929-937, 1999.

Drachenberg et al., "Islet Cell Damage Associated With Tacrolimus and Cyclosporine: Morphological Features in Pancreas Allograft Biopsies and Clinical Correlation," *Transplantation* 68(3):396-402, Aug. 15, 1999.

Dumont, "FK506, An Immunosuppressant Targeting Calcineurin Function," *Current Medicinal Chemistry* 7(7):731-748, 2000.

Fant et al., "Evidence for Carrier-Mediated Transport of Glucocorticoids by Human Placental Membrane Vesicles," *Biochimica et Biophysica Acta* 731:415-420, 1983.

Flens et al., "Tissue Distribution of the Multidrug Resistance Protein," *Am J Pathol* 148(4):1237-1247, Apr. 1996.

Folkart et al., "Transfer of carbohydrates across guinea pig placenta," *Am. J. Obst. & Gynec.* 80(2):221-223, Aug. 1960.

Ganapathy et al., "Sodium-gradient-driven, high-affinity, uphill transport of succinate in human placental brush-border membrane vesicles," *Biochem. J.* 249:179-184, 1988.

Ganapathy et al., "Placental Transporters Relevant to Drug Distribution across the Maternal-Fetal Interface," *The Journal of Pharmacology and Experimental Therapeutics* 294(2):413-420, 2000.

Graefe et al., "Pharmacokinetics and Bioavailability of Quercetin Glycosides in Humans," *J Clin Pharmacol* 41:492-499, 2001.

Hahn et al., "Ontogeny of glucose transport systems in the placenta and its progenitor tissues," *Early Pregnancy: Biology and Medicine* 2:168-182, 1996.

Haines et al., "Cardioprotective Effects of the Calcineurin Inhibitor FK506 and the PAF Receptor Antagonist and Free Radical Scavenger, EGb 761, in Isolated Ischemic/Reperfused Rat Hearts," *Journal of Cardiovascular Pharmacology* 35(1):37-44, Jan. 2000.

Henderson et al., "Ganciclovir Transfer by Human Placenta and Its Effects on Rat Fetal Cells," *Am J Med Sci* 306(3):151-156, Sep. 1993.

Hipfner et al., "Structural, mechanistic and clinical aspects of MRP1," *Biochimica et Biophysica Acta* 1461:359-376, 1999.

Hirano et al., "Morphological and Functional Changes of Islets of Langerhans in FK506-Treated Rats," *Transplantation* 53(4):889-894, Apr. 1992.

Hisamura et al., "Protective Effect of Green Tea Extract and Tea Polyphenols against FK506-Induced Cytotoxicity in Renal Cells," *Basic & Clinical Pharmacology & Toxicology* 98(2):192-196, Feb. 2006.

Hollman et al., "Absorption of dietary quercetin glycosides and quercetin in healthy ileostomy volunteers," *Am J Clin Nutr* 62l276-82, 1995.

Jonker et al., "Role of Breast Cancer Resistance Protein in the Bioavailability and Fetal Penetration of Topotecan," *J Natl Cancer Inst* 92(20):1651-6, Oct. 18, 2000.

Kekuda et al., "Cloning and Functional Characterization of a Potential-sensitive, Polyspecific Organic Cation Transporter (OCT3) Most Abundantly Expressed in Placenta," *The Journal of Biological Chemistry* 273(26):15971-15979, Jun. 26, 1998.

Kochi et al., "Effect of cyclosporin A or tacrolimus on the function of blood-brain barrier cells," *European Journal of Pharmacology* 372:287-295, 1999.

Kondratov et al., "Small molecules that dramatically alter multidrug resistance phenotype by modulating the substrate specificity of *P*-glycoprotein," *PNAS* 98(24):14078-14083, Nov. 20, 2001.

Krogsgaard-Larsen, "A Textbook of Drug Design and Development," Harwood Academic Publishers, Switzerland, 1991, p. 148 (9 pages total).

Kudo et al., "Carrier-mediated transport system for cephalexin in human placental brush-border membrane vesicles," *Biochimica et Biophysica Acta* 978:313-318, 1989.

Lankas et al., "Placental P-Glycoprotein Deficiency Enhances Susceptibility to Chemically Induced Birth Defects in Mice," *Reproductive Toxicology* 12(4):457-463, 1998.

Lawrence et al., "Regulation of Insulin Gene Transcription by a $Ca^{2+}$-Responsive Pathway Involving Calcineurin and Nuclear Factor of Activated T Cells," *Molecular Endocrinology* 15(10):1758-1767, Oct. 2001.

Meng et al., "Suppression of the Expression of a Pancreatic β-Cell Form of the Kinesin Heavy Chain by Antisense Oligonucleotides Inhibits Insulin Secretion from Primary Cultures of Mouse β-Cells," *Endocrinology* 138(5):1979-1987, 1997.

Moe, "Placental amino acid transport," *Am. J. Physiol* 268(*Cell Physiol.* 37):C1321-C1331, 1995.

Moon et al., "Identification of Quercetin 3-*O*-β-D-Glucuronide as an Antioxidative Metabolite in Rat Plasma After Oral Administration of Quercetin," *Free Radical Biology & Medicine* 30(11):1274-1285, 2001.

Nakamura et al., "Proton Gradient-Dependent Transport of Valproic Acid in Human Placental Brush-Border Membrane Vesicles," *Pharmaceutical Research* 19(2):154-161, Feb. 2002.

Noguchi et al., "Cyclic ADP-ribose Binds to FK506-binding Protein 12.6 to Release $Ca^{2+}$ from Islet Microsomes," *The Journal of Biological Chemistry* 272(6):3133-3136, Feb. 7, 1997.

Ohashi et al., "$Na^+$-Dependent Carnitine Transport by Organic Cation Transporter (OCTN2): Its Pharmacological and Toxicological Relevance," *The Journal of Pharmacology and Experimental Therapeutics* 291(2):778-784, 1999.

Okamoto et al., "The CD38-cyclic ADP-ribose signalling system in insulin secretion: molecular basis and clinical implications," *Diabetologia* 40:1485-1491, 1997.

Pacifici et al., "Placental Transfer of Drugs Administered to the Mother," *Clin. Pharmacokinet.* 28(3):235-269, 1995.

Pávek et al., "Influence of P-Glycoprotein on the Transplacental Passage of Cyclosporine," *Journal of Pharmaceutical Sciences* 90(10):1583-1592, Oct. 2001.

Polli et al., "P-glycoprotein Influences the Brain Concentrations of Cetirizine (Zyrtec®), a Second-Generation Non-Sedating Antihistamine," *Journal of Pharmaceutical Sciences* 92(10):2082-2089, Oct. 2003.

Price et al., "Cloning and sequencing of four new mammalian monocarboxylate transporter (MCT) homologues confirms the existence of a transporter family with an ancient past," *Biochem. J.* 329:321-328, 1998.

Radu et al., "Tacrolimus suppresses glucose-induced insulin release from pancreatic islets by reducing glucokinase activity," *Am J Physiol Endocrinol Metab* 288:E365-E371, Feb. 2005.

Ramamoorthy et al., "Partial Purification and Characterization of the Human Placental Serotonin Transporter," *Placenta* 14:449-461, 1993.

Ramamoorthy et al., "Expression of a Cocaine-Sensitive Norepinephrine Transporter in the Human Placental Syncytiotrophoblast," *Biochemistry* 32(5):1346-1353, 1993.

Sakakura et al., "Selective Synthesis of Phosphate Monoesters by Dehydrative Condensation of Phosphoric Acid and Alcohols Promoted by Nucleophilic Bases," *Org. Lett.* 7(10):1999-2002, 2005.

Schinkel et al., "P-Glycoprotein in the Blood-Brain Barrier of Mice Influences the Brain Penetration and Pharmacological Activity of Many Drugs," *J. Clin. Invest.* 97(11):2517-2524, Jun. 1996.

Shoskes et al., "Beneficial Effects of the Bioflavonoids Curcumin and Quercetin on Early Function in Cadaveric Renal Transplantation: A Randomized Placebo Controlled Trial," *Transplantation* 80(11):1556-1559, Dec. 15, 2005.

Smit et al., "Absence or pharmacological blocking of placental P-glycoprotein profoundly increases fetal drug exposure," *J. Clin. Invest.* 104(10):1441-1447, Nov. 1999.

St-Pierre et al., "Expression of members of the multidrug resistance protein family in human term placenta," *Am J Physiol Regulatory Integrative Comp Physiol 279*:R1495-R1503, 2000.

Sugawara et al., "Lung resistance protein (LRP) expression in human normal tissues in comparison with that of MDR1 and MRP," *Cancer Letters 112*:23-31, 1997.

Sugawara et al., "Tissue Distribution of P-Glycoprotein Encoded by a Multidrug-resistant Gene as Revealed by a Monoclonal Antibody, MRK 16," *Cancer Research 48*:1926-1929, Apr. 1, 1988.

Syme et al., "Drug Transfer and Metabolism by the Human Placenta," *Clin Pharmacokinet 43*(8):487-514, 2004.

Takasawa et al., "Cyclic ADP-Ribose in Insulin Secretion from Pancreatic β Cells," *Science 259*:370-373, Jan. 15, 1993.

Uchizono et al., "Tacrolimus Impairment of Insulin Secretion in Isolated Rat Islets Occurs at Multiple Distal Sites in Stimulus-Secretion Coupling," *Endocrinology 145*(5):2264-2272, 2004.

Ushigome et al., "Human placental transport of vinblastine, vincristine, digoxin and progesterone: contribution of P-glycoprotein," *European Journal of Pharmacology 408*:1-10, 2000.

Wang et al., "Elevation of P-glycoprotein function by a catechin in green tea," *Biochemical and Biophysical Research Communications 297*:412-418, 2002.

Wang et al., "Determination of P-glycoprotein Inhibition by Excipients and Their Combinations Using an Integrated High-Throughput Process," *Journal of Pharmaceutical Sciences 93*(11):2755-2767, Nov. 2004.

Wu et al., "Structural and functional characteristics and tissue distribution pattern of rat OCTN1, an organic cation transporter, cloned from placenta," *Biochimica et Biophysica Acta 1466*:315-317, 2000.

Wu et al., "cDNA Sequence, Transport Function, and Genomic Organization of Human OCTN2, A New Member of the Organic Cation Transporter Family," *Biochemical and Biophysical Research Communications 246*(3):589-595, 1998.

Wu et al., "Functional Characteristics and Tissue Distribution Pattern of Organic Cation Transporter 2 (OCTN2), an Organic Cation/Carnitine Transporter," *The Journal of Pharmacology and Experimental Therapeutics 290*(3):1482-1492, 1999.

Yamauchi et al., "Neurotoxicity Induced by Tacrolimus After Liver Transplantation: Relation to Genetic Polymorphisms of the *ABCB1* (MDR1) Gene," *Transplantation 74*(4):571-573, Aug. 27, 2002.

Yokogawa et al., "P-Glycoprotein-Dependent Disposition Kinetics of Tacrolimus: Studies in *mdr*1a Knockout Mice," *Pharmaceutical Research 16*(8):1213-1218, 1999.

Zheng et al., "Physiochemical and Structural Characterization of Quercetin-β-Cyclodextrin Complexes," *Journal of Pharmaceutical Sciences 94*(5):1079-1089, May 2005.

Wendye Robbins, "Methods and Compositions for Therapeutic Treatment," U.S. Appl. No. 60/882,306, filed Dec. 28, 2006, 63 pages.

Wendye Robbins, "Methods and Compositions for Therapeutic Treatment," U.S. Appl. No. 60/940,375, filed May 25, 2007, 79 pages.

Ving Lee et al., "Soluble Flavonoid Methods and Pharmaceutical Compositions," U.S. Appl. No. 60/953,186, filed Jul. 31, 2007, 127 pages.

Wendye Robbins et al., "Polyhydroxylated Aromatic Compositions and Methods," U.S. Appl. No. 60/953,187, filed Jul. 31, 2007, 158 pages.

Wendye Robbins et al., "Flavonoid Phosphate Compositions and Methods," U.S. Appl. No. 60/953,188, filed Jul. 31, 2007, 110 pages.

Wendye Robbins, "Methods and Compositions for Therapeutic Treatment," U.S. Appl. No. 60/953,192, filed Jul. 31, 2007, 94 pages.

Wendye Robbins et al., "Pyrone Analog Compositions and Methods," U.S. Appl. No. 61/076,584, filed Jun. 27, 2008, 250 pages.

International Search Report, mailed Sep. 10, 2008, for PCT/US2007/088827, 2 pages.

Written Opinion, mailed Sep. 10, 2008, for PCT/US07/88827, 5 pages.

Written Opinion, mailed Oct. 16, 2008, for PCT/US08/71606, 9 pages.

Written Opinion, mailed Nov. 6, 2008, for PCT/US08/71557, 5 pages.

International Preliminary Report on Patentability, dated Jun. 30, 2009, for PCT/US2007/088827, 6 pages.

Wendye Robbins et al., "Pyrone Analogs Useful for Reducing Side Effects of Therapeutic Agents (as amended)," Office Action mailed Sep. 3, 2009, for U.S. Appl. No. 12/182,323, 29 pages.

International Preliminary Report on Patentability, dated Feb. 2, 2010, for PCT/US2008/071557, 6 pages.

International Preliminary Report on Patentability, dated Feb. 2, 2010, for PCT/US2008/071606, 10 pages.

Wendye Robbins et al., "Pyrone Analogs Useful for Reducing Side Effects of Therapeutic Agents (as amended)," Office Action mailed Mar. 10, 2010, for U.S. Appl. No. 12/182,323, 14 pages.

International Search Report, mailed Mar. 11, 2010, for PCT/US2009/003833, 4 pages.

Written Opinion, mailed Mar. 11, 2010, for PCT/US2009/003833, 4 pages.

Wendye Robbins et al., "Phosphorylated Pyrone Analogs and Methods," Combined Search and Examination Report under Sections 17 and 18(3) mailed Mar. 19, 2010 for GB Application No. GB1002044.4, 6 pages.

Wendye Robbins et al., "Phosphorylated Pyrone Analogs and Methods," U.S. Appl. No. 12/765,580, filed Apr. 22, 2010, 124 pages.

International Preliminary Report On Patentability for International Application No. PCT/US2008/071588, mailed Oct. 5, 2010, 12 pages.

International Search Report and Written Opinion for International Application No. PCT/US2008/071588, mailed Sep. 17, 2010, 15 pages.

\* cited by examiner

PHOSPHORYLATED PYRONE ANALOGS AND METHODS

CROSS-REFERENCE

This application claims the benefit of U.S. Provisional Application No. 60/953,188, filed Jul. 31, 2007; and U.S. Provisional Application No. 61/076,608, filed Jun. 27, 2008; which are incorporated herein by reference in their entirety.

BACKGROUND OF THE INVENTION

Polyphenols such as flavonoids have been shown to have beneficial health effects. In particular, polyphenols can provide beneficial effects by lowering the side effects of co-administered therapeutic agents, in some cases acting as Tissue transport protein modulators. While blood tissue barrier structures, such as the blood-brain barrier (BBB, blood pancreas barrier, blood kidney barrier, and blood-placenta barrier), function as n obstacle to a isolate the tissues from the systemic blood circulation, some pharmaceutical agents, such as anesthetic agents, cross the tissues selectively causing tissue specific toxicity or side-effects rather than a desired localized action. In addition, blood tissue barriers may be compromised by disease states and therapeutic treatments, causing barrier laxity and then permitting unwanted agents to cross the barrier and adversely affect tissue structures. Thus, there is a continued need in the field for compounds that will lower side effects of co-administered therapeutic agents, such as new tissue transport protein modulators, and for compositions and methods for improved delivery of polyphenols, flavonoids, and related compounds.

SUMMARY OF THE INVENTION

One aspect of the invention is a solid composition for oral administration comprising a therapeutic agent, or its pharmaceutically or veterinarily acceptable salts, glycosides, esters, or prodrugs, and a phosphorylated polyphenol such as a phosphorylated pyrone analog, or its pharmaceutically or veterinarily acceptable salts, glycosides, esters, or prodrugs. In some embodiments, the phosphorylated polyphenol comprises a phosphorylated pyrone analog such as a phosphorylated flavonoid. In some embodiments, the phosphorylated pyrone analog such as a phosphorylated flavonoid comprises a phosphorylated pyrone analog such as a phosphorylated flavonoid glycoside or a phosphorylated pyrone analog such as a phosphorylated flavonoid aglycone.

In some embodiments, the phosphorylated pyrone analog such as a phosphorylated flavonoid is selected from the group consisting of phosphorylated quercetin, phosphorylated isoquercetin, phosphorylated quercitrin, phosphorylated flavone, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, and phosphorylated epicatechin. In some embodiments, the phosphorylated pyrone analog such as a phosphorylated flavonoid comprises phosphorylated quercetin, phosphorylated fisetin, or phosphorylated 5,7-dideoxyquercetin. In some embodiments the phosphorylated pyrone analog such as a phosphorylated flavonoid comprises quercetin-3'-O-phosphate. In some embodiments, the phosphorylated pyrone analog such as a phosphorylated flavonoid comprises phosphorylated fisetin. In some embodiments, the phosphorylated pyrone analog such as a phosphorylated flavonoid comprises phosphorylated 5,7-dideoxyquercetin.

In some embodiments, the phosphorylated polyphenol such as a phosphorylated pyrone analog comprises a monophosphate, diphosphate, triphosphate, tetraphosphate, or pentaphosphate.

In some embodiments, the phosphorylated polyphenol such as a phosphorylated pyrone analog comprises a compound with the structure of formula (XXXV), or its pharmaceutically or veterinarily acceptable salts, glycosides, esters, or prodrugs:

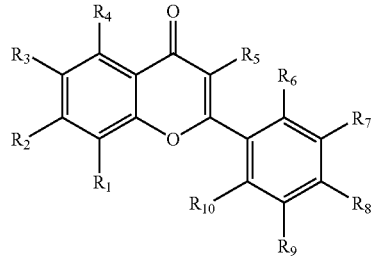

formula (XXXV)

wherein $R_1$, $R_2$, $R_3$, $R_4$, $R_5$, $R_6$, $R_7$, $R_8$, $R_9$, $R_{10}$ are independently selected from the group consisting of hydrogen, hydroxyl, —$OPO_3XY$, or —$OPO_3Z$, wherein X and Y are independently selected from hydrogen, methyl, ethyl, alkyl, carbohydrate, and a cation, wherein Z is a multivalent cation, and wherein at least one of the $R_1$-$R_{10}$ is —$OPO_3XY$, or —$OPO_3Z$.

In some embodiments, the phosphorylated polyphenol such as a phosphorylated pyrone analog comprises a compound with the structure of formula (XXXVII) or its pharmaceutically or veterinarily acceptable salts, glycosides, esters, or prodrugs:

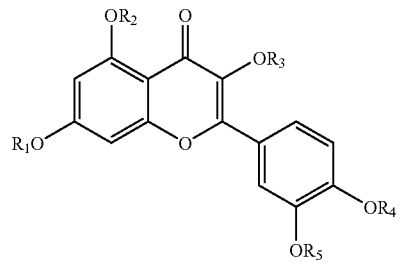

formula (XXXVI)

wherein $R_1$, $R_2$, $R_3$, $R_4$, and $R_5$ are independently selected from the group consisting of hydrogen, —$PO_3XY$, and —$PO_3Z$, wherein X and Y are independently selected from hydrogen, methyl, ethyl, alkyl, carbohydrate, and a cation, wherein Z is a multivalent cation, and wherein at least one of the $R_1$-$R_5$ is —$PO_3XY$, or —$PO_3Z$.

In some embodiments, the phosphorylated polyphenol such as a phosphorylated pyrone analog and/or its metabolite comprises a BBB transport protein modulator. In some embodiments, the BBB transport protein modulator comprises a BBB transport protein activator. In some embodiments, the BBB transport protein modulator comprises a modulator of P-gP.

In some embodiments, the phosphorylated polyphenol such as a phosphorylated pyrone analog and/or its metabolite comprises a side effect modulator such as a tissue specific effect modulator. In some embodiments, the tissue specific effect modulator is present in an amount sufficient to decrease kidney effects of the therapeutic agent when the composition is administered to an animal. In some embodiments, the tissue specific effect modulator is present in an amount sufficient to decrease a kidney specific effect of the therapeutic agent by an average of about 10% compared to the kidney effect without the kidney specific effect modulator.

In some embodiments, the side effect is selected from the group consisting of oliguria, azotemia, proteinuria, hematuria, electrolyte release, electrolyte retention, hypertension, hypotension, dependent edema, diffuse edema, hyperuricemia, anemia, coagulation disorders, In some embodiments, the side effect is selected from the group consisting of drowsiness, impaired concentration, sexual dysfunction, sleep disturbances, habituation, dependence, alteration of mood, respiratory depression, nausea, vomiting, lowered appetite, lassitude, lowered energy, dizziness, memory impairment, neuronal dysfunction, neuronal death, visual disturbance, impaired mentation, tolerance, addiction, hallucinations, lethargy, myoclonic jerking, endocrinopathies, and combinations thereof.

In some embodiments, the therapeutic agent is selected from the group consisting of immunosuppressants, antivirals, antibiotics, antineoplastics, amphetamines, antihypertensives, vasodilators, barbiturates, membrane stabilizers, cardiac stabilizers, glucocorticoids, antilipedemics, antiglycemics, cannabinoids, antidipressants, antineuroleptics, and antiinfectives. In some embodiments, the therapeutic agent comprises an antihypertensive agent. In some embodiments, the therapeutic agent comprises an immunosuppressive. In some embodiments, the therapeutic agent comprises an indirect calcineurin inhibitor. In some embodiments, the therapeutic agent comprises tacrolimus.

In some embodiments, the immunosuppressive is selected from the group consisting of tacrolimus, cyclosporin, cyclosporine, sirolimus, mycophenolate, voclosporin. In some embodiments, the tacrolimus is present in a range from about 0.001 mg to about 5000 mg and the compound of formula (I) to formula (XXXIX) is present in a range from about 0.05 mg and about 5000 mg. In some embodiments, the tacrolimus is present in a range from about 0.05 mg to about 500 mg and the compound of formula (I) to formula (XXXIX) is present in a range from about 10 mg and about 2500 mg. In some embodiments, the tacrolimus is present in a range from about 0.05 mg to about 500 mg and the compound of formula (I) to formula (XXXIX) is present in a range from about 10 mg and about 1250 mg.

In some embodiments, a therapeutic effect of the therapeutic agent is increased compared to the therapeutic effect without the phosphorylated polyphenol such as a phosphorylated pyrone analog. In some embodiments, a therapeutic effect of the therapeutic agent is increased an average of at least 10% compared to the therapeutic effect without the phosphorylated polyphenol such as a phosphorylated pyrone analog.

Some embodiments include a pharmaceutically acceptable excipient.

In some embodiments, the molar ratio of the therapeutic agent to the phosphorylated polyphenol such as a phosphorylated pyrone analog is about 0.001:1 to about 10:1.

In some embodiments, the therapeutic agent and the phosphorylated polyphenol such as a phosphorylated pyrone analog are present in a single container. In some embodiments, the therapeutic agent and the phosphorylated polyphenol such as a phosphorylated pyrone analog are admixed in the composition.

Another aspect of the invention is a kit comprising a container comprising a therapeutic agent, or its pharmaceutically or veterinarily acceptable salts, glycosides, esters, or prodrugs, and a phosphorylated polyphenol such as a phosphorylated pyrone analog, or its pharmaceutically or veterinarily acceptable salts, glycosides, esters, or prodrugs, and instructions for the use of the composition.

Another aspect of the invention is a composition comprising an immunosuppressive and a phosphorylated polyphenol such as a phosphorylated pyrone analog, or its pharmaceutically or veterinarily acceptable salts, glycosides, esters, or prodrugs. In some embodiments, the phosphorylated polyphenol such as a phosphorylated pyrone analog comprises a phosphorylated pyrone analog such as a phosphorylated flavonoid. In some embodiments, the flavonoid comprises a flavonoid glycoside or a flavonoid aglycone. In some embodiments, the immunosuppressive is selected from the group consisting of sirolimus, tacrolimus, mycophenolate, methadone, cyclosporin, cyclosporine, prednisone, or voclosporin.

In some embodiments, the composition comprises a liquid. In some embodiments, the composition is suitable for injection.

In some embodiments, the immunosuppressive comprises a calcineurin inhibitor. In some embodiments, the calcineurin inhibitor comprises tacrolimus.

Another aspect of the invention is a composition comprising an ionic complex comprising an immunosuppressive and a phosphorylated polyphenol such as a phosphorylated pyrone analog or its pharmaceutically or veterinarily acceptable salts, glycosides, esters, or prodrugs. In some embodiments, the phosphorylated polyphenol comprises a phosphorylated pyrone analog such as a phosphorylated flavonoid. In some embodiments, the flavonoid is a flavonoid glycoside or a flavonoid aglycone. In some embodiments, the immunosuppressive comprises a calcineurin inhibitor. In some embodiments, the immunosuppressive comprises tacrolimus.

In some embodiments, a phosphate moiety comprises an anion in the ionic complex. In some embodiments, an amine group comprises a cation of the ionic complex. In some embodiments, the amine group is protonated. In some embodiments, the amine group comprises a primary, secondary, or tertiary amine.

Another aspect of the invention is a composition comprising the compound of formula (XXXVIII), or its pharmaceutically or veterinarily acceptable salts, glycosides, esters, or prodrugs:

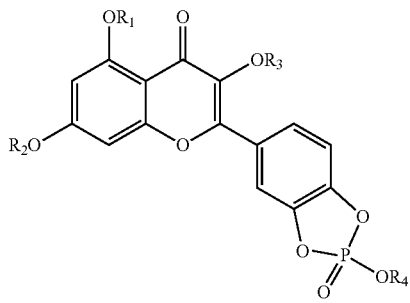

formula (XXXVIII)

wherein $R_1$, $R_2$, and $R_3$ are each independently selected from the group consisting of hydrogen, —$PO_3XY$, and —$PO_3Z$, wherein X and Y are independently selected from hydrogen, methyl, ethyl, alkyl, carbohydrate, and a cation, wherein Z is a multivalent cation, and wherein R4 is selected from the group consisting of hydrogen, methyl, ethyl, alkyl, carbohydrate, and a cation.

Another aspect of the invention is a method of treating an animal comprising; administering an animal in need of treatment an effective amount of a solid composition comprising a therapeutic agent and a phosphorylated polyphenol such as a phosphorylated pyrone analog, or its pharmaceutically or veterinarily acceptable salts, glycosides, esters, or prodrugs.

In some embodiments, the method comprises administering a solid composition comprising a therapeutic agent and phosphorylated polyphenol such as a phosphorylated pyrone analog comprising a compound with the structure of formula (XXXV), or its pharmaceutically or veterinarily acceptable salts, glycosides, esters, or prodrugs:

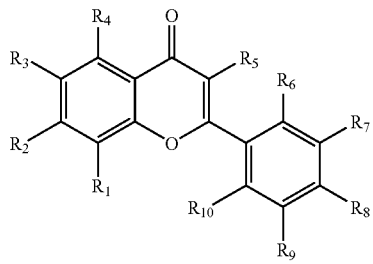

formula (XXXV)

wherein $R_1$, $R_2$, $R_3$, $R_4$, $R_5$, $R_6$, $R_7$, $R_8$, $R_9$, $R_{10}$ are independently selected from the group consisting of hydrogen, hydroxyl, —$OPO_3XY$, or —$OPO_3Z$, wherein X and Y are independently selected from hydrogen, methyl, ethyl, alkyl, carbohydrate, and a cation, wherein Z is a multivalent cation, and wherein at least one of the $R_1$-$R_{10}$ is —$OPO_3XY$, or —$OPO_3Z$.

In some embodiments, the method comprises administering a solid composition comprising a therapeutic agent and phosphorylated polyphenol such as a phosphorylated pyrone analog comprising a compound with the structure of formula (XXXVII) or its pharmaceutically or veterinarily acceptable salts, glycosides, esters, or prodrugs:

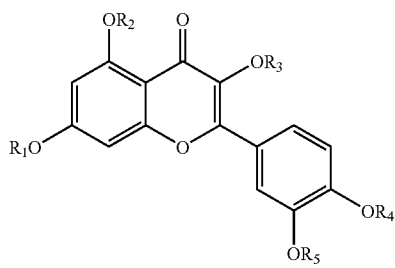

formula (XXXVII)

wherein $R_1$, $R_2$, $R_3$, $R_4$, and $R_5$ are independently selected from the group consisting of hydrogen, —$PO_3XY$, and —$PO_3Z$, wherein X and Y are independently selected from hydrogen, methyl, ethyl, alkyl, carbohydrate, and a cation, wherein Z is a multivalent cation, and wherein at least one of the $R_1$-$R_5$ is —$PO_3XY$, or —$PO_3Z$.

In some embodiments, the method comprises administering a phosphorylated polyphenol such as a phosphorylated pyrone analog comprising a compound of formula (XXXVIII), or its pharmaceutically or veterinarily acceptable salts, glycosides, esters, or prodrugs:

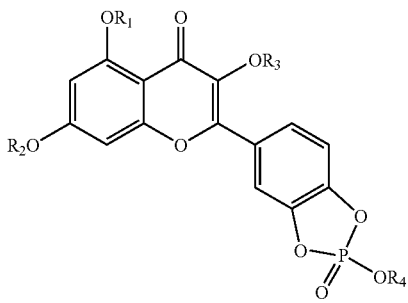

formula (XXXVIII)

wherein $R_1$, $R_2$, and $R_3$ are each independently selected from the group consisting of hydrogen, —$PO_3XY$, and —$PO_3Z$, wherein X and Y are independently selected from hydrogen, methyl, ethyl, alkyl, carbohydrate, and a cation, wherein Z is a multivalent cation, and wherein R4 is selected from the group consisting of hydrogen, methyl, ethyl, alkyl, carbohydrate, and a cation. In some embodiments the phosphorylated polyphenol such as a phosphorylated pyrone analog and/or its metabolite comprises a BTB transport protein modulator. In some embodiments the BTB transport protein modulator comprises a BTB transport protein activator. In some embodiments the BTB transport protein modulator comprises a modulator of P-gP.

In some embodiments of the method, the phosphorylated polyphenol such as a phosphorylated pyrone analog and/or its metabolite comprises a side effect modulator such as a tissue specific effect modulator. In some embodiments of the method, the tissue specific effect modulator is present in an amount sufficient to decrease a central nervous system (CNS) effect of the therapeutic agent when the composition is administered to an animal. In some embodiments the tissue specific effect modulator is present in an amount sufficient to decrease a central nervous system (CNS) effect of the therapeutic agent by an average of about 10% compared to the tissue specific effect without the tissue specific effect modulator.

In some embodiments of the method the side effect is selected from the group consisting of drowsiness, impaired concentration, sexual dysfunction, sleep disturbances, habituation, dependence, alteration of mood, respiratory depression, nausea, vomiting, lowered appetite, lassitude, lowered energy, dizziness, memory impairment, neuronal dysfunction, neuronal death, visual disturbance, impaired mentation, tolerance, addiction, hallucinations, lethargy, myoclonic jerking, endocrinopathies, and combinations thereof.

In some embodiments of the method the therapeutic agent is selected from the group consisting of immunosuppressants, antivirals, antibiotics, antineoplastics, amphetamines, antihypertensives, vasodilators, barbiturates, membrane stabilizers, cardiac stabilizers, glucocorticoids, antilipedemics, antiglycemics, cannabinoids, antidipressants, antineuroleptics, and antiinfectives. The therapeutic agent can be an antihypertensive agent. The therapeutic agent can be an immunosuppressive, such as an calcineurin immunosuppressant, for example, tacrolimus. In some embodiments of the method the immunosuppressive is selected from the group consisting of sirolimus, tacrolimus, mycophenolate, methadone, cyclosporin, cyclosporine, prednisone, or voclosporin.

In some embodiments of the method, the tacrolimus is present in a range from about 0.001 mg to about 5000 mg and the compound of formula (I) to formula (XXXIX) is present in a range from about 5 mg and about 5000 mg. In some embodiments, the tacrolimus is present in a range from about 5 mg to about 500 mg and the compound of formula (I) to formula (XXXIX) is present in a range from about 10 mg and about 2500 mg. In some embodiments, the tacrolimus is present in a range from about 5 mg to about 100 mg and the compound of formula (I) to formula (XXXIX)) is present in a range from about 10 mg and about 1250 mg.

In some embodiments of the method a therapeutic effect of the therapeutic agent is increased compared to the therapeutic effect without the phosphorylated polyphenol such as a phosphorylated pyrone analog. In some embodiments a therapeutic effect of the therapeutic agent is increased an average of at least 10% compared to the therapeutic effect without the phosphorylated polyphenol such as a phosphorylated pyrone analog.

Some embodiments of the method include a pharmaceutically acceptable excipient.

Another aspect of the invention is a method of treating an animal comprising, administering to an animal in need of treatment an immunosuppressive and a compound with a phosphorylated polyphenol such as a phosphorylated pyrone analog, or its pharmaceutically or veterinarily acceptable salts, glycosides, esters, or prodrugs. In some embodiments of the method the phosphorylated polyphenol such as a phosphorylated pyrone analog comprises a phosphorylated pyrone analog such as a phosphorylated flavonoid. In some embodiments of the method the flavonoid comprises a flavonoid glycoside or a flavonoid aglycone. In some embodiments of the method, the immunosuppressive is selected from the group consisting of sirolimus, tacrolimus, mycophenolate, methadone, cyclosporin, cyclosporine, voclosporin, or prednisone.

In some embodiments of the method the composition comprises a liquid. In some embodiments of the method the composition is suitable for injection. In some embodiments the immunosuppressive comprises a calcineurin inhibitor, for example, tacrolimus.

Another aspect of the invention is a method of treating an animal comprising, administering to an animal in need of treatment, an ionic complex comprising an immunosuppressive and a phosphorylated polyphenol such as a phosphorylated pyrone analog, or its pharmaceutically or veterinarily acceptable salts, glycosides, esters, or prodrugs.

Another aspect of the invention is a method of treating an animal comprising, administering to an animal in need of treatment, a therapeutic agent and the compound of formula (XXXVIII) as described above, or its pharmaceutically or veterinarily acceptable salts, glycosides, esters, or prodrugs.

Another aspect of the invention is a composition comprising a compound of formula (XXXIX), or its pharmaceutically or veterinarily acceptable salts, glycosides, esters, or prodrugs:

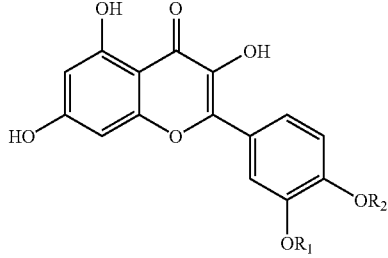

formula (XXXIX)

wherein $R_1$, and $R_2$ are each independently selected from the group consisting of hydrogen, —PO3XY, and —PO3Z, wherein X and Y are independently selected from hydrogen, methyl, ethyl, alkyl, carbohydrate, and a cation, wherein Z is a multivalent cation.

In some embodiments R2 is H, and R1 is either PO3XY, and —PO3Z. In some embodiments the compound comprises quercetin-3'-O-phosphate. In some embodiments R1 is H, and R2 is either PO3XY, and —PO3Z. In some embodiments the compound comprises quercetin-4'-O-phosphate.

In some embodiments the quercetin-3'-O-phosphate or quercetin-4'-O-phosphate has a purity of greater than about 90%. In some embodiments the quercetin-3'-O-phosphate or quercetin-4'-O-phosphate has a purity of greater than about 98%. In some embodiments the quercetin-3'-O-phosphate or quercetin-4'-O-phosphate has a purity of greater than about 99%. In some embodiments the quercetin-3'-O-phosphate or quercetin-4'-O-phosphate has a purity of greater than about 99.8%.

In some embodiments the compound comprises a mixture of quercetin-4'-O-phosphate and quercetin-3'-O-phosphate. In some embodiments the mixture has about 95% to about 100% of quercetin-3'-O-phosphate, and about 5% to about 0% of quercetin-4'-O-phosphate. In some embodiments the mixture has about 97% to about 100% of quercetin-3'-O-phosphate, and about 3% to about 0% of quercetin-4'-O-phosphate.

DETAILED DESCRIPTION OF THE INVENTION

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

I. INTRODUCTION

Figure 1:
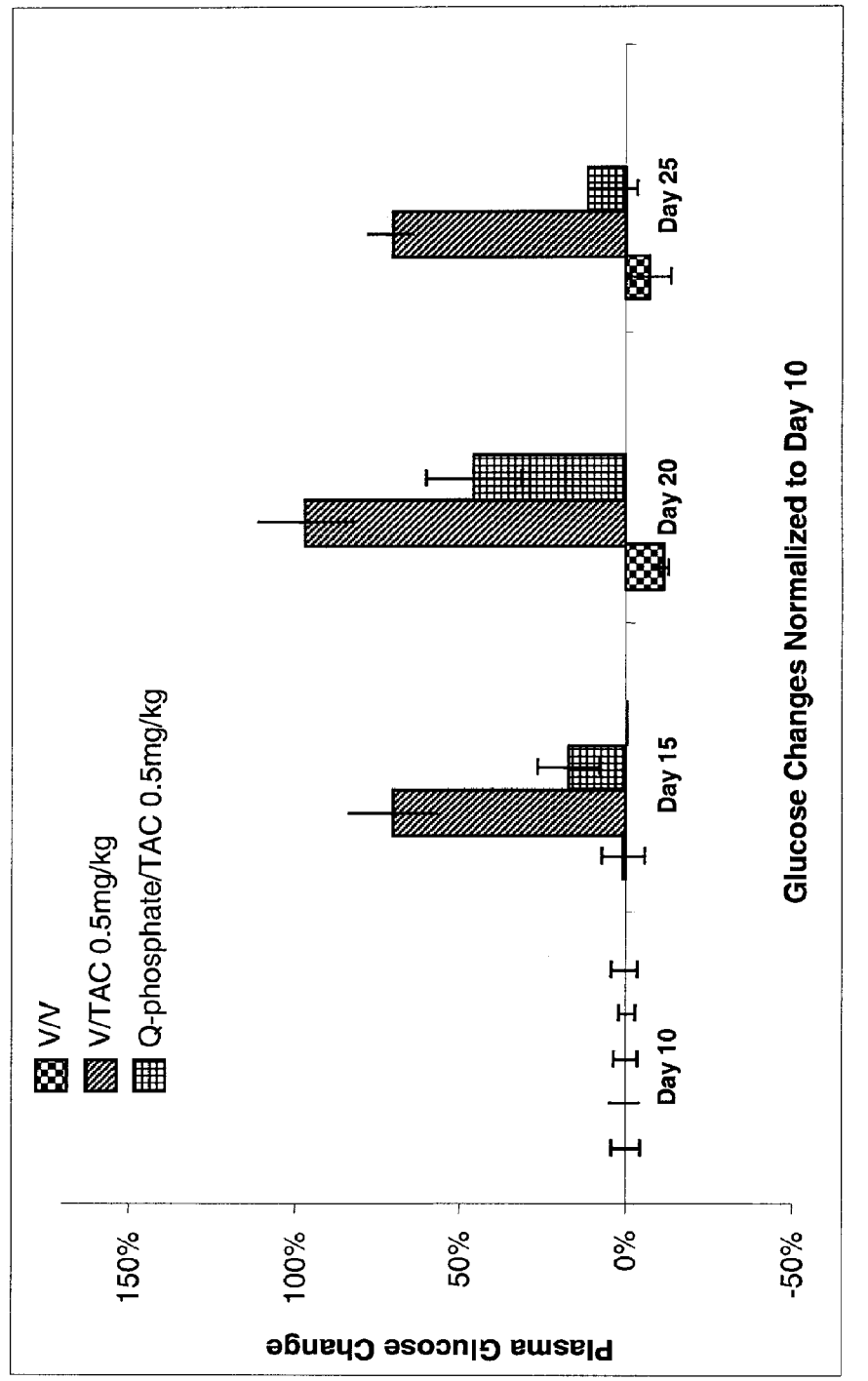
FIG. 1 is a graph of blood glucose measurements in rats showing attenuation of tacrolimus induced hyperglycemia by phosphorylated quercetin.

This invention provides compositions and methods utilizing phosphorylated compounds and/or their metabolites which act in combination with a therapeutic agent to enhance the effectiveness and/or reduce the side effects of the therapeutic agent. The class of compounds of the invention is the class of phosphorylated polyphenol such as a phosphorylated pyrone analogs, for example phosphorylated flavonoids or phosphorylated polyhydroxylated aromatic compounds. Polyphenols, for example flavonoids can enhance the effectiveness and/or reduce the side effects of therapeutic agents, for example, immunosuppressants when administered in combination with such agents (see U.S. patent application Ser. Nos. 11/281,771, 11/281,984, 11/553,924, and 11/964, 377; and PCT Patent Applications PCT/US2007/82691 and PCT/2007/88827). This invention provides phosphorylated analogs of these compounds which can have increased solubility and increased bioavailability. In addition, when co-administered with a therapeutic agent, the compounds of the present invention can increase the duration of the therapeutic effect of the agent, for example resulting in a longer half life of therapeutic effect. In some cases, one or more phosphates is cleaved from the phosphorylated polyphenol such as a phosphorylated pyrone analog in the body, for instance where the phosphorylated phenol acts as a pro-drug, and the cleavage of the phosphate releases a bioactive drug. In these cases, the released phosphate is a non-toxic substance that is well tolerated in the body at the levels generated.

In one aspect, the invention provides compositions and methods utilizing a phosphorylated polyphenol such as a phosphorylated pyrone analog as a side effect modulator. A "side effect modulator" as used herein includes agents that reduce or eliminate one or more side effects of one or more substances. In some embodiments, the invention provides compositions and methods utilizing a combination of a therapeutic agent and a phosphorylated polyphenol such as a phosphorylated pyrone analog that acts as an agent to reduce or eliminate a side effect of the therapeutic agent. Typically, the side effect modulator is a modulator of a blood tissue barrier (BTB) transport protein. The methods and compositions are useful in the treatment of an animal in need of treatment, where it is desired that one or more side effects of a substance, e.g., therapeutic agent be reduced or eliminated. In embodiments further utilizing a therapeutic agent, the methods and compositions are useful in the treatment of an animal in need of treatment, where it is desired that one or more side effects of the therapeutic agent be reduced or eliminated while one or more of the therapeutic effects (e.g., peripheral effects) of the agent are retained or enhanced.

In some embodiments of the invention, the therapeutic agent is an immunosuppressive agent, such as a calcineurin inhibitor or a non-calcineurin inhibitor. In some embodiments of the invention, the therapeutic agent is a non-immunosuppressive agent. The phosphorylated polyphenol such as a phosphorylated pyrone analog and/or its metabolite, acting as an agent causing a decrease in the side effects of the therapeutic agent, e.g., a modulator of a BTB transport protein, may be an activator or an inhibitor of the protein. The modulatory effect may be dose-dependent, e.g., some modulators act as activators in one dosage range and inhibitors in another. In some embodiments, a modulator of a BTB transport protein is used in a dosage wherein it acts primarily as an activator.

In some embodiments the therapeutic agent is not an antipsychotic agent. In some embodiments, the therapeutic agent is not chlorpromazine.

Typically, the use of a phosphorylated polyphenol such as a phosphorylated pyrone analog and/or its metabolite as the BTB transport protein modulator, e.g., activator, results in a decrease in one or more side effects of the therapeutic agent. The therapeutic effect(s) of the agent may be decreased, remain the same, or increase; however, in preferred embodiments, if the therapeutic effect is decreased, it is not decreased to the same degree as the side effects. It will be appreciated that a given therapeutic agent may have more than one therapeutic effect and/or one or more side effects, and it is possible that the therapeutic ratio (in this case, the ratio of change in desired effect to change in undesired effect) may vary depending on which effect is measured. However, typically at least one therapeutic effect of the therapeutic agent is decreased to a lesser degree than at least one side effect of the therapeutic agent.

In addition, in some embodiments, one or more therapeutic effects of the agent is enhanced by use in combination with phosphorylated polyphenol such as a phosphorylated pyrone analog and/or its metabolite acting as a BTB transport protein modulator, while one or more side effects of the therapeutic agent is reduced or substantially eliminated. For example, in some embodiments, the immunosuppressive effect of an immunosuppressive agent is enhanced while one or more side effects of the agent is reduced or substantially eliminated.

Without being bound by theory, and as an example only of a possible mechanism, it is thought that the methods and compositions of the invention operate by reducing or eliminating the concentration of the therapeutic agent from a compartment or compartments in which it causes a side effect, while retaining or even increasing the effective concentration of the agent in the compartment or compartments where it exerts its therapeutic effect.

It will be appreciated that the therapeutic and/or side effects of an therapeutic agent may be mediated in part or in whole by one or more metabolites of the therapeutic agent, and that a BTB transport protein modulator that reduces or eliminates the side effect compartment concentration of the therapeutic agent and/or of one or active metabolites of the therapeutic agent that produce side effects, while retaining or enhancing a therapeutic compartment concentration of the therapeutic agent and/or one or more metabolites producing a therapeutic effect, is also encompassed by the methods and compositions of the invention. In addition, a phosphorylated polyphenol such as a phosphorylated pyrone analog may be converted in vivo to metabolites that have differing activities in the modulation of one or more BTB transport modulators, and these metabolites are also encompassed by the compositions and methods of the invention.

Hence, in some embodiments the invention provides compositions that include a therapeutic agent and a phosphorylated polyphenol such as a phosphorylated pyrone analog, where the therapeutic agent is present in an amount sufficient to exert a therapeutic effect and the phosphorylated polyphenol is present in an amount sufficient to decrease side effect of the therapeutic agent when compared to the side effect without the phosphorylated polyphenol, when the composition is administered to an animal. The decrease in the side effect can be measurable. The phosphorylated polyphenol and/or its metabolite is a BTB transport protein activator in some embodiments. In some embodiments the phosphorylated polyphenol is a modulator of ATP binding cassette (ABC) transport proteins. In some embodiments the phosphorylated polyphenol is a modulator of P-glycoprotein (P-gP).

In some embodiments, compositions of the invention include one or more than one therapeutic agent as well as one or more than one phosphorylated polyphenol. One or more of the therapeutic agents may have one or more side effects which are desired to be decreased.

Compositions of the invention may be prepared in any suitable form for administration to an animal. In some embodiments, the invention provides pharmaceutical compositions.

In some embodiments, the invention provides compositions suitable for oral administration. In some embodiments, compositions are suitable for transdermal administration. In some embodiments, compositions are suitable for injection by any standard route of injection, e.g., intravenous, subcutaneous, intramuscular, or intraperitoneal. Compositions suitable for other routes of administration are also encompassed by the invention, as described herein.

The phosphorylated polyphenols of use in the invention include any phosphorylated polyphenol that results in the desired decrease in side effect of a therapeutic agent and/or the increased therapeutic effect of the therapeutic agent, for example, that is a suitable BTB transport protein modulator. In some embodiments, the phosphorylated polyphenol is one or more phosphorylated flavonoids or phosphorylated polyhydroxylated aromatic compounds. In some embodiments, the BTB transport protein modulator is a phosphorylated quercetin. In some embodiments, the BTB transport protein modulator is a phosphorylated fisetin. In some embodiments, the BTB transport protein modulator is a phosphorylated 5,7-dideoxyquercetin. In some embodiments, the BTB transport protein modulator is a quercetin-3'-O-phosphate.

In some embodiments the invention provides methods of treatment. In certain embodiments, the invention provides a method of treating a condition by administering to an animal suffering from the condition an effective amount of a therapeutic agent and an amount of a phosphorylated polyphenol, e.g. phosphorylated pyrone analog such as a phosphorylated flavonoid, such as a phosphorylated quercetin, phosphorylated fisetin, or phosphorylated 5,7-dideoxyquercetin, sufficient to reduce or eliminate a side effect of the therapeutic agent. In some embodiments the phosphorylated polyphenol and/or its metabolite is a BTB transport protein activator. In some embodiments, the therapeutic agent is an immunosuppressive agent, e.g., an calcineurin inhibitor or a non-calcineurin inhibitor. In certain embodiments the invention provides methods for the prevention of solid organ graft rejection, e.g., host versus graft disease, or graft versus host disease by administration of an immunosuppressive agent, e.g., an calcineurin inhibitor.

In some embodiments the invention provides methods of decreasing a side effect of an agent in an animal, e.g. a human, that has received an amount of the agent sufficient to produce a side effect by administering to the animal, e.g., human, an amount of a phosphorylated polyphenol sufficient to reduce or eliminate the side effect. In certain embodiments, the agent is an anesthetic, e.g., a general anesthetic. In certain embodiments, the agent is a therapeutic agent or drug of abuse that has been administered in excess, e.g., in an overdose.

II. PHOSPHORYLATED POLYPHENOLS, PHOSPHORYLATED PYRONE ANALOGS, AND PHOSPHORYLATED FLAVONOIDS OF THE INVENTION

The phosphorylated polyphenols and phosphorylated pyrone analogs of the invention can be derived from the class of compounds referred to as polyphenols, a group of chemical substances found characterized by the presence of more than one phenol group per molecule. Some polyphenols are naturally occurring in plants. Polyphenols can generally be subdivided into tannins, and phenylpropanoids such as lignins, and flavonoids. Suitable phosphorylated polyphenols include phosphorylated catechins. Catechins have been isolated from green tea, and include (−) epicatechin. See Wang, E, et al., Biochem. Biophys. Res. Comm. 297:412-418 (2002); Zhou, S., et al., Drug Metabol. Rev. 36:57-104 (2004), both of which are herein incorporated by reference in their entirety. Other suitable phosphorylated polyphenols for use herein include phosphorylated flavonols, including, but not limited to, phosphorylated kaempferol, phosphorylated quercetin, phosphorylated fisetin, phosphorylated 5,7-dideoxyquercetin, and phosphorylated galangin.

The chemistry for conversion of —OH groups to phosphate groups is well known in the art and can be accomplished for example by reaction with phosphoric acid (see e.g. Organic Letters, 7(10), (2005), 1999-2002). In other embodiments, phosphorylation will involve the conversion of an H group or other group bound directly to a carbon to a phosphate group such as —OPO$_3$XY or —OPO$_3$Z group where X and Y can be hydrogen, an alkyl (such as methyl or ethyl), a carbohydrate, or a cation, and where Z is a multivalent cation. The phosphate group can also be referred to as a phosphonoxy group. Some phosphorylated flavonoids useful in the present invention are described in WO 93/09786, JP 01308476, and JP 01153695. In some cases, the phosphorylated compound will have a cyclic phosphate structure, such as a 5 membered ring that is formed when the phosphorous of the phosphate bridges two hydroxyl groups on adjacent carbons.

In some cases the phosphorylated polyphenols of the invention comprise polyphosphate derivatives. Polyphosphate derivatives are those in which more than one phosphate is connected in a linear chain. Suitable polyphosphate derivatives include, for example, diphosphates (pyrophosphates), and triphosphates.

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Acyl" refers to a —(C=O)— radical which is attached to two other moieties through the carbon atom. Those groups may be chosen from alkyl, alkenyl, alkynyl, aryl, heterocyclic, heteroaliphatic, heteroaryl, and the like. Unless stated otherwise specifically in the specification, an acyl group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Acyloxy" refers to a R(C=O)O— radical wherein R is alkyl, aryl, heteroaryl or heterocyclyl. Unless stated otherwise specifically in the specification, an acyloxy group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylaryl" refers to an (alkyl)aryl—radical, where alkyl and aryl are as defined herein.

"Aralkyl" refers to an (aryl)alkyl—radical where aryl and alkyl are as defined herein.

"Alkoxy" refers to a (alkyl)O-radical, where alkyl is as described herein and contains 1 to 10 carbons (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. A alkoxy moiety is optionally substituted by one or more of the substituents described as suitable substituents for an alkyl radical.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Amine" refers to a —N(R$^a$)$_2$ radical group, where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, unless stated otherwise specifically in the specification. Unless stated otherwise specifically in the specification, an amino group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

An "amide" refers to a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system and includes both carbocyclic aryl (e.g., phenyl, fluorenyl, and naphthyl) and heterocyclic aryl (or "heteroaryl" or "heteroaromatic") groups (e.g., pyridine). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —CN —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Carboxaldehyde" refers to a —(C═O)H radical.

"Carboxyl" refers to a —(C═O)OH radical.

"Carbohydrate" as used herein, includes, but not limited to, monosaccharides, disaccharides, oligosaccharides, or polysaccharides. Monosaccharide for example includes, but not limited to, aldotrioses such as glyceraldehyde, ketotrioses such as dihydroxyacetone, aldotetroses such as erythrose and threose, ketotetroses such as erythrulose, aldopentoses such as arabinose, lyxose, ribose and xylose, ketopentoses such as ribulose and xylulose, aldohexoses such as allose, altrose, galactose, glucose, gulose, idose, mannose and talose, ketohexoses such as fructose, psicose, sorbose and tagatose, heptoses such as mannoheptulose, sedoheptulose, octoses such as octolose, 2-keto-3-deoxy-manno-octonate, nonoses such as sialoseallose. Disaccharides for example includes, but not limited to, glucorhamnose, trehalose, sucrose, lactose, maltose, galactosucrose, N-acetyllactosamine, cellobiose, gentiobiose, isomaltose, melibiose, primeverose, hesperodinose, and rutinose. Oligosaccharides for example includes, but not limited to, raffinose, nystose, panose, cellotriose, maltotriose, maltotetraose, xylobiose, galactotetraose, isopanose, cyclo-dextrin (α-CD) or cyclomaltohexaose, β-cyclodextrin (β-CD) or cyclomaltoheptaose and γ-cyclodextrin (γ-CD) or cyclomaltooctaose. Polysaccharide for example includes, but not limited to, xylan, mannan, galactan, glucan, arabinan, pustulan, gellan, guaran, xanthan, and hyaluronan. Some examples include, but not limited to, starch, glycogen, cellulose, insulin, chitin, amylose and amylopectin.

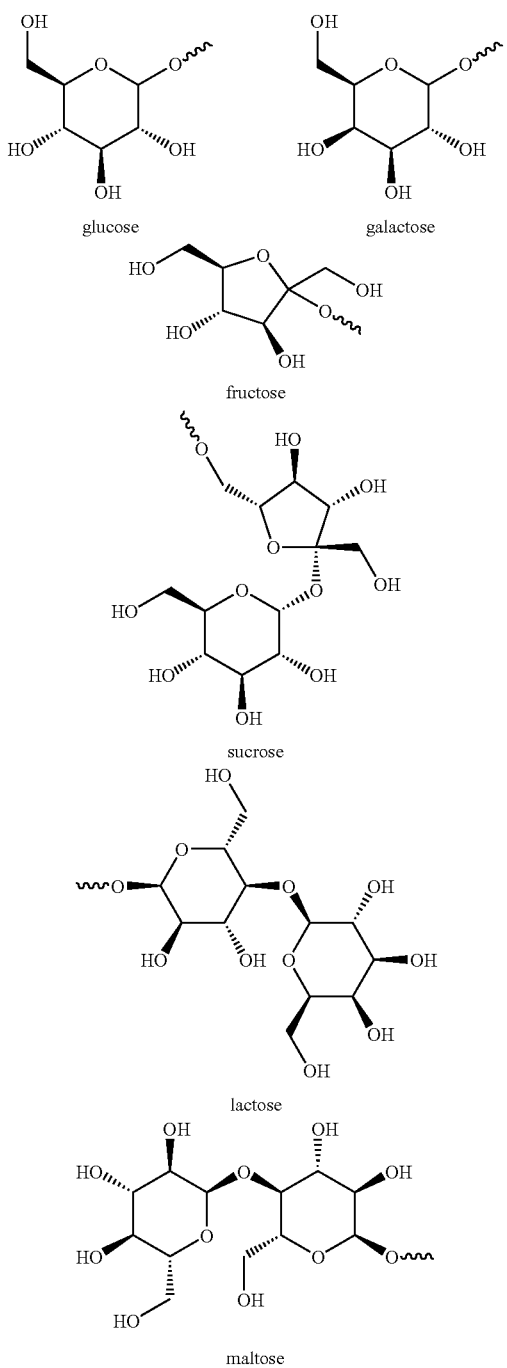

glucose galactose fructose sucrose lactose maltose

A compound of Formula I having a carbohydrate moiety can be referred to as the pyrone analog glycoside or the pyrone analog saccharide. As used herein, "carbohydrate" further encompasses the glucuronic as well as the glycosidic derivative of compounds of Formula I. Where the phosphorylated pyrone analog has no carbohydrate moiety, it can be referred to as the aglycone. Further, where a phenolic hydroxy is derivatized with any of the carbohydrates described above, the carbohydrate moiety is referred to as a glycosyl residue. Unless stated otherwise specifically in the specification, a carbohydrate group is optionally substituted by one or more substituents which are independently: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Cyano" refers to a —CN moiety.

"Cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms (ie. $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. illustrative examples of cycloalkyl groups include, but are not limited to the following moieties: cyclopropyl, cyclobutyl, cyclopentyl, cyclohexyl, cycloseptyl, cyclooctyl, cyclononyl, cyclodecyl, norbornyl, and the like. Unless stated otherwise specifically in the specification, a cycloalkyl group is optionally substituted by one or more substituents which are independently: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which are independently: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

"Heteroaryl" or, alternatively, "heteroaromatic" refers to a 5- to 18-membered aryl group (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h] quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$heterocyclic, $C_3$-$C_{10}$cycloalkyl, —CN, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Heterocyclyl" refers to a stable 3- to 18-membered nonaromatic ring (e.g., $C_3$-$C_{18}$ heterocyclyl) radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heteroaryl group may consist of 3 ring atoms, 4 ring atoms, etc., up to and including 18 ring atoms. In some embodiments, it is a $C_5$-$C_{10}$ heterocyclyl. In some embodiments, it is a $C_4$-$C_{10}$ heterocyclyl. In some embodiments, it is a $C_3$-$C_{10}$heterocyclyl. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl moiety is optionally substituted by one or more substituents which are independently: hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$heterocyclic, $C_3$-$C_{10}$cycloalkyl, —CN, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Heteroalicyclic" refers to a cycloalkyl radical that includes at least one heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless stated otherwise specifically in the specification, a heteroalicyclic group is optionally substituted by one or more substituents which independently are: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —OPO$_3$WY (where W and Y are hydrogen, methyl, ethyl, alkyl, carbohydrate, lithium, sodium or potassium) or —OPO$_3$Z (where Z is calcium, magnesium or iron) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Imino" refers to the =N—H radical.

"Isocyanato" refers to a —NCO radical.

"Isothiocyanato" refers to a —NCS radical.

"Mercaptyl" refers to a (alkyl)S— or (H)S— radical.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphorylted" refers to compounds comprising at least one phosphate group or phosphate moiety. A phosphate group includes the groups —OPO$_3$WY, —OCH$_2$PO$_4$WY, —OCH$_2$PO$_4$Z or —OPO$_3$Z as described herein. "Phosphorylation" refers to a reaction that produces a phosphorylated compound. Phosphorylated compounds, as used herein, includes compounds having a sugar-phosphate on the polyphenol, polyhydroxylated aromatic compound, or flavonoid. For example, a phosphorylated compound would include a compound with an inositol phosphate group. The addition of a sugar phosphate group to flavonoids is described in WO 96/21440.

"Sulfinyl" refers to a —S(=O)—R radical, where R is selected from the group consisting of alkyl, cycloalkyl, aryl, heteroaryl (bonded through a ring carbon) and heteroalicyclic (bonded through a ring carbon)

"Sulfonyl" refers to a —S(=O)$_2$—R radical, where R is selected from the group consisting of alkyl, cycloalkyl, aryl, heteroaryl (bonded through a ring carbon) and heteroalicyclic (bonded through a ring carbon).

"Sulfonamidyl" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon).

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon).

"Thiocyanato" refers to a —CNS radical.

"Thioxo" refers to the =S radical.

"Substituted" means that the referenced group may be substituted with one or more additional group(s) individually and independently selected from acyl, alkyl, alkylaryl, cycloalkyl, aralkyl, aryl, carbohydrate, heteroaryl, heterocyclic, hydroxy, alkoxy, aryloxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamidyl, sulfoxyl, sulfonate, and amino, including mono- and di-substituted amino groups, and the protected derivatives thereof. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

The compounds presented herein may possess one or more chiral centers and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds having the structure of Formula (I), as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

Phosphorylated pyrone analogs of the invention include compounds Formula I and their pharmaceutically/veterinarily acceptable salt or esters wherein the compound comprises at least one phosphate group,

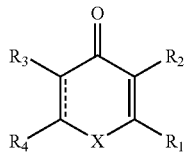

Formula I wherein X is O, S, or NR' wherein R' is hydrogen, $C_1$-$C_{10}$ alkyl, $C_2$-$C_{10}$ alkynyl, $C_2$-$C_{10}$ alkenyl, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$ heterocyclyl, heteroaryl, or $C_3$-$C_{10}$cycloalkyl;

$R_1$, and $R_2$ are independently hydrogen, hydroxyl, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, amine, aryl, $C_4$-$C_{10}$heterocyclyl, heteroaryl, $C_3$-$C_{10}$cycloalkyl, —OPO$_3$WY, —OCH$_2$PO$_4$WY, —OCH$_2$PO$_4$Z or —OPO$_3$Z;

$R_3$ and $R_4$ are independently hydrogen, hydroxyl, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl $C_6$-$C_{10}$ aralkyl acyl, $C_6$-$C_{10}$ alkylaryl acyl, alkoxy, amine, aryl, $C_4$-$C_{10}$ heterocyclyl, heteroaryl, $C_3$-$C_{10}$cycloalkyl, —OPO$_3$WY, —OCH$_2$PO$_4$WY, —OCH$_2$PO$_4$Z or —OPO$_3$Z;

or $R_3$ and $R_4$ are taken together to form a $C_5$-$C_{10}$heterocyclyl, $C_5$-$C_{10}$cycloalkyl, aryl, or heteroaryl; and W and Y are independently hydrogen, methyl, ethyl, alkyl, carbohydrate, or a cation, and Z is a multivalent cation.

In some embodiments, X is O.
In other embodiments, X is S.
In yet other embodiments, X is NR'.
In some embodiments, R' is hydrogen. In some embodiments, R' is unsubstituted $C_1$-$C_{10}$ alkyl. In some embodiments, R' is substituted $C_1$-$C_{10}$ alkyl. In some embodiments, R' is unsubstituted $C_2$-$C_{10}$ alkynyl. In some embodiments, R' is substituted $C_2$-$C_{10}$ alkynyl. In some embodiments, R' is unsubstituted $C_2$-$C_{10}$ alkenyl. In some embodiments, R' is substituted $C_2$-$C_{10}$ alkenyl. In some embodiments, R' is unsubstituted $C_1$-$C_{10}$ aliphatic acyl. In some embodiments, R' is substituted $C_1$-$C_{10}$ aliphatic acyl. In some embodiments, R' is unsubstituted $C_6$-$C_{10}$ aromatic acyl. In some embodiments, R' is substituted $C_6$-$C_{10}$ aromatic acyl. In some embodiments, R' is unsubstituted $C_6$-$C_{10}$ aralkyl acyl. In some embodiments, R' is substituted $C_6$-$C_{10}$ aralkyl acyl. In some embodiments, R' is unsubstituted $C_6$-$C_{10}$ alkylaryl acyl. In some embodiments, R' is substituted $C_6$-$C_{10}$ alkylaryl acyl. In some embodiments, R' is unsubstituted aryl. In some embodiments, R' is substituted aryl. In some embodiments, R' is unsubstituted $C_3$-$C_{10}$ heterocyclyl. In some embodiments, R' is substituted $C_3$-$C_{10}$ heterocyclyl. In some embodiments, R' is unsubstituted heteroaryl. In some embodiments, R' is substituted heteroaryl. In some embodiments, R' is unsubstituted $C_3$-$C_{10}$cycloalkyl. In some embodiments, R' is substituted $C_3$-$C_{10}$cycloalkyl.

In some embodiments, $R_1$ is hydrogen. In some embodiments, $R_1$ is optionally substituted $C_1$-$C_{10}$ alkyl. hydroxyl. In some embodiments, $R_1$ is unsubstituted $C_1$-$C_{10}$ alkyl. In some embodiments, $R_1$ is substituted $C_1$-$C_{10}$ alkyl. In some embodiments, $R_1$ is unsubstituted $C_1$-$C_{10}$ alkyl. In some other embodiments, $R_1$ is substituted $C_1$-$C_{10}$ alkyl. In some embodiments, $R_1$ is unsubstituted $C_2$-$C_{10}$ alkynyl. In some embodiments, $R_1$ is substituted $C_2$-$C_{10}$ alkynyl. In some embodiments, $R_1$ is unsubstituted $C_2$-$C_{10}$ alkenyl. In some embodiments, $R_1$ is substituted $C_2$-$C_{10}$ alkenyl. In some embodiments, $R_1$ is carboxyl. In some embodiments, $R_1$ is unsubstituted carbohydrate. In some embodiments, $R_1$ is substituted carbohydrate. In some embodiments, $R_1$ is unsubstituted ester. In some embodiments, $R_1$ is substituted ester. In some embodiments, $R_1$ is unsubstituted acyloxy. In some embodiments, $R_1$ is substituted acyloxy. In some embodiments, $R_1$ is nitro. In some embodiments, $R_1$ is halogen. In some embodiments, $R_1$ is unsubstituted $C_1$-$C_{10}$ aliphatic acyl. In some embodiments, $R_1$ is substituted $C_1$-$C_{10}$ aliphatic acyl. In some embodiments, $R_1$ is unsubstituted $C_6$-$C_{10}$ aromatic acyl. In some embodiments, $R_1$ is substituted $C_6$-$C_{10}$ aromatic acyl. In some embodiments, $R_1$ is unsubstituted $C_6$-$C_{10}$ aralkyl acyl. In some embodiments, $R_1$ is substituted $C_6$-$C_{10}$ aralkyl acyl. In some embodiments, $R_1$ is unsubstituted $C_6$-$C_{10}$ alkylaryl acyl. In some embodiments, $R_1$ is substituted $C_6$-$C_{10}$ alkylaryl acyl. In some embodiments, $R_1$ is unsubstituted alkoxy. In some embodiments, $R_1$ is substituted alkoxy. In some embodiments, $R_1$ is unsubstituted amine. In some embodiments, $R_1$ is substituted amine. In some embodiments, $R_1$ is unsubstituted aryl. In some embodiments, $R_1$ is substituted aryl. In some embodiments, $R_1$ is unsubstituted $C_4$-$C_{10}$heterocyclyl. In some embodiments, $R_1$ is substituted $C_4$-$C_{10}$ heterocyclyl. In some embodiments, $R_1$ is unsubstituted heteroaryl. In some embodiments, $R_1$ is substituted heteroaryl. In some embodiments, $R_1$ is unsubstituted $C_3$-$C_{10}$cycloalkyl. In some embodiments, $R_1$ is substituted $C_3$-$C_{10}$cycloalkyl. In some embodiments, $R_1$ is —OPO$_3$WY.

In some embodiments, $R_1$ is —OCH$_2$PO$_4$WY. In some embodiments, $R_1$ is —OCH$_2$PO$_4$Z. In some embodiments, $R_1$ is —OPO$_3$Z.

In some embodiments, when $R_1$ is aryl, it is monocyclic. In some embodiments, when $R_1$ is aryl, it is bicyclic. In some embodiments, when $R_1$ is heteroaryl, it is monocyclic. In some embodiments, when $R_1$ is heteroaryl, it is bicyclic.

In some embodiments, $R_2$ is hydrogen. In some embodiments, $R_2$ is hydroxyl. In some embodiments, $R_2$ is optionally substituted $C_1$-$C_{10}$ alkyl. In some embodiments, $R_2$ is unsubstituted $C_1$-$C_{10}$ alkyl. In some embodiments, $R_2$ is substituted $C_1$-$C_{10}$ alkyl. In some embodiments, $R_2$ is unsubstituted $C_1$-$C_{10}$ alkyl. In some other embodiments, $R_2$ is substituted $C_1$-$C_{10}$ alkyl. In some embodiments, $R_2$ is unsubstituted $C_2$-$C_{10}$ alkynyl. In some embodiments, $R_2$ is substituted $C_2$-$C_{10}$ alkynyl. In some embodiments, $R_2$ is unsubstituted $C_2$-$C_{10}$ alkenyl. In some embodiments, $R_2$ is substituted $C_2$-$C_{10}$ alkenyl. In some embodiments, $R_2$ is carboxyl. In some embodiments, $R_2$ is unsubstituted carbohydrate. In some embodiments, $R_2$ is substituted carbohydrate. In some embodiments, $R_2$ is unsubstituted ester. In some embodiments, $R_2$ is substituted ester. In some embodiments, $R_2$ is unsubstituted acyloxy. In some embodiments, $R_2$ is substituted acyloxy. In some embodiments, $R_2$ is nitro. In some embodiments, $R_2$ is halogen. In some embodiments, $R_2$ is unsubstituted $C_1$-$C_{10}$ aliphatic acyl. In some embodiments, $R_2$ is substituted $C_1$-$C_{10}$ aliphatic acyl. In some embodiments, $R_2$ is unsubstituted $C_6$-$C_{10}$ aromatic acyl. In some embodiments, $R_2$ is substituted $C_6$-$C_{10}$ aromatic acyl. In some embodiments, $R_2$ is unsubstituted $C_6$-$C_{10}$ aralkyl acyl. In some embodiments, $R_2$ is substituted $C_6$-$C_{10}$ aralkyl acyl. In some embodiments, $R_2$ is unsubstituted $C_6$-$C_{10}$ alkylaryl acyl. In some embodiments, $R_2$ is substituted $C_6$-$C_{10}$ alkylaryl acyl. In some embodiments, $R_2$ is unsubstituted alkoxy. In some embodiments, $R_2$ is substituted alkoxy. In some embodiments, $R_2$ is unsubstituted amine. In some embodiments, $R_2$ is substituted amine. In some embodiments, $R_2$ is unsubstituted aryl. In some embodiments, $R_2$ is substituted aryl. In some embodiments, $R_2$ is unsubstituted $C_4$-$C_{10}$ heterocyclyl. In some embodiments, $R_2$ is substituted $C_4$-$C_{10}$ heterocyclyl. In some embodiments, $R_2$ is unsubstituted heteroaryl. In some embodiments, $R_2$ is substituted heteroaryl. In some embodiments, $R_2$ is unsubstituted $C_3$-$C_{10}$ cycloalkyl. In some embodiments, $R_2$ is substituted $C_3$-$C_{10}$ cycloalkyl. In some embodiments, $R_2$ is —OPO$_3$WY. In some embodiments, $R_2$ is —OCH$_2$PO$_4$WY. In some embodiments, $R_2$ is —OCH$_2$PO$_4$Z. In some embodiments, $R_2$ is —OPO$_3$Z.

In some embodiments, $R_3$ is hydrogen. In some embodiments, $R_3$ is optionally substituted $C_1$-$C_{10}$ alkyl. hydroxyl. In some embodiments, $R_3$ is unsubstituted $C_1$-$C_{10}$ alkyl. In some embodiments, $R_3$ is substituted $C_1$-$C_{10}$ alkyl. In some embodiments, $R_3$ is unsubstituted $C_1$-$C_{10}$ alkyl. In some other embodiments, $R_3$ is substituted $C_1$-$C_{10}$ alkyl. In some embodiments, $R_3$ is unsubstituted $C_2$-$C_{10}$ alkynyl. In some embodiments, $R_3$ is substituted $C_2$-$C_{10}$ alkynyl. In some embodiments, $R_3$ is unsubstituted $C_2$-$C_{10}$ alkenyl. In some embodiments, $R_3$ is substituted $C_2$-$C_{10}$ alkenyl. In some embodiments, $R_3$ is carboxyl. In some embodiments, $R_3$ is unsubstituted carbohydrate. In some embodiments, $R_3$ is substituted carbohydrate. In some embodiments, $R_3$ is unsubstituted ester. In some embodiments, $R_3$ is substituted ester. In some embodiments, $R_3$ is unsubstituted acyloxy. In some embodiments, $R_3$ is substituted acyloxy. In some embodiments, $R_3$ is nitro. In some embodiments, $R_3$ is halogen. In some embodiments, $R_3$ is unsubstituted $C_1$-$C_{10}$ aliphatic acyl. In some embodiments, $R_3$ is substituted $C_1$-$C_{10}$ aliphatic acyl. In some embodiments, $R_3$ is unsubstituted $C_6$-$C_{10}$ aromatic acyl. In some embodiments, $R_3$ is substituted $C_6$-$C_{10}$ aromatic acyl. In some embodiments, $R_3$ is unsubstituted $C_6$-$C_{10}$ aralkyl acyl. In some embodiments, $R_3$ is substituted $C_6$-$C_{10}$ aralkyl acyl. In some embodiments, $R_3$ is unsubstituted $C_6$-$C_{10}$ alkylaryl acyl. In some embodiments, $R_3$ is substituted $C_6$-$C_{10}$ alkylaryl acyl. In some embodiments, $R_3$ is unsubstituted alkoxy. In some embodiments, $R_3$ is substituted alkoxy. In some embodiments, $R_3$ is unsubstituted amine. In some embodiments, $R_3$ is substituted amine. In some embodiments, $R_3$ is unsubstituted aryl. In some embodiments, $R_3$ is substituted aryl. In some embodiments, $R_3$ is unsubstituted $C_4$-$C_{10}$ heterocyclyl. In some embodiments, $R_3$ is substituted $C_4$-$C_{10}$ heterocyclyl. In some embodiments, $R_3$ is unsubstituted heteroaryl. In some embodiments, $R_3$ is substituted heteroaryl. In some embodiments, $R_3$ is unsubstituted $C_3$-$C_{10}$ cycloalkyl. In some embodiments, $R_3$ is substituted $C_3$-$C_{10}$ cycloalkyl. In some embodiments, $R_3$ is —OPO$_3$WY. In some embodiments, $R_3$ is —OCH$_2$PO$_4$WY. In some embodiments, $R_3$ is —OCH$_2$PO$_4$Z. In some embodiments, $R_3$ is —OPO$_3$Z.

In some embodiments, $R_4$ is hydrogen. In some embodiments, $R_4$ is optionally substituted $C_1$-$C_{10}$ alkyl. hydroxyl. In some embodiments, $R_4$ is unsubstituted $C_1$-$C_{10}$ alkyl. In some embodiments, $R_4$ is substituted $C_1$-$C_{10}$ alkyl. In some embodiments, $R_4$ is unsubstituted $C_1$-$C_{10}$ alkyl. In some other embodiments, $R_4$ is substituted $C_1$-$C_{10}$ alkyl. In some embodiments, $R_4$ is unsubstituted $C_2$-$C_{10}$ alkynyl. In some embodiments, $R_4$ is substituted $C_2$-$C_{10}$ alkynyl. In some embodiments, $R_4$ is unsubstituted $C_2$-$C_{10}$ alkenyl. In some embodiments, $R_4$ is substituted $C_2$-$C_{10}$ alkenyl. In some embodiments, $R_4$ is carboxyl. In some embodiments, $R_4$ is unsubstituted carbohydrate. In some embodiments, $R_4$ is substituted carbohydrate. In some embodiments, $R_4$ is unsubstituted ester. In some embodiments, $R_4$ is substituted ester. In some embodiments, $R_4$ is unsubstituted acyloxy. In some embodiments, $R_4$ is substituted acyloxy. In some embodiments, $R_4$ is nitro. In some embodiments, $R_4$ is halogen. In some embodiments, $R_4$ is unsubstituted $C_1$-$C_{10}$ aliphatic acyl. In some embodiments, $R_4$ is substituted $C_1$-$C_{10}$ aliphatic acyl. In some embodiments, $R_4$ is unsubstituted $C_6$-$C_{10}$ aromatic acyl. In some embodiments, $R_4$ is substituted $C_6$-$C_{10}$ aromatic acyl. In some embodiments, $R_4$ is unsubstituted $C_6$-$C_{10}$ aralkyl acyl. In some embodiments, $R_4$ is substituted $C_6$-$C_{10}$ aralkyl acyl. In some embodiments, $R_4$ is unsubstituted $C_6$-$C_{10}$ alkylaryl acyl. In some embodiments, $R_4$ is substituted $C_6$-$C_{10}$ alkylaryl acyl. In some embodiments, $R_4$ is unsubstituted alkoxy. In some embodiments, $R_4$ is substituted alkoxy. In some embodiments, $R_4$ is unsubstituted amine. In some embodiments, $R_4$ is substituted amine. In some embodiments, $R_4$ is unsubstituted aryl. In some embodiments, $R_4$ is substituted aryl. In some embodiments, $R_4$ is unsubstituted $C_4$-$C_{10}$ heterocyclyl. In some embodiments, $R_4$ is substituted $C_4$-$C_{10}$ heterocyclyl. In some embodiments, $R_4$ is unsubstituted heteroaryl. In some embodiments, $R_4$ is substituted heteroaryl. In some embodiments, $R_4$ is unsubstituted $C_3$-$C_{10}$ cycloalkyl. In some embodiments, $R_4$ is substituted $C_3$-$C_{10}$ cycloalkyl. In some embodiments, $R_4$ is —OPO$_3$WY. In some embodiments, $R_4$ is —OCH$_2$PO$_4$WY. In some embodiments, $R_4$ is —OCH$_2$PO$_4$Z. In some embodiments, $R_4$ is —OPO$_3$Z.

In some embodiments, $R_3$ and $R_4$ are taken together to form an unsubstituted $C_5$-$C_{10}$ heterocyclyl. In other embodiments, $R_3$ and $R_4$ are taken together to form a substituted $C_5$-$C_{10}$ heterocyclyl. In some embodiments, $R_3$ and $R_4$ are taken together to form an unsubstituted $C_5$-$C_{10}$ cycloalkyl. In some embodiments, $R_3$ and $R_4$ are taken together to form a substituted $C_5$-$C_{10}$cycloalkyl. In some embodiments, $R_3$ and $R_4$ are taken together to form an unsubstituted aryl. In some embodiments, $R_3$ and $R_4$ are taken together to form a substituted aryl. In some embodiments, $R_3$ and $R_4$ are taken together to form an unsubstituted heteroaryl. In some embodiments, $R_3$ and $R_4$ are taken together to form a substituted heteroaryl.

In various embodiments, W is hydrogen. In various embodiments, W is unsubstituted methyl. In various embodiments, W is substituted methyl. In various embodiments, W is unsubstituted ethyl. In various embodiments, W is substituted ethyl. In various embodiments, W is unsubstituted alkyl. In various embodiments, W is substituted alkyl. In various embodiments, W is unsubstituted carbohydrate. In various embodiments, W is substituted carbohydrate. In various embodiments, W is potassium. In various embodiments, W is sodium. In various embodiments, W is lithium. In various embodiments, Y is hydrogen. In various embodiments, Y is unsubstituted methyl. In various embodiments, Y is substituted methyl. In various embodiments, Y is unsubstituted ethyl. In various embodiments, Y is substituted ethyl. In various embodiments, Y is unsubstituted alkyl. In various embodiments, Y is substituted alkyl. In various embodiments, Y is unsubstituted carbohydrate. In various embodiments, Y is substituted carbohydrate. In various embodiments, Y is potassium. In various embodiments, Y is sodium. In various embodiments, Y is lithium.

In various embodiments, Z is calcium. In various embodiments, Z is magnesium. In various embodiments, Z is iron.

The 2,3 bond may be saturated or unsaturated in the compounds of Formula I.

In some embodiments of the invention, the phosphorylated pyrone analog of Formula I is of Formula II wherein the compound comprises at least one phosphate group:

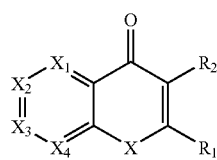

Formula II wherein X, $R_1$, $R_2$, W, Y, and Z are defined as in Formula I; $X_1$, $X_2$, $X_3$, and $X_4$ are independently $CR_5$, O, S, or N;

each instance of $R_5$ is independently hydrogen, hydroxyl, carboxaldehyde, amino, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$alkylaryl acyl, alkoxy, amine, aryl, $C_3$-$C_{10}$heterocyclyl, heteroaryl, $C_3$-$C_{10}$cycloalkyl, —$OPO_3WY$, —$OCH_2PO_4WY$, —$OCH_2PO_4Z$ or —$OPO_3Z$.

In some embodiments, $X_1$ is $CR_5$.
In other embodiments, $X_1$ is O.
In yet other embodiments, $X_1$ is S.
In further embodiments, $X_1$ is N.
In some embodiments, $X_2$ is $CR_5$.
In other embodiments, $X_2$ is O.
In yet other embodiments, $X_2$ is S.
In further embodiments, $X_2$ is N.
In some embodiments, $X_3$ is $CR_5$.
In other embodiments, $X_3$ is O.
In yet other embodiments, $X_3$ is S.
In further embodiments, $X_3$ is N.
In other embodiments, $X_4$ is $CR_5$.
In some embodiments, $X_4$ is O.

In yet other embodiments, $X_4$ is S.
In some embodiments, $X_4$ is N.
In some embodiments, $X_1$, $X_2$, $X_3$, and $X_4$ are $CR_5$.
In some embodiments, $X_1$ and $X_3$ are $CR_5$ and $X_2$ and $X_4$ are N.
In some embodiments, $X_2$ and $X_4$ are $CR_5$ and $X_1$ and $X_3$ are N.
In some embodiments, $X_2$ and $X_3$ are $CR_5$ and $X_1$ and $X_4$ are N.

In various embodiments, $R_1$ is one of the following formulae:

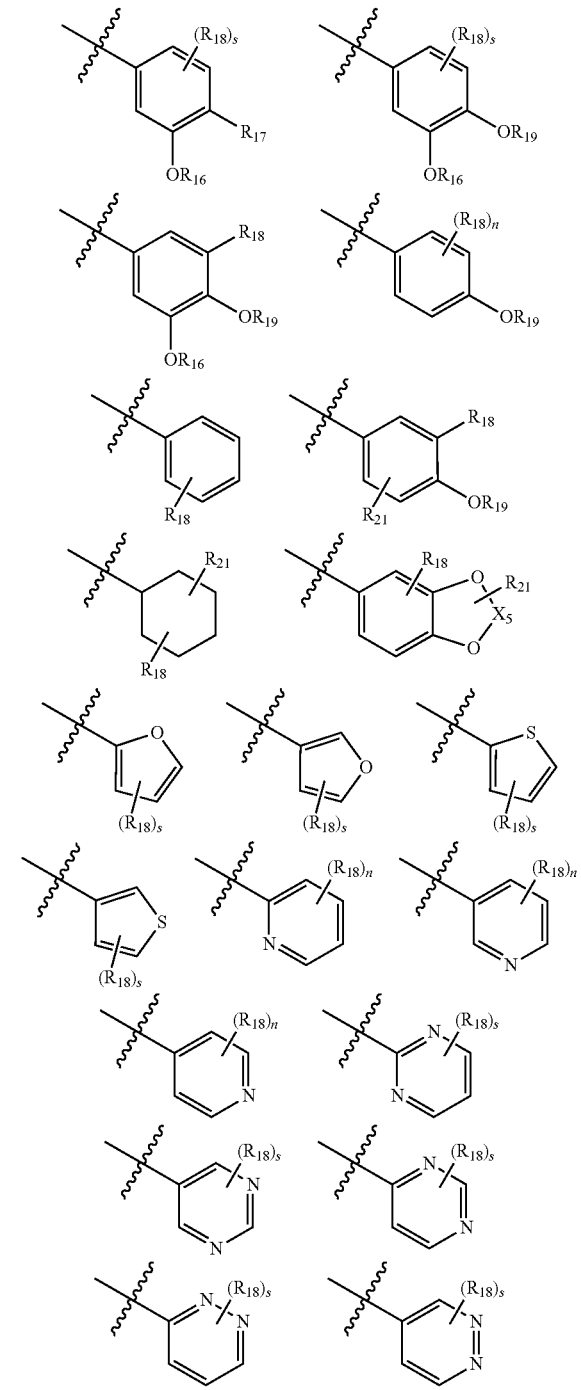

wherein $R_{16}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$ heterocyclyl, heteroaryl, $C_3$-$C_{10}$cycloalkyl, —$PO_3WY$, —$CH_2PO_4WY$, —$CH_2PO_4Z$ or —$PO_3Z$;

$R_{17}$ is hydrogen, hydroxy, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, aryl, $C_3$-$C_{10}$ heterocyclyl, heteroaryl, or $C_3$-$C_{10}$cycloalkyl, —$OPO_3WY$, —$OCH_2PO_4WY$, —$OCH_2PO_4Z$ or —$OPO_3Z$;

each instance of $R_{18}$ and $R_{21}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$;

$R_{19}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$heterocyclyl, heteroaryl, optionally substituted $C_3$-$C_{10}$cycloalkyl, —$PO_3WY$, —$CH_2PO_4WY$, —$CH_2PO_4Z$ or —$PO_3Z$;

s is an integer of 0, 1, 2, or 3; and n is an integer of 0, 1, 2, 3, or 4.

In some embodiments, $R_{16}$ is hydrogen. In some embodiments, $R_{16}$ is unsubstituted $C_1$-$C_{10}$ alkyl. In some embodiments, $R_{16}$ is substituted $C_1$-$C_{10}$ alkyl. In some embodiments, $R_{16}$ is unsubstituted $C_2$-$C_{10}$ alkynyl. In some embodiments, $R_{16}$ is substituted $C_2$-$C_{10}$ alkynyl. In some embodiments, $R_{16}$ is unsubstituted $C_2$-$C_{10}$ alkenyl. In some embodiments, $R_{16}$ is substituted $C_2$-$C_{10}$ alkenyl. In some embodiments, $R_{16}$ is unsubstituted carbohydrate 1. In some embodiments, $R_{16}$ is substituted carbohydrate. In some embodiments, $R_{16}$ is unsubstituted $C_1$-$C_{10}$ aliphatic acyl. In some embodiments, $R_{16}$ is substituted $C_1$-$C_{10}$ aliphatic acyl. In some embodiments, $R_{16}$ is unsubstituted $C_6$-$C_{10}$ aromatic acyl. In some embodiments, $R_{16}$ is substituted $C_6$-$C_{10}$ aromatic acyl. In some embodiments, $R_{16}$ is unsubstituted $C_6$-$C_{10}$ aralkyl acyl. In some embodiments, $R_{16}$ is substituted $C_6$-$C_{10}$ aralkyl acyl. In some embodiments, $R_{16}$ is unsubstituted $C_6$-$C_{10}$ alkylaryl acyl. In some embodiments, $R_{16}$ is substituted $C_6$-$C_{10}$ alkylaryl acyl. In some embodiments, $R_{16}$ is unsubstituted aryl. In some embodiments, $R_{16}$ is substituted aryl. In some embodiments, $R_{16}$ is unsubstituted $C_3$-$C_{10}$heterocyclyl. In some embodiments, $R_{16}$ is substituted $C_3$-$C_{10}$heterocyclyl. In some embodiments, $R_{16}$ is unsubstituted heteroaryl. In some embodiments, $R_{16}$ is substituted heteroaryl. In some embodiments, $R_{16}$ is unsubstituted $C_3$-$C_{10}$cycloalkyl. In some embodiments, $R_{16}$ is substituted $C_3$-$C_{10}$cycloalkyl. In some embodiments, $R_{16}$ is —$PO_3WY$. In some embodiments, $R_{16}$ is —$CH_2PO_4WY$. In some embodiments, $R_{16}$ is —$CH_2PO_4Z$. In some embodiments, $R_{16}$ is —$PO_3Z$.

In some embodiments, $R_{17}$ is hydrogen. In some embodiments, $R_{17}$ is hydroxy. In some embodiments, $R_{17}$ is carboxaldehyde. In some embodiments, $R_{17}$ is unsubstituted amine. In some embodiments, $R_{17}$ is substituted amine. In some embodiments, $R_{17}$ is unsubstituted $C_1$-$C_{10}$ alkyl. In some embodiments, $R_{17}$ is unsubstituted $C_2$-$C_{10}$ alkynyl. In some embodiments, $R_{17}$ is substituted $C_2$-$C_{10}$ alkynyl. In some embodiments, $R_{17}$ is unsubstituted $C_2$-$C_{10}$ alkenyl. In some embodiments, $R_{17}$ is substituted $C_2$-$C_{10}$ alkenyl. In some embodiments, $R_{17}$ is carboxyl. In some embodiments, $R_{17}$ is unsubstituted carbohydrate. In some embodiments, $R_{17}$ is substituted carbohydrate. In some embodiments, $R_{17}$ is unsubstituted ester. In some embodiments, $R_{17}$ is substituted ester. In some embodiments, $R_{17}$ is unsubstituted acyloxy. In some embodiments, $R_{17}$ is substituted acyloxy. In some embodiments, $R_{17}$ is nitro. In some embodiments, $R_{17}$ is halogen. In some embodiments, $R_{17}$ is unsubstituted $C_1$-$C_{10}$ aliphatic acyl. In some embodiments, $R_{17}$ is substituted $C_1$-$C_{10}$ aliphatic acyl. In some embodiments, $R_{17}$ is unsubstituted $C_6$-$C_{10}$ aromatic acyl. In some embodiments, $R_{17}$ is substituted $C_6$-$C_{10}$ aromatic acyl. In some embodiments, $R_{17}$ is unsubstituted $C_6$-$C_{10}$ aralkyl acyl. In some embodiments, $R_{17}$ is substituted $C_6$-$C_{10}$ aralkyl acyl. In some embodiments, $R_{17}$ is unsubstituted $C_6$-$C_{10}$ alkylaryl acyl. n some embodiments, $R_{17}$ is substituted $C_6$-$C_{10}$ alkylaryl acyl. In some embodiments, $R_{17}$ is unsubstituted alkoxy. In some embodiments, $R_{17}$ is substituted alkoxy. In some embodiments, $R_{17}$ is unsubstituted aryl. In some embodiments, $R_{17}$ is substituted aryl. In some embodiments, $R_{17}$ is unsubstituted $C_3$-$C_{10}$heterocyclyl. In some embodiments, $R_{17}$ is substituted $C_3$-$C_{10}$heterocyclyl. In some embodiments, $R_{17}$ is unsubstituted heteroaryl. In some embodiments, $R_{17}$ is substituted heteroaryl. In some embodiments, $R_{17}$ is unsubstituted $C_3$-$C_{10}$cycloalkyl. In some embodiments, $R_{17}$ is substituted $C_3$-$C_{10}$cycloalkyl. In some embodiments, $R_{17}$ is —$OPO_3WY$. In some embodiments, $R_{17}$ is —$OCH_2PO_4WY$. In some embodiments, $R_{17}$ is —$OCH_2PO_4Z$. In some embodiments, $R_{17}$ is —$OPO_3Z$.

In some embodiments, $R_{18}$ is hydrogen. In some embodiments, $R_{18}$ is hydroxy. In some embodiments, $R_{18}$ is carboxaldehyde. In some embodiments, $R_{18}$ is unsubstituted amine. In some embodiments, $R_{18}$ is substituted amine. In some embodiments, $R_{18}$ is unsubstituted $C_1$-$C_{10}$ alkyl. In some embodiments, $R_{18}$ is unsubstituted $C_2$-$C_{10}$ alkynyl. In some embodiments, $R_{18}$ is substituted $C_2$-$C_{10}$ alkynyl. In some embodiments, $R_{18}$ is unsubstituted $C_2$-$C_{10}$ alkenyl. In some embodiments, $R_{18}$ is substituted $C_2$-$C_{10}$ alkenyl. In some embodiments, $R_{18}$ is carboxyl. In some embodiments, $R_{18}$ is unsubstituted carbohydrate. In some embodiments, $R_{18}$ is substituted carbohydrate. In some embodiments, $R_{18}$ is substituted carbohydrate. In some embodiments, $R_{18}$ is unsubstituted ester. In some embodiments, $R_{18}$ is substituted ester. In some embodiments, $R_{18}$ is unsubstituted acyloxy. In some embodiments, $R_{18}$ is substituted acyloxy. In some embodiments, $R_{18}$ is nitro. In some embodiments, $R_{18}$ is halogen. In some embodiments, $R_{18}$ is unsubstituted $C_1$-$C_{10}$ aliphatic acyl. In some embodiments, $R_{18}$ is substituted $C_1$-$C_{10}$ aliphatic acyl. In some embodiments, $R_{18}$ is unsubstituted $C_6$-$C_{10}$ aromatic acyl. In some embodiments, $R_{18}$ is substituted $C_6$-$C_{10}$ aromatic acyl. In some embodiments, $R_{18}$ is unsubstituted $C_6$-$C_{10}$ aralkyl acyl. In some embodiments, $R_{18}$ is substituted $C_6$-$C_{10}$ aralkyl acyl. In some embodiments, $R_{18}$ is unsubstituted $C_6$-$C_{10}$ alkylaryl acyl. In some embodiments, $R_{18}$ is substituted $C_6$-$C_{10}$ alkylaryl acyl. In some embodiments, $R_{18}$ is unsubstituted alkoxy. In some embodiments, $R_{18}$ is substituted alkoxy. In some embodiments, $R_{18}$ is unsubstituted aryl. In some embodiments, $R_{18}$ is substituted aryl. In some embodiments, $R_{18}$ is unsubstituted $C_3$-$C_{10}$heterocyclyl. In some embodiments, $R_{18}$ is substituted $C_3$-$C_{10}$heterocyclyl. In some embodiments, $R_{18}$ is unsubstituted heteroaryl. In some embodiments, $R_{18}$ is substituted heteroaryl. In some embodiments, $R_{18}$ is unsubstituted $C_3$-$C_{10}$cycloalkyl. In some embodiments, $R_{18}$ is substituted $C_3$-$C_{10}$cycloalkyl. In some embodiments, $R_{18}$ is —$OPO_3WY$. In some embodiments, $R_{18}$ is —$OCH_2PO_4WY$. In some embodiments, $R_{18}$ is —$OCH_2PO_4Z$. In some embodiments, $R_{18}$ is —$OPO_3Z$.

In some embodiments, $R_{19}$ is hydrogen. In some embodiments, $R_{19}$ is unsubstituted $C_1$-$C_{10}$ alkyl. In some embodiments, $R_{19}$ is substituted $C_1$-$C_{10}$ alkyl. In some embodiments, $R_{19}$ is unsubstituted $C_2$-$C_{10}$ alkynyl. In some embodiments, $R_{19}$ is substituted $C_2$-$C_{10}$ alkynyl. In some embodiments, $R_{19}$ is unsubstituted $C_2$-$C_{10}$ alkenyl. In some embodiments, $R_{19}$ is substituted $C_2$-$C_{10}$ alkenyl. In some embodiments, $R_{19}$ is unsubstituted carbohydrate. In some embodiments, $R_{19}$ is substituted carbohydrate. In some embodiments, $R_{19}$ is unsubstituted $C_1$-$C_{10}$ aliphatic acyl. In some embodiments, $R_{19}$ is substituted $C_1$-$C_{10}$ aliphatic acyl. In some embodiments, $R_{19}$ is unsubstituted $C_6$-$C_{10}$ aromatic acyl. In some embodiments, $R_{19}$ is substituted $C_6$-$C_{10}$ aromatic acyl. In some embodiments, $R_{19}$ is unsubstituted $C_6$-$C_{10}$ aralkyl acyl. In some embodiments, $R_{19}$ is substituted $C_6$-$C_{10}$ aralkyl acyl. In some embodiments, $R_{19}$ is unsubstituted $C_6$-$C_{10}$ alkylaryl acyl. In some embodiments, $R_{19}$ is substituted $C_6$-$C_{10}$ alkylaryl acyl. In some embodiments, $R_{19}$ is unsubstituted aryl. In some embodiments, $R_{19}$ is substituted aryl. In some embodiments, $R_{19}$ is unsubstituted $C_3$-$C_{10}$heterocyclyl. In some embodiments, $R_{19}$ is substituted $C_3$-$C_{10}$heterocyclyl. In some embodiments, $R_{19}$ is unsubstituted heteroaryl. In some embodiments, $R_{19}$ is substituted heteroaryl. In some embodiments, $R_{19}$ is unsubstituted $C_3$-$C_{10}$cycloalkyl. In some embodiments, $R_{19}$ is substituted $C_3$-$C_{10}$cycloalkyl. In some embodiments, $R_{19}$ is —$PO_3WY$. In some embodiments, $R_{19}$ is —$CH_2PO_4WY$. In some embodiments, $R_{19}$ is —$CH_2PO_4Z$. In some embodiments, $R_{19}$ is —$PO_3Z$.

In some embodiments, $R_{21}$ is hydrogen. In some embodiments, $R_{21}$ is hydroxy. In some embodiments, $R_{21}$ is carboxaldehyde. In some embodiments, $R_{21}$ is unsubstituted amine. In some embodiments, $R_{21}$ is substituted amine. In some embodiments, $R_{21}$ is unsubstituted $C_1$-$C_{10}$ alkyl. In some embodiments, $R_{21}$ is unsubstituted $C_2$-$C_{10}$ alkynyl. In some embodiments, $R_{21}$ is substituted $C_2$-$C_{10}$ alkynyl. In some embodiments, $R_{21}$ is unsubstituted $C_2$-$C_{10}$ alkenyl. In some embodiments, $R_{21}$ is substituted $C_2$-$C_{10}$ alkenyl. In some embodiments, $R_{21}$ is carboxyl. In some embodiments, $R_{21}$ is unsubstituted carbohydrate. In some embodiments, $R_{21}$ is substituted carbohydrate. In some embodiments, $R_{21}$ is unsubstituted ester. In some embodiments, $R_{21}$ is substituted ester. In some embodiments, $R_{21}$ is unsubstituted acyloxy. In some embodiments, $R_{21}$ is substituted acyloxy. In some embodiments, $R_{21}$ is nitro. In some embodiments, $R_{21}$ is halogen. In some embodiments, $R_{21}$ is unsubstituted $C_1$-$C_{10}$ aliphatic acyl. In some embodiments, $R_{21}$ is substituted $C_1$-$C_{10}$ aliphatic acyl. In some embodiments, $R_{21}$ is unsubstituted $C_6$-$C_{10}$ aromatic acyl. In some embodiments, $R_{21}$ is substituted $C_6$-$C_{10}$ aromatic acyl. In some embodiments, $R_{21}$ is unsubstituted $C_6$-$C_{10}$ aralkyl acyl. In some embodiments, $R_{21}$ is substituted $C_6$-$C_{10}$ aralkyl acyl. In some embodiments, $R_{21}$ is unsubstituted $C_6$-$C_{10}$ alkylaryl acyl. In some embodiments, $R_{21}$ is substituted $C_6$-$C_{10}$ alkylaryl acyl. In some embodiments, $R_{21}$ is unsubstituted alkoxy. In some embodiments, $R_{21}$ is substituted alkoxy. In some embodiments, $R_{21}$ is unsubstituted aryl. In some embodiments, $R_{21}$ is substituted aryl. In some embodiments, $R_{21}$ is unsubstituted $C_3$-$C_{10}$heterocyclyl. In some embodiments, $R_{21}$ is substituted $C_3$-$C_{10}$heterocyclyl. In some embodiments, $R_{21}$ is unsubstituted heteroaryl. In some embodiments, $R_{21}$ is substituted heteroaryl. In some embodiments, $R_{21}$ is unsubstituted $C_3$-$C_{10}$cycloalkyl. In some embodiments, $R_{21}$ is substituted $C_3$-$C_{10}$cycloalkyl. In some embodiments, $R_{21}$ is —$OPO_3WY$. In some embodiments, $R_{21}$ is —$OCH_2PO_4WY$. In some embodiments, $R_{21}$ is —$OCH_2PO_4Z$. In some embodiments, $R_{21}$ is —$OPO_3Z$.

In some embodiments, s is an integer of 0. In some embodiments, s is an integer of 1. In some embodiments, s is an integer of 2. In some embodiments, s is an integer of 3.

In some embodiments, n is an integer of 0. In some embodiments, n is an integer of 1. In some embodiments, n is an integer of 2. In some embodiments, n is an integer of 3. In some embodiments, n is an integer of 4.

In various embodiments, W and Y are independently potassium, sodium, or lithium.

In various embodiments, Z is calcium, magnesium or iron.

In various embodiments of the invention, the phosphorylated pyrone analog is of Formulae III, IV, V, or VI as illustrated in Scheme I wherein the compound comprises at least one phosphate group.

Scheme I.
Exemplary subclasses of Formula II

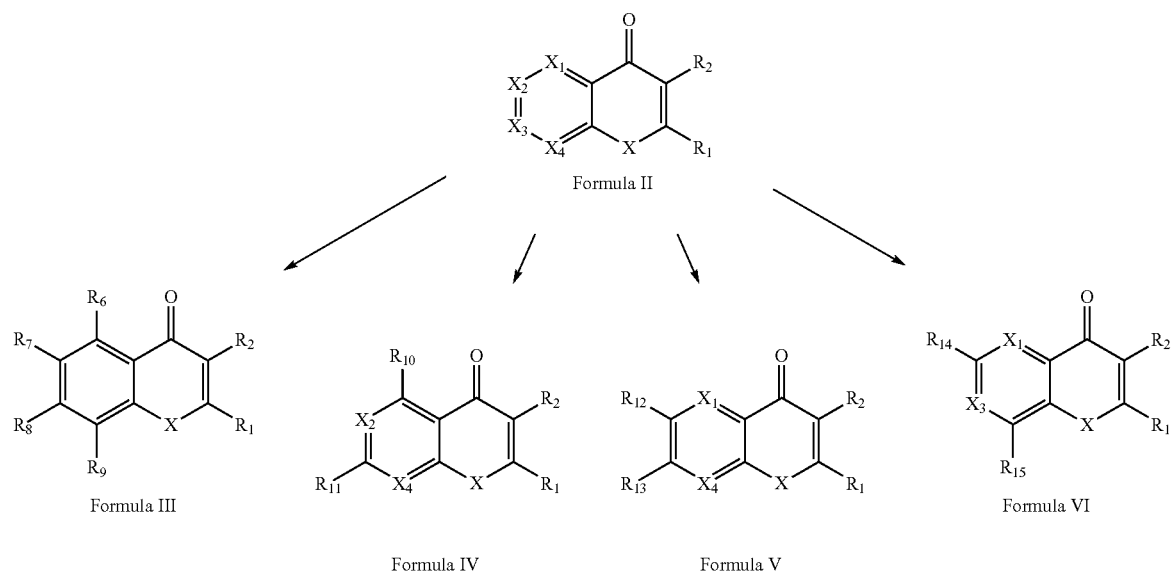

In some embodiments of the invention where the $X_1$, $X_2$, $X_3$, and $X_4$ of the compounds of Formula II are $CR_5$, the compound is of Formula III wherein the compound comprises at least one phosphate group:

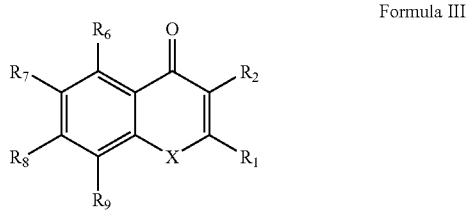

Formula III wherein X, $R_1$, $R_2$, W, Y, and Z are defined as in Formula I and Formula II;

$R_6$, $R_7$, $R_8$, and $R_9$ are independently hydrogen, hydroxyl, carboxaldehyde, amino, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$alkylaryl acyl, alkoxy, amine, aryl, $C_3$-$C_{10}$heterocyclyl, heteroaryl, $C_3$-$C_{10}$cycloalkyl, —$OPO_3WY$, —$OCH_2PO_4WY$, —$OCH_2PO_4Z$ or —$OPO_3Z$.

In some embodiments, $R_6$ is hydrogen. In some embodiments, $R_6$ is hydroxyl. In some embodiments, $R_6$ is carboxaldehyde. In some embodiments, $R_6$ is unsubstituted amine. In some embodiments, $R_6$ is substituted amine. In some embodiments, $R_6$ is unsubstituted $C_1$-$C_{10}$ alkyl. In some embodiments, $R_6$ is substituted $C_1$-$C_{10}$ alkyl. In some embodiments, $R_6$ is unsubstituted $C_2$-$C_{10}$ alkynyl. In some embodiments, $R_6$ is substituted $C_2$-$C_{10}$ alkynyl. In some embodiments, $R_6$ is unsubstituted $C_2$-$C_{10}$ alkenyl. In some embodiments, $R_6$ is substituted $C_2$-$C_{10}$ alkenyl. In some embodiments, $R_6$ is carboxyl. In some embodiments, $R_6$ is unsubstituted carbohydrate. In some embodiments, $R_6$ is substituted carbohydrate. In some embodiments, $R_6$ is unsubstituted ester. In some embodiments, $R_6$ is substituted ester. In some embodiments, $R_6$ is unsubstituted acyloxy. In some embodiments, $R_6$ is substituted acyloxy. In some embodiments, $R_6$ is nitro. In some embodiments, $R_6$ is halogen. In some embodiments, $R_6$ is unsubstituted $C_1$-$C_{10}$ aliphatic acyl. In some embodiments, $R_6$ is substituted $C_1$-$C_{10}$ aliphatic acyl. In some embodiments, $R_6$ is unsubstituted $C_6$-$C_{10}$ aromatic acyl. In some embodiments, $R_6$ is substituted $C_6$-$C_{10}$ aromatic acyl. In some embodiments, $R_6$ is unsubstituted $C_6$-$C_{10}$ aralkyl acyl. In some embodiments, $R_6$ is substituted $C_6$-$C_{10}$ aralkyl acyl. In some embodiments, $R_6$ is unsubstituted $C_6$-$C_{10}$ alkylaryl acyl. In some embodiments, $R_6$ is substituted $C_6$-$C_{10}$ alkylaryl acyl. In some embodiments, $R_6$ is unsubstituted alkoxy. In some embodiments, $R_6$ is substituted alkoxy. In some embodiments, $R_6$ is unsubstituted aryl. In some embodiments, $R_6$ is substituted aryl. In some embodiments, $R_6$ is unsubstituted $C_3$-$C_{10}$heterocyclyl. In some embodiments, $R_6$ is substituted $C_3$-$C_{10}$ heterocyclyl. In some embodiments, $R_6$ is unsubstituted heteroaryl. In some embodiments, $R_6$ is unsubstituted $C_3$-$C_{10}$cycloalkyl. In some embodiments, $R_6$ is substituted $C_3$-$C_{10}$cycloalkyl. In some embodiments, $R_6$ is —$OPO_3WY$. In some embodiments, $R_6$ is —$OCH_2PO_4WY$. In some embodiments, $R_6$ is —$OCH_2PO_4Z$. In some embodiments, $R_6$ is —$OPO_3Z$.

In some embodiments, $R_7$ is hydrogen. In some embodiments, $R_7$ is hydroxyl. In some embodiments, $R_7$ is carboxaldehyde. In some embodiments, $R_7$ is unsubstituted amine. In some embodiments, $R_7$ is substituted amine. In some embodiments, $R_7$ is unsubstituted $C_1$-$C_{10}$ alkyl. In some embodiments, $R_7$ is substituted $C_1$-$C_{10}$ alkyl. In some embodiments, $R_7$ is unsubstituted $C_2$-$C_{10}$ alkynyl. In some embodiments, $R_7$ is substituted $C_2$-$C_{10}$ alkynyl. In some embodiments, $R_7$ is unsubstituted $C_2$-$C_{10}$ alkenyl. In some embodiments, $R_7$ is substituted $C_2$-$C_{10}$ alkenyl. In some embodiments, $R_7$ is carboxyl. In some embodiments, $R_7$ is unsubstituted carbohydrate. In some embodiments, $R_7$ is substituted carbohydrate. In some embodiments, $R_7$ is unsubstituted ester. In some embodiments, $R_7$ is substituted ester. In some embodiments, $R_7$ is unsubstituted acyloxy. In some embodiments, $R_7$ is substituted acyloxy. In some embodiments, $R_7$ is nitro. In some embodiments, $R_7$ is halogen. In some embodiments, $R_7$ is unsubstituted $C_1$-$C_{10}$ aliphatic acyl. In some embodiments, $R_7$ is substituted $C_1$-$C_{10}$ aliphatic acyl. In some embodiments, $R_7$ is unsubstituted $C_6$-$C_{10}$ aromatic acyl. In some embodiments, $R_7$ is substituted $C_6$-$C_{10}$ aromatic acyl. In some embodiments, $R_7$ is unsubstituted $C_6$-$C_{10}$ aralkyl acyl. In some embodiments, $R_7$ is substituted $C_6$-$C_{10}$ aralkyl acyl. In some embodiments, $R_7$ is unsubstituted $C_6$-$C_{10}$ alkylaryl acyl. In some embodiments, $R_7$ is substituted $C_6$-$C_{10}$ alkylaryl acyl. In some embodiments, $R_7$ is unsubstituted alkoxy. In some embodiments, $R_7$ is substituted alkoxy. In some embodiments, $R_7$ is unsubstituted aryl. In some embodiments, $R_7$ is substituted aryl. In some embodiments, $R_7$ is unsubstituted $C_3$-$C_{10}$heterocyclyl. In some embodiments, $R_7$ is substituted $C_3$-$C_{10}$ heterocyclyl. In some embodiments, $R_7$ is unsubstituted heteroaryl. In some embodiments, $R_7$ is unsubstituted $C_3$-$C_{10}$cycloalkyl. In some embodiments, $R_7$ is substituted $C_3$-$C_{10}$cycloalkyl. In some embodiments, $R_7$ is —$OPO_3WY$. In some embodiments, $R_7$ is —$OCH_2PO_4WY$. In some embodiments, $R_7$ is —$OCH_2PO_4Z$. In some embodiments, $R_7$ is —$OPO_3Z$.

In some embodiments, $R_8$ is hydrogen. In some embodiments, $R_8$ is hydroxyl. In some embodiments, $R_8$ is carboxaldehyde. In some embodiments, $R_8$ is unsubstituted amine. In some embodiments, $R_8$ is substituted amine. In some embodiments, $R_8$ is unsubstituted $C_1$-$C_{10}$ alkyl. In some embodiments, $R_8$ is substituted $C_1$-$C_{10}$ alkyl. In some embodiments, $R_8$ is unsubstituted $C_2$-$C_{10}$ alkynyl. In some embodiments, $R_8$ is substituted $C_2$-$C_{10}$ alkynyl. In some embodiments, $R_8$ is unsubstituted $C_2$-$C_{10}$ alkenyl. In some embodiments, $R_8$ is substituted $C_2$-$C_{10}$ alkenyl. In some embodiments, $R_8$ is carboxyl. In some embodiments, $R_8$ is unsubstituted carbohydrate. In some embodiments, $R_8$ is substituted carbohydrate. In some embodiments, $R_8$ is unsubstituted ester. In some embodiments, $R_8$ is substituted ester. In some embodiments, $R_8$ is unsubstituted acyloxy. In some embodiments, $R_8$ is substituted acyloxy. In some embodiments, $R_8$ is nitro. In some embodiments, $R_8$ is halogen. In some embodiments, $R_8$ is unsubstituted $C_1$-$C_{10}$ aliphatic acyl. In some embodiments, $R_8$ is substituted $C_1$-$C_{10}$ aliphatic acyl. In some embodiments, $R_8$ is unsubstituted $C_6$-$C_{10}$ aromatic acyl. In some embodiments, $R_8$ is substituted $C_6$-$C_{10}$ aromatic acyl. In some embodiments, $R_8$ is unsubstituted $C_6$-$C_{10}$ aralkyl acyl. In some embodiments, $R_8$ is substituted $C_6$-$C_{10}$ aralkyl acyl. In some embodiments, $R_8$ is unsubstituted $C_6$-$C_{10}$ alkylaryl acyl. In some embodiments, $R_8$ is substituted $C_6$-$C_{10}$ alkylaryl acyl. In some embodiments, $R_8$ is unsubstituted alkoxy. In some embodiments, $R_8$ is substituted alkoxy. In some embodiments, $R_8$ is unsubstituted aryl. In some embodiments, $R_8$ is substituted aryl. In some embodiments, $R_8$ is unsubstituted $C_3$-$C_{10}$heterocyclyl. In some embodiments, $R_8$ is substituted $C_3$-$C_{10}$ heterocyclyl. In some embodiments, $R_8$ is unsubstituted heteroaryl. In some embodiments, $R_8$ is unsubstituted $C_3$-$C_{10}$cycloalkyl. In some embodiments, $R_8$ is substituted $C_3$-$C_{10}$cycloalkyl. In some embodiments, $R_8$ is —$OPO_3WY$. In some embodiments, $R_8$ is —OCH$_2$PO$_4$WY. In some embodiments, R$_8$ is —OCH$_2$PO$_4$Z. In some embodiments, R$_8$ is —OPO$_3$Z.

In some embodiments, R$_9$ is hydrogen. In some embodiments, R$_9$ is hydroxyl. In some embodiments, R$_9$ is carboxaldehyde. In some embodiments, R$_9$ is unsubstituted amine. In some embodiments, R$_9$ is substituted amine. In some embodiments, R$_9$ is unsubstituted C$_1$-C$_{10}$ alkyl. In some embodiments, R$_9$ is substituted C$_1$-C$_{10}$ alkyl. In some embodiments, R$_9$ is unsubstituted C$_2$-C$_{10}$ alkynyl. In some embodiments, R$_9$ is substituted C$_2$-C$_{10}$ alkynyl. In some embodiments, R$_9$ is unsubstituted C$_2$-C$_{10}$ alkenyl. In some embodiments, R$_9$ is substituted C$_2$-C$_{10}$ alkenyl. In some embodiments, R$_9$ is carboxyl. In some embodiments, R$_9$ is unsubstituted carbohydrate. In some embodiments, R$_9$ is substituted carbohydrate. In some embodiments, R$_9$ is unsubstituted ester. In some embodiments, R$_9$ is substituted ester. In some embodiments, R$_9$ is unsubstituted acyloxy. In some embodiments, R$_9$ is substituted acyloxy. In some embodiments, R$_9$ is nitro. In some embodiments, R$_9$ is halogen. In some embodiments, R$_9$ is unsubstituted C$_1$-C$_{10}$ aliphatic acyl. In some embodiments, R$_9$ is substituted C$_1$-C$_{10}$ aliphatic acyl. In some embodiments, R$_9$ is unsubstituted C$_6$-C$_{10}$ aromatic acyl. In some embodiments, R$_9$ is substituted C$_6$-C$_{10}$ aromatic acyl. In some embodiments, R$_9$ is unsubstituted C$_6$-C$_{10}$ aralkyl acyl. In some embodiments, R$_9$ is substituted C$_6$-C$_{10}$ aralkyl acyl. In some embodiments, R$_9$ is unsubstituted C$_6$-C$_{10}$ alkylaryl acyl. In some embodiments, R$_9$ is substituted C$_6$-C$_{10}$ alkylaryl acyl. In some embodiments, R$_9$ is unsubstituted alkoxy. In some embodiments, R$_9$ is substituted alkoxy. In some embodiments, R$_9$ is unsubstituted aryl. In some embodiments, R$_9$ is substituted aryl. In some embodiments, R$_9$ is unsubstituted C$_3$-C$_{10}$heterocyclyl. In some embodiments, R$_9$ is substituted C$_3$-C$_{10}$ heterocyclyl. In some embodiments, R$_9$ is unsubstituted heteroaryl. In some embodiments, R$_9$ is unsubstituted C$_3$-C$_{10}$cycloalkyl. In some embodiments, R$_9$ is substituted C$_3$-C$_{10}$cycloalkyl. In some embodiments, R$_9$ is —OPO$_3$WY. In some embodiments, R$_9$ is —OCH$_2$PO$_4$WY. In some embodiments, R$_9$ is —OCH$_2$PO$_4$Z. In some embodiments, R$_9$ is —OPO$_3$Z.

In various embodiments of the invention, the phosphorylated pyrone analog of Formula III is of Formula VII wherein the compound comprises at least one phosphate group:

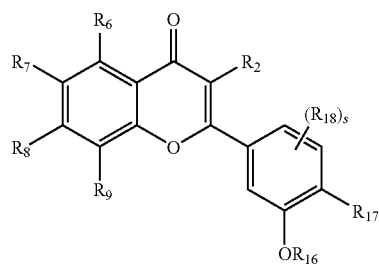

Formula VII wherein R$_2$, R$_{16}$, R$_{17}$, R$_{18}$, and s are as defined in Formula II and R$_6$, R$_7$, R$_8$, and R$_9$ are as defined in Formula III.

In other embodiments of the invention, the phosphorylated pyrone analog of Formula III is a compound of Formula VIII wherein the compound comprises at least one phosphate group:

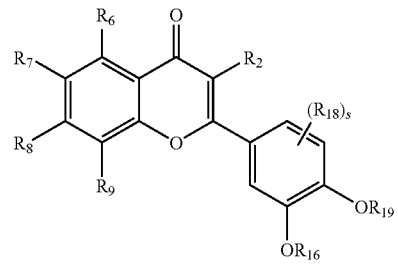

Formula VIII wherein R$_2$, R$_{16}$, R$_{18}$, R$_{19}$, and s are as defined in Formula II and R$_6$, R$_7$, R$_8$, and R$_9$ are as defined in Formula III.

In some embodiments of the invention, the phosphorylated pyrone analog of Formula II is of Formula IX wherein the compound comprises at least one phosphate group:

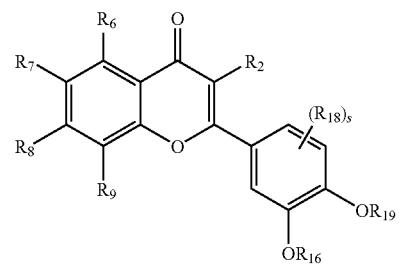

Formula IX wherein R$_2$, R$_{16}$, R$_{18}$, R$_{19}$, and s are as defined in Formula II; and R$_6$, R$_7$, R$_8$, and R$_9$ are independently hydrogen, carboxaldehyde, amino, C$_1$-C$_{10}$ alkyl, C$_2$-C$_{10}$ alkynyl, C$_2$-C$_{10}$ alkenyl, carboxyl, carbohydrate, ester, acyloxy, nitro, halogen, C$_1$-C$_{10}$ aliphatic acyl, C$_6$-C$_{10}$ aromatic acyl, C$_6$-C$_{10}$ aralkyl acyl, C$_6$-C$_{10}$alkylaryl acyl, alkoxy, amine, aryl, C$_3$-C$_{10}$heterocyclyl, heteroaryl, C$_3$-C$_{10}$cycloalkyl, —OPO$_3$WY, —OCH$_2$PO$_4$WY, —OCH$_2$PO$_4$Z or —OPO$_3$Z. In this embodiment, none of R$_6$-R$_9$ are OH.

In some embodiments, R$_6$ is hydrogen. In some embodiments, R$_6$ is carboxaldehyde. In some embodiments, R$_6$ is unsubstituted amine. In some embodiments, R$_6$ is substituted amine. In some embodiments, R$_6$ is unsubstituted C$_1$-C$_{10}$ alkyl. In some embodiments, R$_6$ is substituted C$_1$-C$_{10}$ alkyl. In some embodiments, R$_6$ is unsubstituted C$_2$-C$_{10}$ alkynyl. In some embodiments, R$_6$ is substituted C$_2$-C$_{10}$ alkynyl. In some embodiments, R$_6$ is unsubstituted C$_2$-C$_{10}$ alkenyl. In some embodiments, R$_6$ is substituted C$_2$-C$_{10}$ alkenyl. In some embodiments, R$_6$ is carboxyl. In some embodiments, R$_6$ is unsubstituted carbohydrate. In some embodiments, R$_6$ is substituted carbohydrate. In some embodiments, R$_6$ is unsubstituted ester. In some embodiments, R$_6$ is substituted ester. In some embodiments, R$_6$ is unsubstituted acyloxy. In some embodiments, R$_6$ is substituted acyloxy. In some embodiments, R$_6$ is nitro. In some embodiments, R$_6$ is halogen. In some embodiments, R$_6$ is unsubstituted C$_1$-C$_{10}$ aliphatic acyl. In some embodiments, R$_6$ is substituted C$_1$-C$_{10}$ aliphatic acyl. In some embodiments, R$_6$ is unsubstituted C$_6$-C$_{10}$ aromatic acyl. In some embodiments, R$_6$ is substituted C$_6$-C$_{10}$ aromatic acyl. In some embodiments, R$_6$ is unsubstituted C$_6$-C$_{10}$ aralkyl acyl. In some embodiments, R$_6$ is substituted C$_6$-C$_{10}$ aralkyl acyl. In some embodiments, R$_6$ is unsubstituted C$_6$-C$_{10}$ alkylaryl acyl. In some embodiments, R$_6$ is substituted C$_6$-C$_{10}$ alkylaryl acyl. In some embodiments, R$_6$ is unsubstituted alkoxy. In some embodiments, $R_6$ is substituted alkoxy. In some embodiments, $R_6$ is unsubstituted aryl. In some embodiments, $R_6$ is substituted aryl. In some embodiments, $R_6$ is unsubstituted $C_3$-$C_{10}$heterocyclyl. In some embodiments, $R_6$ is substituted $C_3$-$C_{10}$heterocyclyl. In some embodiments, $R_6$ is unsubstituted heteroaryl. In some embodiments, $R_6$ is unsubstituted $C_3$-$C_{10}$cycloalkyl. In some embodiments, $R_6$ is substituted $C_3$-$C_{10}$cycloalkyl. In some embodiments, $R_6$ is —$OPO_3WY$. In some embodiments, $R_6$ is —$OCH_2PO_4WY$. In some embodiments, $R_6$ is —$OCH_2PO_4Z$. In some embodiments, $R_6$ is —$OPO_3Z$.

In some embodiments, $R_7$ is hydrogen. In some embodiments, $R_7$ is carboxaldehyde. In some embodiments, $R_7$ is unsubstituted amine. In some embodiments, $R_7$ is substituted amine. In some embodiments, $R_7$ is unsubstituted $C_1$-$C_{10}$ alkyl. In some embodiments, $R_7$ is substituted $C_1$-$C_{10}$ alkyl. In some embodiments, $R_7$ is unsubstituted $C_2$-$C_{10}$ alkynyl. In some embodiments, $R_7$ is substituted $C_2$-$C_{10}$ alkynyl. In some embodiments, $R_7$ is unsubstituted $C_2$-$C_{10}$ alkenyl. In some embodiments, $R_7$ is substituted $C_2$-$C_{10}$ alkenyl. In some embodiments, $R_7$ is carboxyl. In some embodiments, $R_7$ is unsubstituted carbohydrate. In some embodiments, $R_7$ is substituted carbohydrate. In some embodiments, $R_7$ is unsubstituted ester. In some embodiments, $R_7$ is substituted ester. In some embodiments, $R_7$ is unsubstituted acyloxy. In some embodiments, $R_7$ is substituted acyloxy. In some embodiments, $R_7$ is nitro. In some embodiments, $R_7$ is halogen. In some embodiments, $R_7$ is unsubstituted $C_1$-$C_{10}$ aliphatic acyl. In some embodiments, $R_7$ is substituted $C_1$-$C_{10}$ aliphatic acyl. In some embodiments, $R_7$ is unsubstituted $C_6$-$C_{10}$ aromatic acyl. In some embodiments, $R_7$ is substituted $C_6$-$C_{10}$ aromatic acyl. In some embodiments, $R_7$ is unsubstituted $C_6$-$C_{10}$ aralkyl acyl. In some embodiments, $R_7$ is substituted $C_6$-$C_{10}$ aralkyl acyl. In some embodiments, $R_7$ is unsubstituted $C_6$-$C_{10}$ alkylaryl acyl. In some embodiments, $R_7$ is substituted $C_6$-$C_{10}$ alkylaryl acyl. In some embodiments, $R_7$ is unsubstituted alkoxy. In some embodiments, $R_7$ is substituted alkoxy. In some embodiments, $R_7$ is unsubstituted aryl. In some embodiments, $R_7$ is substituted aryl. In some embodiments, $R_7$ is unsubstituted $C_3$-$C_{10}$heterocyclyl. In some embodiments, $R_7$ is substituted $C_3$-$C_{10}$heterocyclyl. In some embodiments, $R_7$ is unsubstituted heteroaryl. In some embodiments, $R_7$ is unsubstituted $C_3$-$C_{10}$cycloalkyl. In some embodiments, $R_7$ is substituted $C_3$-$C_{10}$cycloalkyl. In some embodiments, $R_7$ is —$OPO_3WY$. In some embodiments, $R_7$ is —$OCH_2PO_4WY$. In some embodiments, $R_7$ is —$OCH_2PO_4Z$. In some embodiments, $R_7$ is —$OPO_3Z$.

In some embodiments, $R_8$ is hydrogen. In some embodiments, $R_8$ is hydroxyl. In some embodiments, $R_8$ is carboxaldehyde. In some embodiments, $R_8$ is unsubstituted amine. In some embodiments, $R_8$ is substituted amine. In some embodiments, $R_8$ is unsubstituted $C_1$-$C_{10}$ alkyl. In some embodiments, $R_8$ is substituted $C_1$-$C_{10}$ alkyl. In some embodiments, $R_8$ is unsubstituted $C_2$-$C_{10}$ alkynyl. In some embodiments, $R_8$ is substituted $C_2$-$C_{10}$ alkynyl. In some embodiments, $R_8$ is unsubstituted $C_2$-$C_{10}$ alkenyl. In some embodiments, $R_8$ is substituted $C_2$-$C_{10}$ alkenyl. In some embodiments, $R_8$ is carboxyl. In some embodiments, $R_8$ is unsubstituted carbohydrate. In some embodiments, $R_8$ is substituted carbohydrate. In some embodiments, $R_8$ is unsubstituted ester. In some embodiments, $R_8$ is substituted ester. In some embodiments, $R_8$ is unsubstituted acyloxy. In some embodiments, $R_8$ is substituted acyloxy. In some embodiments, $R_8$ is nitro. In some embodiments, $R_8$ is halogen. In some embodiments, $R_8$ is unsubstituted $C_1$-$C_{10}$ aliphatic acyl. In some embodiments, $R_8$ is substituted $C_1$-$C_{10}$ aliphatic acyl. In some embodiments, $R_8$ is unsubstituted $C_6$-$C_{10}$ aromatic acyl. In some embodiments, $R_8$ is substituted $C_6$-$C_{10}$ aromatic acyl. In some embodiments, $R_8$ is unsubstituted $C_6$-$C_{10}$ aralkyl acyl. In some embodiments, $R_8$ is substituted $C_6$-$C_{10}$ aralkyl acyl. In some embodiments, $R_8$ is unsubstituted $C_6$-$C_{10}$ alkylaryl acyl. In some embodiments, $R_8$ is substituted $C_6$-$C_{10}$ alkylaryl acyl. In some embodiments, $R_8$ is unsubstituted alkoxy. In some embodiments, $R_8$ is substituted alkoxy. In some embodiments, $R_8$ is unsubstituted aryl. In some embodiments, $R_8$ is substituted aryl. In some embodiments, $R_8$ is unsubstituted $C_3$-$C_{10}$heterocyclyl. In some embodiments, $R_8$ is substituted $C_3$-$C_{10}$ heterocyclyl. In some embodiments, $R_8$ is unsubstituted heteroaryl. In some embodiments, $R_8$ is unsubstituted $C_3$-$C_{10}$cycloalkyl. In some embodiments, $R_8$ is substituted $C_3$-$C_{10}$cycloalkyl. In some embodiments, $R_8$ is —$OPO_3WY$. In some embodiments, $R_8$ is —$OCH_2PO_4WY$. In some embodiments, $R_8$ is —$OCH_2PO_4Z$. In some embodiments, $R_8$ is —$OPO_3Z$.

In some embodiments, $R_9$ is hydrogen. In some embodiments, $R_9$ is carboxaldehyde. In some embodiments, $R_9$ is unsubstituted amine. In some embodiments, $R_9$ is substituted amine. In some embodiments, $R_9$ is unsubstituted $C_1$-$C_{10}$ alkyl. In some embodiments, $R_9$ is substituted $C_1$-$C_{10}$ alkyl. In some embodiments, $R_9$ is unsubstituted $C_2$-$C_{10}$ alkynyl. In some embodiments, $R_9$ is substituted $C_2$-$C_{10}$ alkynyl. In some embodiments, $R_9$ is unsubstituted $C_2$-$C_{10}$ alkenyl. In some embodiments, $R_9$ is substituted $C_2$-$C_{10}$ alkenyl. In some embodiments, $R_9$ is carboxyl. In some embodiments, $R_9$ is unsubstituted carbohydrate. In some embodiments, $R_9$ is substituted carbohydrate. In some embodiments, $R_9$ is unsubstituted ester. In some embodiments, $R_9$ is substituted ester. In some embodiments, $R_9$ is unsubstituted acyloxy. In some embodiments, $R_9$ is substituted acyloxy. In some embodiments, $R_9$ is nitro. In some embodiments, $R_9$ is halogen. In some embodiments, $R_9$ is unsubstituted $C_1$-$C_{10}$ aliphatic acyl. In some embodiments, $R_9$ is substituted $C_1$-$C_{10}$ aliphatic acyl. In some embodiments, $R_9$ is unsubstituted $C_6$-$C_{10}$ aromatic acyl. In some embodiments, $R_9$ is substituted $C_6$-$C_{10}$ aromatic acyl. In some embodiments, $R_9$ is unsubstituted $C_6$-$C_{10}$ aralkyl acyl. In some embodiments, $R_9$ is substituted $C_6$-$C_{10}$ aralkyl acyl. In some embodiments, $R_9$ is unsubstituted $C_6$-$C_{10}$ alkylaryl acyl. In some embodiments, $R_9$ is substituted $C_6$-$C_{10}$ alkylaryl acyl. In some embodiments, $R_9$ is unsubstituted alkoxy. In some embodiments, $R_9$ is substituted alkoxy. In some embodiments, $R_9$ is unsubstituted aryl. In some embodiments, $R_9$ is substituted aryl. In some embodiments, $R_9$ is unsubstituted $C_3$-$C_{10}$heterocyclyl. In some embodiments, $R_9$ is substituted $C_3$-$C_{10}$heterocyclyl. In some embodiments, $R_9$ is unsubstituted heteroaryl. In some embodiments, $R_9$ is unsubstituted $C_3$-$C_{10}$cycloalkyl. In some embodiments, $R_9$ is substituted $C_3$-$C_{10}$cycloalkyl. In some embodiments, $R_9$ is —$OPO_3WY$. In some embodiments, $R_9$ is —$OCH_2PO_4WY$. In some embodiments, $R_9$ is —$OCH_2PO_4Z$. In some embodiments, $R_9$ is —$OPO_3Z$.

In some embodiments of the invention, the phosphorylated pyrone analog of Formula III is of Formula X wherein the compound comprises at least one phosphate group:

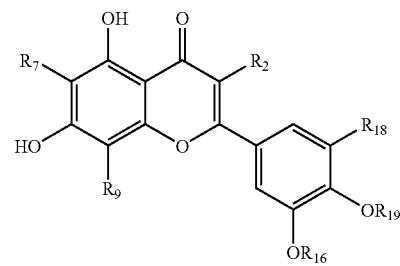

Formula X wherein $R_2$, $R_{16}$, $R_{18}$, and $R_{19}$ are as defined in Formula II and $R_7$ and $R_9$ are as defined in Formula III.

In other embodiments of the invention, the phosphorylated pyrone analog of Formula III is of Formula XI wherein the compound comprises at least one phosphate group:

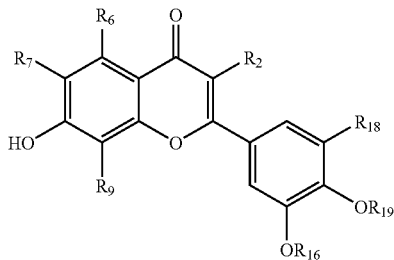

Formula XI wherein $R_2$, $R_{16}$, $R_{18}$, and $R_{19}$ are as defined in Formula II and $R_6$, $R_7$, and $R_9$ are as defined in Formula III.

In some embodiments of the invention, compounds of the following Formulae VIII-A, VIII-B, and VIII-C, are useful in the methods of the invention, where each instance of $R_c$ and $R_d$ is independently hydrogen, —OPO$_3$WY, —OPO$_3$Z, —OCH$_2$—OPOWY, or —OCH$_2$—OPO$_3$Z, where W and Y are hydrogen, methyl, ethyl, alkyl, carbohydrate, lithium, sodium or potassium and Z is calcium, magnesium or iron.

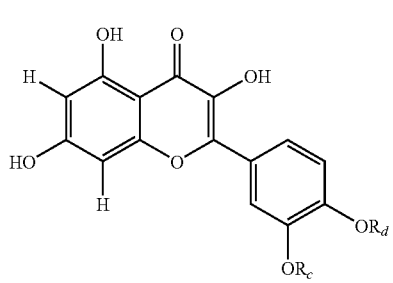

Formula VIII-A

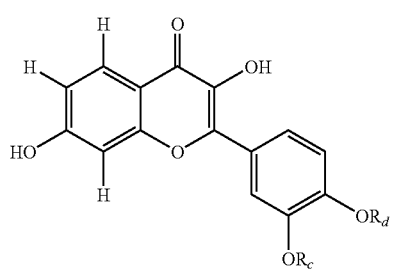

Formula VIII-B

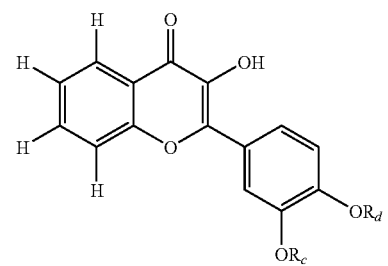

Formula VIII-C

In some embodiments of the invention, for a compound of Formulae VIII-A, VIII-B, or VIII-C, wherein the compound comprises at least one phosphate group are used. In some embodiments of the invention, for a compound of Formulae VIII-A, VIII-B, or VIII-C, $R_c$ and $R_d$ are hydrogen. In some embodiments of the invention, for a compound of Formulae VIII-A, VIII-B, or VIII-C, $R_c$ is —OPO$_3$WY and $R_d$ is hydrogen. In some embodiments of the invention, for a compound of Formulae VIII-A, VIII-B, or VIII-C, $R_c$ is —OPO$_3$WY and $R_d$ is —OPO$_3$WY. In some embodiments of the invention, for a compound of Formulae VIII-A, VIII-B, or VIII-C, $R_c$ is a mixture of hydrogen and —OPO$_3$WY and $R_d$ is —OPO$_3$WY. In some embodiments of the invention, for a compound of Formulae VIII-A, VIII-B, or VIII-C, $R_c$ is hydrogen and $R_d$ is a mixture of hydrogen and —OPO$_3$Z. In some embodiments of the invention, for a compound of Formulae VIII-A, VIII-B, or VIII-C, $R_c$ is —OPO$_3$Z and $R_d$ is hydrogen. In some embodiments of the invention, for a compound of Formulae VIII-A, VIII-B, or VIII-C, $R_c$ is —OPO$_3$Z and $R_d$ is —OPO$_3$Z. In some embodiments of the invention, for a compound of Formulae VIII-A, VIII-B, or VIII-C, $R_c$ is a mixture of hydrogen and —OPO$_3$Z and $R_d$ is —OPO$_3$Z. In some embodiments of the invention, for a compound of Formulae VIII-A, VIII-B, or VIII-C, $R_c$ is hydrogen and $R_d$ is a mixture of hydrogen and —OPO$_3$Z. In some embodiments of the invention, for a compound of Formulae VIII-A, VIII-B, or VIII-C, $R_c$ is —CH$_2$—OPO$_3$Z and $R_d$ is hydrogen. In some embodiments of the invention, for a compound of Formulae VIII-A, VIII-B, or VIII-C, $R_c$ is —CH$_2$OPO$_3$Z and $R_d$ is —CH$_2$OPO$_3$Z. In some embodiments of the invention, for a compound of Formulae VIII-A, VIII-B, or VIII-C, $R_c$ is a mixture of hydrogen and —CH$_2$OPO$_3$Z and $R_d$ is —CH$_2$OPO$_3$Z. In some embodiments of the invention, for a compound of Formulae VIII-A, VIII-B, or VIII-C, $R_c$ is hydrogen and $R_d$ is a mixture of hydrogen and —CH$_2$OPO$_3$Z.

In other embodiments of the invention, the phosphorylated pyrone analog of Formula III is of Formula XII wherein the compound comprises at least one phosphate group:

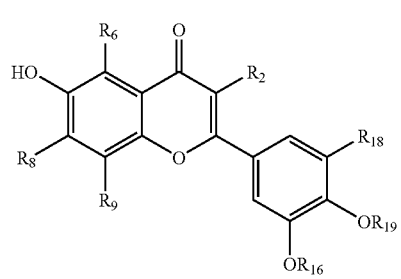

Formula XII wherein $R_2$, $R_{16}$, $R_{18}$, and $R_{19}$ are as defined in Formula II and $R_6$, $R_8$, and $R_9$ are as defined in Formula III.

In other embodiments of the invention, the phosphorylated pyrone analog of Formula III is of Formula XIII wherein the compound comprises at least one phosphate group:

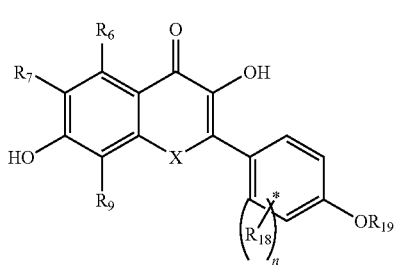

Formula XIII wherein X, $R_{18}$, and $R_{19}$ are as defined in Formula II and $R_6$, $R_7$, and $R_9$ are as defined in Formula III.

In some embodiments, the phosphorylated pyrone analog of Formula III is of Formula XIV wherein the compound comprises at least one phosphate group:

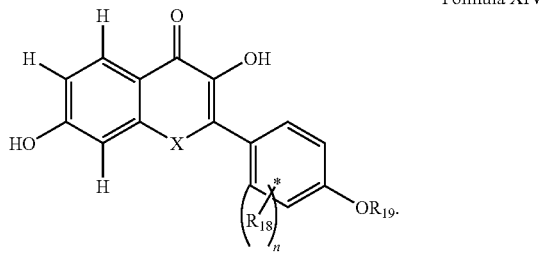

Formula XIV

In some embodiments, the phosphorylated pyrone analog of Formula III is of Formula XV wherein the compound comprises at least one phosphate group:

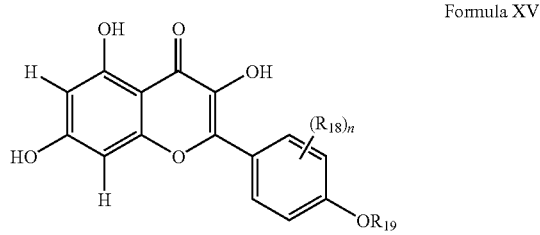

Formula XV wherein $R_{18}$, $R_{19}$, and n are as defined in Formula II.

In some embodiments, the phosphorylated pyrone analog of Formula III is of Formula XVI wherein the compound comprises at least one phosphate group:

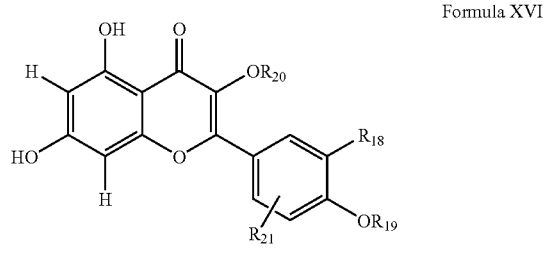

Formula XVI wherein $R_{18}$, $R_{19}$, $R_{21}$, and n are as defined in Formula II;

$R_{20}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$heterocyclyl, heteroaryl, optionally substituted $C_3$-$C_{10}$cycloalkyl, —$PO_3WY$, —$CH_2PO_4WY$, —$CH_2PO_4Z$ or —$PO_3Z$; and W and Y are independently hydrogen, methyl, ethyl, alkyl, carbohydrate, or a cation, and Z is a multivalent cation.

In some embodiments, $R_{20}$ is hydrogen. In some embodiments, $R_{20}$ is unsubstituted $C_1$-$C_{10}$ alkyl. In some embodiments, $R_{20}$ is substituted $C_1$-$C_{10}$ alkyl. In some embodiments, $R_{20}$ is unsubstituted $C_2$-$C_{10}$ alkynyl. In some embodiments, $R_{20}$ is substituted $C_2$-$C_{10}$ alkynyl. In some embodiments, $R_{20}$ is unsubstituted $C_2$-$C_{10}$ alkenyl. In some embodiments, $R_{20}$ is substituted $C_2$-$C_{10}$ alkenyl. In some embodiments, $R_{20}$ is unsubstituted carbohydrate. In some embodiments, $R_{20}$ is substituted carbohydrate. In some embodiments, $R_{20}$ is unsubstituted $C_1$-$C_{10}$ aliphatic acyl. In some embodiments, $R_{20}$ is substituted $C_1$-$C_{10}$ aliphatic acyl. In some embodiments, $R_{20}$ is unsubstituted $C_6$-$C_{10}$ aromatic acyl. In some embodiments, $R_{20}$ is substituted $C_6$-$C_{10}$ aromatic acyl. In some embodiments, $R_{20}$ is unsubstituted $C_6$-$C_{10}$ aralkyl acyl. In some embodiments, $R_{20}$ is substituted $C_6$-$C_{10}$ aralkyl acyl. In some embodiments, $R_{20}$ is unsubstituted $C_6$-$C_{10}$ alkylaryl acyl. In some embodiments, $R_{20}$ is substituted $C_6$-$C_{10}$ alkylaryl acyl. In some embodiments, $R_{20}$ is unsubstituted aryl. In some embodiments, $R_{20}$ is substituted aryl. In some embodiments, $R_{20}$ is unsubstituted $C_3$-$C_{10}$heterocyclyl. In some embodiments, $R_{20}$ is substituted $C_3$-$C_{10}$heterocyclyl. In some embodiments, $R_{20}$ is unsubstituted heteroaryl. In some embodiments, $R_{20}$ is substituted heteroaryl. In some embodiments, $R_{20}$ is unsubstituted $C_3$-$C_{10}$cycloalkyl. In some embodiments, $R_{20}$ is substituted $C_3$-$C_{10}$cycloalkyl. In some embodiments, $R_{20}$ is —$PO_3WY$. In some embodiments, $R_{20}$ is —$CH_2PO_4WY$. In some embodiments, $R_{20}$ is —$CH_2PO_4Z$. In some embodiments, $R_{20}$ is —$PO_3Z$.

In some embodiments, the phosphorylated pyrone analog of Formula III is of Formula XVII wherein the compound comprises at least one phosphate group:

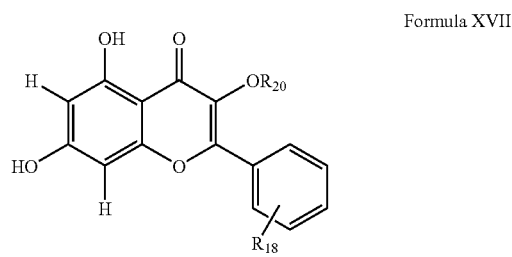

Formula XVII wherein $R_{18}$ is as defined in Formula II; and $R_{20}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$heterocyclyl, heteroaryl, optionally substituted $C_3$-$C_{10}$cycloalkyl, —$PO_3WY$, —$CH_2PO_4WY$, —$CH_2PO_4Z$ or —$PO_3Z$.

In some embodiments, $R_{20}$ is hydrogen. In some embodiments, $R_{20}$ is unsubstituted $C_1$-$C_{10}$ alkyl. In some embodiments, $R_{20}$ is substituted $C_1$-$C_{10}$ alkyl. In some embodiments, $R_{20}$ is unsubstituted $C_2$-$C_{10}$ alkynyl. In some embodiments, $R_{20}$ is substituted $C_2$-$C_{10}$ alkynyl. In some embodiments, $R_{20}$ is unsubstituted $C_2$-$C_{10}$ alkenyl. In some embodiments, $R_{20}$ is substituted $C_2$-$C_{10}$ alkenyl. In some embodiments, $R_{20}$ is unsubstituted carbohydrate. In some embodiments, $R_{20}$ is substituted carbohydrate. In some embodiments, $R_{20}$ is unsubstituted $C_1$-$C_{10}$ aliphatic acyl. In some embodiments, $R_{20}$ is substituted $C_1$-$C_{10}$ aliphatic acyl. In some embodiments, $R_{20}$ is unsubstituted $C_6$-$C_{10}$ aromatic acyl. In some embodiments, $R_{20}$ is substituted $C_6$-$C_{10}$ aromatic acyl. In some embodiments, $R_{20}$ is unsubstituted $C_6$-$C_{10}$ aralkyl acyl. In some embodiments, $R_{20}$ is substituted $C_6$-$C_{10}$ aralkyl acyl. In some embodiments, $R_{20}$ is unsubstituted $C_6$-$C_{10}$ alkylaryl acyl. In some embodiments, $R_{20}$ is substituted $C_6$-$C_{10}$ alkylaryl acyl. In some embodiments, $R_{20}$ is unsubstituted aryl. In some embodiments, $R_{20}$ is substituted aryl. In some embodiments, $R_{20}$ is unsubstituted $C_3$-$C_{10}$heterocyclyl. In some embodiments, $R_{20}$ is substituted $C_3$-$C_{10}$heterocyclyl. In some embodiments, $R_{20}$ is unsubstituted heteroaryl. In some embodiments, $R_{20}$ is substituted heteroaryl. In some embodiments, $R_{20}$ is unsubstituted $C_3$-$C_{10}$cycloalkyl. In some embodiments, $R_{20}$ is substituted $C_3$-$C_{10}$cycloalkyl. In some embodiments, $R_{20}$ is —$PO_3WY$. In some embodiments, $R_{20}$ is —$CH_2PO_4WY$. In some embodiments, $R_{20}$ is —$CH_2PO_4Z$. In some embodiments, $R_{20}$ is —$PO_3Z$.

In some embodiments, the phosphorylated pyrone analog of Formula III is of Formula XVIII wherein the compound comprises at least one phosphate group:

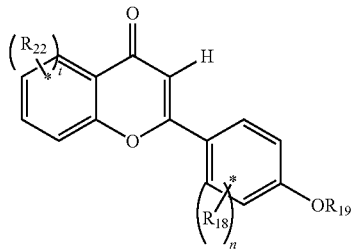

Formula XVIII wherein $R_{18}$ and $R_{19}$ are as defined in Formula II;

wherein each instance of $R_{22}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$; and t is an integer of 0, 1, 2, 3, or 4

In some embodiments, $R_{22}$ is hydrogen. In some embodiments, $R_{22}$ is hydroxy. In some embodiments, $R_{22}$ is carboxaldehyde. In some embodiments, $R_{22}$ is unsubstituted amine. In some embodiments, $R_{22}$ is substituted amine. In some embodiments, $R_{22}$ is unsubstituted $C_1$-$C_{10}$ alkyl. In some embodiments, $R_{22}$ is unsubstituted $C_2$-$C_{10}$ alkynyl. In some embodiments, $R_{22}$ is substituted $C_2$-$C_{10}$ alkynyl. In some embodiments, $R_{22}$ is unsubstituted $C_2$-$C_{10}$ alkenyl. In some embodiments, $R_{22}$ is substituted $C_2$-$C_{10}$ alkenyl. In some embodiments, $R_{22}$ is carboxyl. In some embodiments, $R_{22}$ is unsubstituted carbohydrate. In some embodiments, $R_{22}$ is substituted carbohydrate. In some embodiments, $R_{22}$ is unsubstituted ester. In some embodiments, $R_{22}$ is substituted ester. In some embodiments, $R_{22}$ is unsubstituted acyloxy. In some embodiments, $R_{22}$ is substituted acyloxy. In some embodiments, $R_{22}$ is nitro. In some embodiments, $R_{22}$ is halogen. In some embodiments, $R_{22}$ is unsubstituted $C_1$-$C_{10}$ aliphatic acyl. In some embodiments, $R_{22}$ is substituted $C_1$-$C_{10}$ aliphatic acyl. In some embodiments, $R_{22}$ is unsubstituted $C_6$-$C_{10}$ aromatic acyl. In some embodiments, $R_{22}$ is substituted $C_6$-$C_{10}$ aromatic acyl. In some embodiments, $R_{22}$ is unsubstituted $C_6$-$C_{10}$ aralkyl acyl. In some embodiments, $R_{22}$ is substituted $C_6$-$C_{10}$ aralkyl acyl. In some embodiments, $R_{22}$ is unsubstituted $C_6$-$C_{10}$ alkylaryl acyl. In some embodiments, $R_{22}$ is substituted $C_6$-$C_{10}$ alkylaryl acyl. In some embodiments, $R_{22}$ is unsubstituted alkoxy. In some embodiments, $R_{22}$ is substituted alkoxy. In some embodiments, $R_{22}$ is unsubstituted aryl. In some embodiments, $R_{22}$ is substituted aryl. In some embodiments, $R_{18}$ is unsubstituted $C_3$-$C_{10}$heterocyclyl. In some embodiments, $R_{22}$ is substituted $C_3$-$C_{10}$heterocyclyl. In some embodiments, $R_{22}$ is unsubstituted heteroaryl. In some embodiments, $R_{22}$ is unsubstituted $C_3$-$C_{10}$cycloalkyl. In some embodiments, $R_{22}$ is substituted $C_3$-$C_{10}$cycloalkyl. In some embodiments, $R_{22}$ is —$OPO_3WY$.

In some embodiments, $R_{22}$ is —$OCH_2PO_4WY$. In some embodiments, $R_{22}$ is —$OCH_2PO_4Z$. In some embodiments, $R_{22}$ is —$OPO_3Z$.

In some embodiments, t is an integer of 0. In some embodiments, t is an integer of 1. In some embodiments, t is an integer of 2. In some embodiments, t is an integer of 3. In some embodiments, t is an integer of 4.

In some embodiments, the phosphorylated pyrone analog of Formula III is of Formula XIX wherein the compound comprises at least one phosphate group:

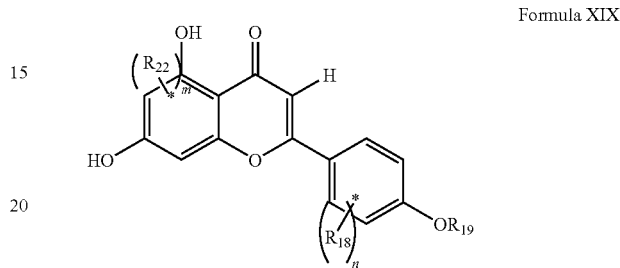

Formula XIX wherein $R_{18}$ and $R_{19}$ are as defined in Formula II;

wherein each instance of $R_{22}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$; and m is an integer of 0, 1, or 2.

In some embodiments, m is an integer of 0. In some embodiments, m is an integer of 1. In some embodiments, m is an integer of 2.

In some embodiments, the phosphorylated pyrone analog of Formula III is of Formula XX wherein the compound comprises at least one phosphate group:

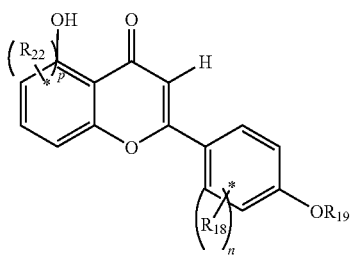

Formula XX wherein $R_{18}$ and $R_{19}$ are as defined in Formula II;

wherein each instance of $R_{22}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$; and p is an integer of 0, 1, 2 or 3.

In some embodiments, $R_{22}$ is hydrogen. In some embodiments, $R_{22}$ is hydroxy. In some embodiments, $R_{22}$ is carboxaldehyde. In some embodiments, $R_{22}$ is unsubstituted amine. In some embodiments, $R_{22}$ is substituted amine. In some embodiments, $R_{22}$ is unsubstituted $C_1$-$C_{10}$ alkyl. In some embodiments, $R_{22}$ is unsubstituted $C_2$-$C_{10}$ alkynyl. In some embodiments, $R_{22}$ is substituted $C_2$-$C_{10}$ alkynyl. In some embodiments, $R_{22}$ is unsubstituted $C_2$-$C_{10}$ alkenyl. In some embodiments, $R_{22}$ is substituted $C_2$-$C_{10}$ alkenyl. In some embodiments, $R_{22}$ is carboxyl. In some embodiments, $R_{22}$ is unsubstituted carbohydrate. In some embodiments, $R_{22}$ is substituted carbohydrate. In some embodiments, $R_{22}$ is unsubstituted ester. In some embodiments, $R_{22}$ is substituted ester. In some embodiments, $R_{22}$ is unsubstituted acyloxy. In some embodiments, $R_{22}$ is substituted acyloxy. In some embodiments, $R_{22}$ is nitro. In some embodiments, $R_{22}$ is halogen. In some embodiments, $R_{22}$ is unsubstituted $C_1$-$C_{10}$ aliphatic acyl. In some embodiments, $R_{22}$ is substituted $C_1$-$C_{10}$ aliphatic acyl. In some embodiments, $R_{22}$ is unsubstituted $C_6$-$C_{10}$ aromatic acyl. In some embodiments, $R_{22}$ is substituted $C_6$-$C_{10}$ aromatic acyl. In some embodiments, $R_{22}$ is unsubstituted $C_6$-$C_{10}$ aralkyl acyl. In some embodiments, $R_{22}$ is substituted $C_6$-$C_{10}$ aralkyl acyl. In some embodiments, $R_{22}$ is unsubstituted $C_6$-$C_{10}$ alkylaryl acyl. In some embodiments, $R_{22}$ is substituted $C_6$-$C_{10}$ alkylaryl acyl. In some embodiments, $R_{22}$ is unsubstituted alkoxy. In some embodiments, $R_{22}$ is substituted alkoxy. In some embodiments, $R_{22}$ is unsubstituted aryl. In some embodiments, $R_{22}$ is substituted aryl. In some embodiments, $R_{18}$ is unsubstituted $C_3$-$C_{10}$heterocyclyl. In some embodiments, $R_{22}$ is substituted $C_3$-$C_{10}$heterocyclyl. In some embodiments, $R_{22}$ is unsubstituted heteroaryl. In some embodiments, $R_{22}$ is substituted heteroaryl. In some embodiments, $R_{22}$ is unsubstituted $C_3$-$C_{10}$cycloalkyl. In some embodiments, $R_{22}$ is substituted $C_3$-$C_{10}$cycloalkyl. In some embodiments, $R_{22}$ is —OPO$_3$WY. In some embodiments, $R_{22}$ is —OCH$_2$PO$_4$WY. In some embodiments, $R_{22}$ is —OCH$_2$PO$_4$Z. In some embodiments, $R_{22}$ is —OPO$_3$Z.

In some embodiments, p is an integer of 0. In some embodiments, p is an integer of 1. In some embodiments, p is an integer of 2. In some embodiments, p is an integer of 3.

In some embodiments, the phosphorylated pyrone analog of Formula III is of Formula XXI wherein the compound comprises at least one phosphate group:

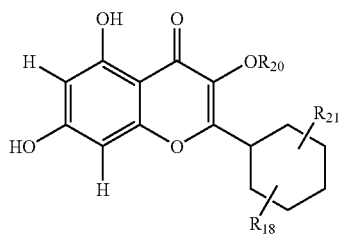

Formula XXI wherein $R_{18}$ and $R_{21}$ as defined in Formula II; and $R_{20}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$heterocyclyl, heteroaryl, optionally substituted $C_3$-$C_{10}$cycloalkyl, —PO$_3$WY, —CH$_2$PO$_4$WY, —CH$_2$PO$_4$Z or —PO$_3$Z.

In some embodiments, $R_{20}$ is hydrogen. In some embodiments, $R_{20}$ is unsubstituted $C_1$-$C_{10}$ alkyl. In some embodiments, $R_{20}$ is substituted $C_1$-$C_{10}$ alkyl. In some embodiments, $R_{20}$ is unsubstituted $C_2$-$C_{10}$ alkynyl. In some embodiments, $R_{20}$ is substituted $C_2$-$C_{10}$ alkynyl. In some embodiments, $R_{20}$ is unsubstituted $C_2$-$C_{10}$ alkenyl. In some embodiments, $R_{20}$ is substituted $C_2$-$C_{10}$ alkenyl. In some embodiments, $R_{20}$ is unsubstituted carbohydrate. In some embodiments, $R_{20}$ is substituted carbohydrate. In some embodiments, $R_{20}$ is unsubstituted $C_1$-$C_{10}$ aliphatic acyl. In some embodiments, $R_{20}$ is substituted $C_1$-$C_{10}$ aliphatic acyl. In some embodiments, $R_{20}$ is unsubstituted $C_6$-$C_{10}$ aromatic acyl. In some embodiments, $R_{20}$ is substituted $C_6$-$C_{10}$ aromatic acyl. In some embodiments, $R_{20}$ is unsubstituted $C_6$-$C_{10}$ aralkyl acyl. In some embodiments, $R_{20}$ is substituted $C_6$-$C_{10}$ aralkyl acyl. In some embodiments, $R_{20}$ is unsubstituted $C_6$-$C_{10}$ alkylaryl acyl. In some embodiments, $R_{20}$ is substituted $C_6$-$C_{10}$ alkylaryl acyl. In some embodiments, $R_{20}$ is unsubstituted aryl. In some embodiments, $R_{20}$ is substituted aryl. In some embodiments, $R_{20}$ is unsubstituted $C_3$-$C_{10}$heterocyclyl. In some embodiments, $R_{20}$ is substituted $C_3$-$C_{10}$heterocyclyl. In some embodiments, $R_{20}$ is unsubstituted heteroaryl. In some embodiments, $R_{20}$ is substituted heteroaryl. In some embodiments, $R_{20}$ is unsubstituted $C_3$-$C_{10}$cycloalkyl. In some embodiments, $R_{20}$ is substituted $C_3$-$C_{10}$cycloalkyl. In some embodiments, $R_{20}$ is —PO$_3$WY. In some embodiments, $R_{20}$ is —CH$_2$PO$_4$WY. In some embodiments, $R_{20}$ is —CH$_2$PO$_4$Z. In some embodiments, $R_{20}$ is —PO$_3$Z.

In some embodiments, the phosphorylated pyrone analog of Formula III is of Formula XXII wherein the compound comprises at least one phosphate group:

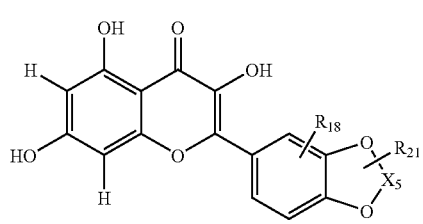

Formula XXII wherein $R_{18}$ and $R_{21}$ are as defined in Formula II;

wherein $X_5$ is a $C_1$ to $C_4$ group, optionally interrupted by O, S, NR$_{23}$, or NR$_{23}$R$_{23}$ as valency permits, forming a ring which is aromatic or nonaromatic;

each instance of $R_{23}$ is independently hydrogen, $C_1$-$C_{10}$ alkyl, $C_2$-$C_{10}$ alkynyl, $C_2$-$C_{10}$ alkenyl, carbohydrate, acyloxy, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, aryl, heteroaryl, $C_5$-$C_{10}$heterocyclyl, $C_3$-$C_{10}$cycloalkyl, —PO$_3$WY, —CH$_2$PO$_4$WY, —CH$_2$PO$_4$Z or —PO$_3$Z.

In some embodiments, $R_{23}$ is hydrogen. In some embodiments, $R_{23}$ is unsubstituted $C_1$-$C_{10}$ alkyl. In some embodiments, $R_{23}$ is substituted $C_1$-$C_{10}$ alkyl. In some embodiments, $R_{23}$ is unsubstituted $C_2$-$C_{10}$ alkynyl. In some embodiments, $R_{23}$ is substituted $C_2$-$C_{10}$ alkynyl. In some embodiments, $R_{23}$ is unsubstituted $C_2$-$C_{10}$ alkenyl. In some embodiments, $R_{23}$ is substituted $C_2$-$C_{10}$ alkenyl. In some embodiments, $R_{23}$ is unsubstituted acyloxy. In some embodiments, $R_{23}$ is substituted acyloxy. In some embodiments, $R_{23}$ is unsubstituted carbohydrate. In some embodiments, $R_{23}$ is substituted carbohydrate. In some embodiments, $R_{23}$ is unsubstituted acyloxy. In some embodiments, $R_{23}$ is substituted acyloxy. In some embodiments, $R_{23}$ is unsubstituted $C_1$-$C_{10}$ aliphatic acyl. In some embodiments, $R_{23}$ is substituted $C_1$-$C_{10}$ aliphatic acyl. In some embodiments, $R_{23}$ is unsubstituted $C_6$-$C_{10}$ aromatic acyl. In some embodiments, $R_{23}$ is substituted $C_6$-$C_{10}$ aromatic acyl. In some embodiments, $R_{23}$ is unsubstituted $C_6$-$C_{10}$ aralkyl acyl. In some embodiments, $R_{23}$ is substituted $C_6$-$C_{10}$ aralkyl acyl. In some embodiments, $R_{23}$ is unsubstituted $C_6$-$C_{10}$ alkylaryl acyl. In some embodiments, $R_{23}$ is substituted $C_6$-$C_{10}$ alkylaryl acyl. In some embodiments, $R_{23}$ is unsubstituted alkoxy. In some embodiments, $R_{23}$ is substituted alkoxy. In some embodiments, $R_{23}$ is unsubstituted aryl. In some embodiments, $R_{23}$ is substituted aryl. In some embodiments, $R_{23}$ is unsubstituted $C_3$-$C_{10}$heterocyclyl. In some embodiments, $R_{23}$ is substituted $C_3$-$C_{10}$heterocyclyl. In some embodiments, $R_{23}$ is unsubstituted heteroaryl. In some embodiments, $R_{23}$ is substituted heteroaryl. In some embodiments, $R_{23}$ is unsubstituted $C_3$-$C_{10}$cycloalkyl. In some embodiments, $R_{23}$ is substituted $C_3$-$C_{10}$cycloalkyl.

In some embodiments, the phosphorylated pyrone analog of Formula III is of Formula XXIII wherein the compound comprises at least one phosphate group:

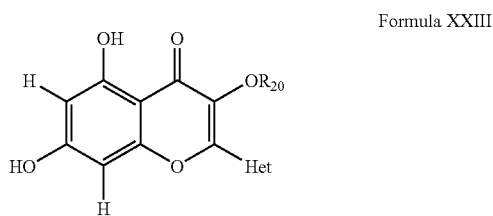

Formula XXIII

Wherein $R_{20}$ is hydrogen, $C_1$-$C_{10}$ alkyl, $C_2$-$C_{10}$ alkynyl, $C_2$-$C_{10}$ alkenyl, carbohydrate, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, aryl, $C_3$-$C_{10}$ heterocyclyl, heteroaryl, optionally substituted $C_3$-$C_{10}$cycloalkyl, —$PO_3WY$, —$CH_2PO_4WY$, —$CH_2PO_4Z$ or —$PO_3Z$;

Het is a 3 to 10 membered optionally substituted monocyclic or bicyclic heteroaromatic or heteroalicyclic ring system containing 1, 2, 3, 4, or 5 heteroatoms selected from the group of O, S, and N, with the proviso that no two adjacent ring atoms are O or S, wherein the ring system is unsaturated, partially unsaturated or saturated, wherein any number of the ring atoms have substituents as valency permits which are hydrogen, hydroxyl, carboxyaldehyde, alkylcarboxaldehyde, imino, $C_1$-$C_{10}$ alkyl, $C_1$-$C_{10}$ alkynyl, $C_1$-$C_{10}$ alkenyl, carboxyl, carbohydrate, acyloxy, nitro, halogen, $C_1$-$C_{10}$ aliphatic acyl, $C_5$-$C_{10}$ aromatic acyl, $C_6$-$C_{10}$ aralkyl acyl, $C_6$-$C_{10}$ alkylaryl acyl, alkoxy, amine, aryl, heteroaryl, $C_5$-$C_{10}$heterocycloalkyl, $C_5$-$C_{10}$cycloalkyl, —$OPO_3WY$, —$OCH_2PO_4WY$, —$OCH_2PO_4Z$ or —$OPO_3Z$; and W and Y are independently hydrogen, methyl, ethyl, alkyl, carbohydrate, or a cation, and Z is a multivalent cation.

In some embodiments, $R_{20}$ is hydrogen. In some embodiments, $R_{20}$ is unsubstituted $C_1$-$C_{10}$ alkyl. In some embodiments, $R_{20}$ is substituted $C_1$-$C_{10}$ alkyl. In some embodiments, $R_{20}$ is unsubstituted $C_2$-$C_{10}$ alkynyl. In some embodiments, $R_{20}$ is substituted $C_2$-$C_{10}$ alkynyl. In some embodiments, $R_{20}$ is unsubstituted $C_2$-$C_{10}$ alkenyl. In some embodiments, $R_{20}$ is substituted $C_2$-$C_{10}$ alkenyl. In some embodiments, $R_{20}$ is unsubstituted carbohydrate. In some embodiments, $R_{20}$ is substituted carbohydrate. In some embodiments, $R_{20}$ is unsubstituted $C_1$-$C_{10}$ aliphatic acyl. In some embodiments, $R_{20}$ is substituted $C_1$-$C_{10}$ aliphatic acyl. In some embodiments, $R_{20}$ is unsubstituted $C_6$-$C_{10}$ aromatic acyl. In some embodiments, $R_{20}$ is substituted $C_6$-$C_{10}$ aromatic acyl. In some embodiments, $R_{20}$ is unsubstituted $C_6$-$C_{10}$ aralkyl acyl. In some embodiments, $R_{20}$ is substituted $C_6$-$C_{10}$ aralkyl acyl. In some embodiments, $R_{20}$ is unsubstituted $C_6$-$C_{10}$ alkylaryl acyl. In some embodiments, $R_{20}$ is substituted $C_6$-$C_{10}$ alkylaryl acyl. In some embodiments, $R_{20}$ is unsubstituted aryl. In some embodiments, $R_{20}$ is substituted aryl. In some embodiments, $R_{20}$ is unsubstituted $C_3$-$C_{10}$heterocyclyl. In some embodiments, $R_{20}$ is substituted $C_3$-$C_{10}$heterocyclyl. In some embodiments, $R_{20}$ is unsubstituted heteroaryl. In some embodiments, $R_{20}$ is substituted heteroaryl. In some embodiments, $R_{20}$ is unsubstituted $C_3$-$C_{10}$cycloalkyl. In some embodiments, $R_{20}$ is substituted $C_3$-$C_{10}$cycloalkyl. In some embodiments, $R_{20}$ is —$PO_3WY$. In some embodiments, $R_{20}$ is —$CH_2PO_4WY$. In some embodiments, $R_{20}$ is —$CH_2PO_4Z$. In some embodiments, $R_{20}$ is —$PO_3Z$.

In some embodiments, Het is one of the following formulae:

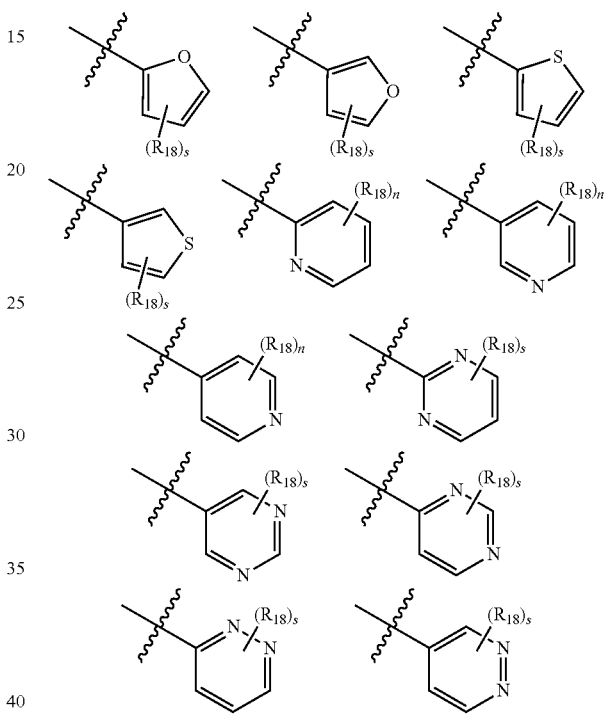

wherein each instance of $R_{18}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$;

s is an integer of 0, 1, 2, or 3; and n is an integer of 0, 1, 2, 3, or 4.

In some embodiments, $R_{18}$ is hydrogen. In some embodiments, $R_{18}$ is hydroxy. In some embodiments, $R_{18}$ is carboxaldehyde. In some embodiments, $R_{18}$ is unsubstituted amine. In some embodiments, $R_{18}$ is substituted amine. In some embodiments, $R_{18}$ is unsubstituted $C_1$-$C_{10}$ alkyl. In some embodiments, $R_{18}$ is unsubstituted $C_2$-$C_{10}$ alkynyl. In some embodiments, $R_{18}$ is substituted $C_2$-$C_{10}$ alkynyl. In some embodiments, $R_{18}$ is unsubstituted $C_2$-$C_{10}$ alkenyl. In some embodiments, $R_{18}$ is substituted $C_2$-$C_{10}$ alkenyl. In some embodiments, $R_{18}$ is carboxyl. In some embodiments, $R_{18}$ is unsubstituted carbohydrate. In some embodiments, $R_{18}$ is substituted carbohydrate. In some embodiments, $R_{18}$ is substituted carbohydrate. In some embodiments, $R_{18}$ is unsubstituted ester. In some embodiments, $R_{18}$ is substituted ester. In some embodiments, $R_{18}$ is unsubstituted acyloxy. In some embodiments, $R_{18}$ is substituted acyloxy. In some embodiments, $R_{18}$ is nitro. In some embodiments, $R_{18}$ is halogen. In some embodiments, $R_{18}$ is unsubstituted $C_1$-$C_{10}$ aliphatic acyl. In some embodiments, $R_{18}$ is substituted $C_1$-$C_{10}$ aliphatic acyl. In some embodiments, $R_{18}$ is unsubstituted $C_6$-$C_{10}$ aromatic acyl. In some embodiments, $R_{18}$ is substituted $C_6$-$C_{10}$ aromatic acyl. In some embodiments, $R_{18}$ is unsubstituted $C_6$-$C_{10}$ aralkyl acyl. In some embodiments, $R_{18}$ is substituted $C_6$-$C_{10}$ aralkyl acyl. In some embodiments, $R_{18}$ is unsubstituted $C_6$-$C_{10}$ alkylaryl acyl. In some embodiments, $R_{18}$ is substituted $C_6$-$C_{10}$ alkylaryl acyl. In some embodiments, $R_{18}$ is unsubstituted alkoxy. In some embodiments, $R_{18}$ is substituted alkoxy. In some embodiments, $R_{18}$ is unsubstituted aryl. In some embodiments, $R_{18}$ is substituted aryl. In some embodiments, $R_{18}$ is unsubstituted $C_3$-$C_{10}$heterocyclyl. In some embodiments, $R_{18}$ is substituted $C_3$-$C_{10}$heterocyclyl. In some embodiments, $R_{18}$ is unsubstituted heteroaryl. In some embodiments, $R_{18}$ is substituted heteroaryl. In some embodiments, $R_{18}$ is unsubstituted $C_3$-$C_{10}$cycloalkyl. In some embodiments, $R_{18}$ is substituted $C_3$-$C_{10}$cycloalkyl. In some embodiments, $R_{18}$ is —$OPO_3WY$. In some embodiments, $R_{18}$ is —$OCH_2PO_4WY$. In some embodiments, $R_{18}$ is —$OCH_2PO_4Z$. In some embodiments, $R_{18}$ is —$OPO_3Z$.

In some embodiments, n is an integer of 0. In some embodiments, n is an integer of 1. In some embodiments, n is an integer of 2. In some embodiments, n is an integer of 3. In some embodiments, n is an integer of 4.

In some embodiments, s is an integer of 0. In some embodiments, s is an integer of 1. In some embodiments, s is an integer of 2. In some embodiments, s is an integer of 3.

In some embodiments of the invention, the phosphorylated pyrone analog of Formula II is of Formula IV wherein the compound comprises at least one phosphate group:

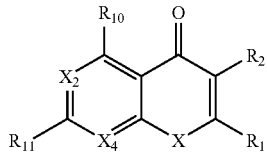

Formula IV wherein X, $X_2$, $X_4$, R', $R_1$, $R_2$, W, Y, and Z are as defined for Formula II; and $R_{10}$ and $R_{11}$ are independently hydrogen, hydroxyl, carboxaldehyde, amino, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$alkylaryl acyl, alkoxy, amine, aryl, $C_3$-$C_{10}$heterocyclyl, heteroaryl, $C_3$-$C_{10}$cycloalkyl, —$OPO_3WY$, —$OCH_2PO_4WY$, —$OCH_2PO_4Z$ or —$OPO_3Z$.

In some embodiments, $R_{10}$ is hydrogen. In some embodiments, $R_{10}$ is hydroxyl. In some embodiments, $R_{10}$ is carboxaldehyde. In some embodiments, $R_{10}$ is unsubstituted amine. In some embodiments, $R_{10}$ is substituted amine. In some embodiments, $R_{10}$ is unsubstituted $C_1$-$C_{10}$ alkyl. In some embodiments, $R_{10}$ is substituted $C_1$-$C_{10}$ alkyl. In some embodiments, $R_{10}$ is unsubstituted $C_2$-$C_{10}$ alkynyl. In some embodiments, $R_{10}$ is substituted $C_2$-$C_{10}$ alkynyl. In some embodiments, $R_{10}$ is unsubstituted $C_2$-$C_{10}$ alkenyl. In some embodiments, $R_{10}$ is substituted $C_2$-$C_{10}$ alkenyl. In some embodiments, $R_{10}$ is carboxyl. In some embodiments, $R_{10}$ is unsubstituted carbohydrate. In some embodiments, $R_{10}$ is substituted carbohydrate. In some embodiments, $R_{10}$ is unsubstituted ester. In some embodiments, $R_{10}$ is substituted ester. In some embodiments, $R_{10}$ is unsubstituted acyloxy. In some embodiments, $R_{10}$ is substituted acyloxy. In some embodiments, $R_{10}$ is nitro. In some embodiments, $R_{10}$ is halogen. In some embodiments, $R_{10}$ is unsubstituted $C_1$-$C_{10}$ aliphatic acyl. In some embodiments, $R_{10}$ is substituted $C_1$-$C_{10}$ aliphatic acyl. In some embodiments, $R_{10}$ is unsubstituted $C_6$-$C_{10}$ aromatic acyl. In some embodiments, $R_{10}$ is substituted $C_6$-$C_{10}$ aromatic acyl. In some embodiments, $R_{10}$ is unsubstituted $C_6$-$C_{10}$ aralkyl acyl. In some embodiments, $R_{10}$ is substituted $C_6$-$C_{10}$ aralkyl acyl. In some embodiments, $R_{10}$ is unsubstituted $C_6$-$C_{10}$ alkylaryl acyl. In some embodiments, $R_{10}$ is substituted $C_6$-$C_{10}$ alkylaryl acyl. In some embodiments, $R_{10}$ is unsubstituted alkoxy. In some embodiments, $R_{10}$ is substituted alkoxy. In some embodiments, $R_{10}$ is unsubstituted aryl. In some embodiments, $R_{10}$ is substituted aryl. In some embodiments, $R_{10}$ is unsubstituted $C_3$-$C_{10}$heterocyclyl. In some embodiments, $R_{10}$ is substituted $C_3$-$C_{10}$heterocyclyl. In some embodiments, $R_{10}$ is unsubstituted heteroaryl. In some embodiments, $R_{10}$ is unsubstituted $C_3$-$C_{10}$cycloalkyl. In some embodiments, $R_{10}$ is substituted $C_3$-$C_{10}$cycloalkyl. In some embodiments, $R_{10}$ is —$OPO_3WY$. In some embodiments, $R_{10}$ is —$OCH_2PO_4WY$. In some embodiments, $R_{10}$ is —$OCH_2PO_4Z$. In some embodiments, $R_{10}$ is —$OPO_3Z$.

In some embodiments, $R_{11}$ is hydrogen. In some embodiments, $R_{11}$ is hydroxyl. In some embodiments, $R_{11}$ is carboxaldehyde. In some embodiments, $R_{11}$ is unsubstituted amine. In some embodiments, $R_{11}$ is substituted amine. In some embodiments, $R_{11}$ is unsubstituted $C_1$-$C_{10}$ alkyl. In some embodiments, $R_{11}$ is substituted $C_1$-$C_{10}$ alkyl. In some embodiments, $R_{11}$ is unsubstituted $C_2$-$C_{10}$ alkynyl. In some embodiments, $R_{11}$ is substituted $C_2$-$C_{10}$ alkynyl. In some embodiments, $R_{11}$ is unsubstituted $C_2$-$C_{10}$ alkenyl. In some embodiments, $R_{11}$ is substituted $C_2$-$C_{10}$ alkenyl. In some embodiments, $R_{11}$ is carboxyl. In some embodiments, $R_{11}$ is unsubstituted carbohydrate. In some embodiments, $R_{11}$ is substituted carbohydrate. In some embodiments, $R_{11}$ is unsubstituted ester. In some embodiments, $R_{11}$ is substituted ester. In some embodiments, $R_{11}$ is unsubstituted acyloxy. In some embodiments, $R_{11}$ is substituted acyloxy. In some embodiments, $R_{11}$ is nitro. In some embodiments, $R_{11}$ is halogen. In some embodiments, $R_{11}$ is unsubstituted $C_1$-$C_{10}$ aliphatic acyl. In some embodiments, $R_{11}$ is substituted $C_1$-$C_{10}$ aliphatic acyl. In some embodiments, $R_{11}$ is unsubstituted $C_6$-$C_{10}$ aromatic acyl. In some embodiments, $R_{11}$ is substituted $C_6$-$C_{10}$ aromatic acyl. In some embodiments, $R_{11}$ is unsubstituted $C_6$-$C_{10}$ aralkyl acyl. In some embodiments, $R_{11}$ is substituted $C_6$-$C_{10}$ aralkyl acyl. In some embodiments, $R_{11}$ is unsubstituted $C_6$-$C_{10}$ alkylaryl acyl. In some embodiments, $R_{11}$ is substituted $C_6$-$C_{10}$ alkylaryl acyl. In some embodiments, $R_{11}$ is unsubstituted alkoxy. In some embodiments, $R_{11}$ is substituted alkoxy. In some embodiments, $R_{11}$ is unsubstituted aryl. In some embodiments, $R_{11}$ is substituted aryl. In some embodiments, $R_{11}$ is unsubstituted $C_3$-$C_{10}$heterocyclyl. In some embodiments, $R_{11}$ is substituted $C_3$-$C_{10}$heterocyclyl. In some embodiments, $R_{11}$ is unsubstituted heteroaryl. In some embodiments, $R_{11}$ is unsubstituted $C_3$-$C_{10}$cycloalkyl. In some embodiments, $R_{11}$ is substituted $C_3$-$C_{10}$cycloalkyl. In some embodiments, $R_{11}$ is —$OPO_3WY$. In some embodiments, $R_{11}$ is —$OCH_2PO_4WY$. In some embodiments, $R_{11}$ is —$OCH_2PO_4Z$. In some embodiments, $R_{11}$ is —$OPO_3Z$.

In some embodiments of the invention, the phosphorylated pyrone analog of Formula IV is of Formula XXIV or Formula XXV wherein the compound comprises at least one phosphate group:

Formula XXIV

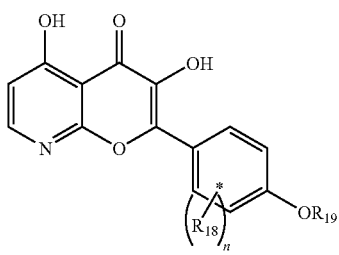

Formula XXV

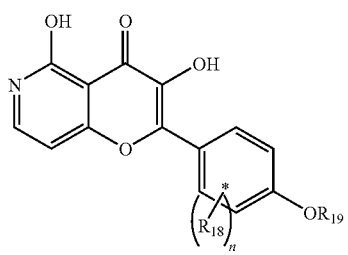

wherein $R_{18}$, $R_{19}$, and n are as defined in Formula II.

In some embodiments of the invention, the phosphorylated pyrone analog of Formula IV is of Formula XXVI or Formula XXVII wherein the compound comprises at least one phosphate group:

Formula XXVI

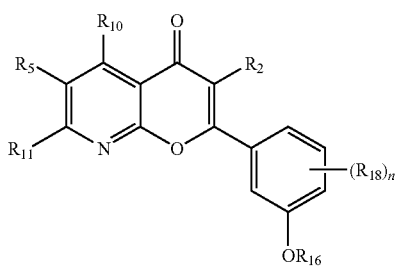

Formula XXVII

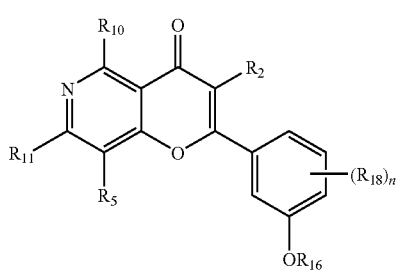

wherein $R_2$, $R_5$, W, Y, and Z are as defined for Formula II and $R_{10}$ and $R_{11}$ are as defined for Formula IV;

$R_{16}$ is hydrogen, —$PO_3WY$, —$CH_2PO_4WY$, —$CH_2PO_4Z$ or —$PO_3Z$;

wherein each instance of $R_{18}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$; and n is an integer of 0, 1, 2, 3, or 4.

In some embodiments of the invention, the phosphorylated pyrone analog of Formula IV is of Formula XXVIII wherein the compound comprises at least one phosphate group:

Formula XXVIII

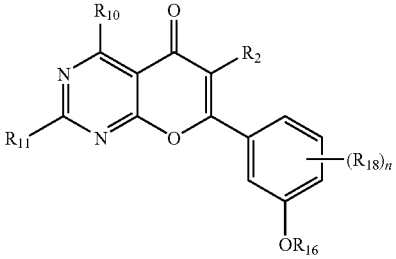

wherein $R_2$, W, Y, and Z are as defined for Formula II and $R_{10}$ and $R_{11}$ are as defined for Formula IV;

$R_{16}$ is hydrogen, —$PO_3WY$, —$CH_2PO_4WY$, —$CH_2PO_4Z$ or —$PO_3Z$;

wherein each instance of $R_{18}$ is independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$ alkylaryl acyl, alkoxy, alkyl, phosphate, aryl, heteroaryl, $C_3$-$C_{10}$ heterocyclic, $C_3$-$C_{10}$cycloalkyl, —$OPO_3WY$, —$OCH_2PO_4WY$, —$OCH_2PO_4Z$ or —$OPO_3Z$; and n is an integer of 0, 1, 2, 3, or 4.

In some embodiments of the invention, the phosphorylated pyrone analog of Formula II is of Formula V wherein the compound comprises at least one phosphate group:

Formula V

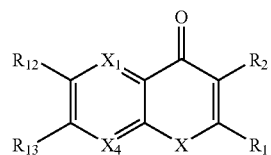

wherein X, $X_1$, $X_4$, R', $R_1$, $R_2$, W, Y, and Z are as defined for Formula II; and $R_{12}$ and $R_{13}$ are independently hydrogen, hydroxyl, carboxaldehyde, amine, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$alkylaryl acyl, alkoxy, amine, aryl, $C_3$-$C_{10}$heterocyclyl, heteroaryl, $C_3$-$C_{10}$cycloalkyl, —$OPO_3WY$, —$OCH_2PO_4WY$, —$OCH_2PO_4Z$ or —$OPO_3Z$.

In some embodiments, $R_{12}$ is hydrogen. In some embodiments, $R_{12}$ is hydroxyl. In some embodiments, $R_{12}$ is carboxaldehyde. In some embodiments, $R_{12}$ is unsubstituted amine. In some embodiments, $R_{12}$ is substituted amine. In some embodiments, $R_{12}$ is unsubstituted $C_1$-$C_{10}$ alkyl. In some embodiments, $R_{12}$ is substituted $C_1$-$C_{10}$ alkyl. In some embodiments, $R_{12}$ is unsubstituted $C_2$-$C_{10}$ alkynyl. In some embodiments, $R_{12}$ is substituted $C_2$-$C_{10}$ alkynyl. In some embodiments, $R_{12}$ is unsubstituted $C_2$-$C_{10}$ alkenyl. In some embodiments, $R_{12}$ is substituted $C_2$-$C_{10}$ alkenyl. In some embodiments, $R_{12}$ is carboxyl. In some embodiments, $R_{12}$ is unsubstituted carbohydrate. In some embodiments, $R_{12}$ is substituted carbohydrate. In some embodiments, $R_{12}$ is unsubstituted ester. In some embodiments, $R_{12}$ is substituted ester. In some embodiments, $R_{12}$ is unsubstituted acyloxy. In some embodiments, $R_{12}$ is substituted acyloxy. In some embodiments, $R_{12}$ is nitro. In some embodiments, $R_{12}$ is halogen. In some embodiments, $R_{12}$ is unsubstituted $C_1$-$C_{10}$ aliphatic acyl. In some embodiments, $R_{12}$ is substituted $C_1$-$C_{10}$ aliphatic acyl. In some embodiments, $R_{12}$ is unsubstituted $C_6$-$C_{10}$ aromatic acyl. In some embodiments, $R_{12}$ is substituted $C_6$-$C_{10}$ aromatic acyl. In some embodiments, $R_{12}$ is unsubstituted $C_6$-$C_{10}$ aralkyl acyl. In some embodiments, $R_{12}$ is substituted $C_6$-$C_{10}$ aralkyl acyl. In some embodiments, $R_{12}$ is unsubstituted $C_6$-$C_{10}$ alkylaryl acyl. In some embodiments, $R_{12}$ is substituted $C_6$-$C_{10}$ alkylaryl acyl. In some embodiments, $R_{12}$ is unsubstituted alkoxy. In some embodiments, $R_{12}$ is substituted alkoxy. In some embodiments, $R_{12}$ is unsubstituted aryl. In some embodiments, $R_{12}$ is substituted aryl. In some embodiments, $R_{12}$ is unsubstituted $C_3$-$C_{10}$ heterocyclyl. In some embodiments, $R_{12}$ is substituted $C_3$-$C_{10}$ heterocyclyl. In some embodiments, $R_{12}$ is unsubstituted heteroaryl. In some embodiments, $R_{12}$ is unsubstituted $C_3$-$C_{10}$ cycloalkyl. In some embodiments, $R_{12}$ is substituted $C_3$-$C_{10}$ cycloalkyl. In some embodiments, $R_{12}$ is —$OPO_3WY$. In some embodiments, $R_{12}$ is —$OCH_2PO_4WY$. In some embodiments, $R_{12}$ is —$OCH_2PO_4Z$. In some embodiments, $R_{12}$ is —$OPO_3Z$.

In some embodiments, $R_{13}$ is hydrogen. In some embodiments, $R_{13}$ is hydroxyl. In some embodiments, $R_{13}$ is carboxaldehyde. In some embodiments, $R_{13}$ is unsubstituted amine. In some embodiments, $R_{13}$ is substituted amine. In some embodiments, $R_{13}$ is unsubstituted $C_1$-$C_{10}$ alkyl. In some embodiments, $R_{13}$ is substituted $C_1$-$C_{10}$ alkyl. In some embodiments, $R_{13}$ is unsubstituted $C_2$-$C_{10}$ alkynyl. In some embodiments, $R_{13}$ is substituted $C_2$-$C_{10}$ alkynyl. In some embodiments, $R_{13}$ is unsubstituted $C_2$-$C_{10}$ alkenyl. In some embodiments, $R_{13}$ is substituted $C_2$-$C_{10}$ alkenyl. In some embodiments, $R_{13}$ is carboxyl. In some embodiments, $R_{13}$ is unsubstituted carbohydrate. In some embodiments, $R_{13}$ is substituted carbohydrate. In some embodiments, $R_{13}$ is unsubstituted ester. In some embodiments, $R_{13}$ is substituted ester. In some embodiments, $R_{13}$ is unsubstituted acyloxy. In some embodiments, $R_{13}$ is substituted acyloxy. In some embodiments, $R_{13}$ is nitro. In some embodiments, $R_{13}$ is halogen. In some embodiments, $R_{13}$ is unsubstituted $C_1$-$C_{10}$ aliphatic acyl. In some embodiments, $R_{13}$ is substituted $C_1$-$C_{10}$ aliphatic acyl. In some embodiments, $R_{13}$ is unsubstituted $C_6$-$C_{10}$ aromatic acyl. In some embodiments, $R_{13}$ is substituted $C_6$-$C_{10}$ aromatic acyl. In some embodiments, $R_{13}$ is unsubstituted $C_6$-$C_{10}$ aralkyl acyl. In some embodiments, $R_{13}$ is substituted $C_6$-$C_{10}$ aralkyl acyl. In some embodiments, $R_{13}$ is unsubstituted $C_6$-$C_{10}$ alkylaryl acyl. In some embodiments, $R_{13}$ is substituted $C_6$-$C_{10}$ alkylaryl acyl. In some embodiments, $R_{13}$ is unsubstituted alkoxy. In some embodiments, $R_{13}$ is substituted alkoxy. In some embodiments, $R_{13}$ is unsubstituted aryl. In some embodiments, $R_{13}$ is substituted aryl. In some embodiments, $R_{13}$ is unsubstituted $C_3$-$C_{10}$ heterocyclyl. In some embodiments, $R_{13}$ is substituted $C_3$-$C_{10}$ heterocyclyl. In some embodiments, $R_{13}$ is unsubstituted heteroaryl. In some embodiments, $R_{13}$ is unsubstituted $C_3$-$C_{10}$ cycloalkyl. In some embodiments, $R_{13}$ is substituted $C_3$-$C_{10}$ cycloalkyl. In some embodiments, $R_{13}$ is —$OPO_3WY$. In some embodiments, $R_{13}$ is —$OCH_2PO_4WY$. In some embodiments, $R_{13}$ is —$OCH_2PO_4Z$. In some embodiments, $R_{13}$ is —$OPO_3Z$.

In some embodiments of the invention, the phosphorylated pyrone analog of Formula V is of Formula XXIX or Formula XXX wherein the compound comprises at least one phosphate group:

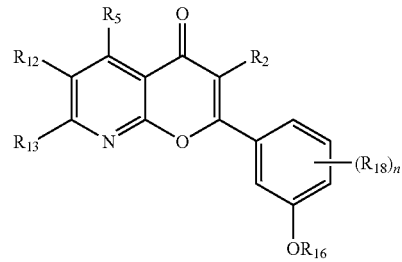

Formula XXIX

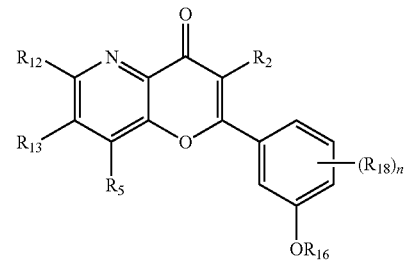

Formula XXX wherein $R_2$, $R_5$, $R_{18}$, n, W, Y, and Z are as defined for Formula II and $R_{12}$ and $R_{13}$ are as defined for Formula V; and
$R_{16}$ is hydrogen, —$PO_3WY$, —$CH_2PO_4WY$, —$CH_2PO_4Z$ or —$PO_3Z$.

In some embodiments of the invention, the phosphorylated pyrone analog of Formula V is of Formula XXXI wherein the compound comprises at least one phosphate group:

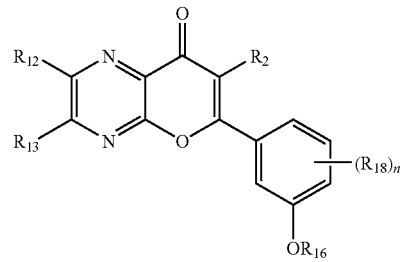

Formula XXXI wherein $R_2$, $R_{18}$, n, W, Y, and Z are as defined for Formula II and $R_{12}$ and $R_{13}$ are as defined for Formula V; and
$R_{16}$ is hydrogen, —$PO_3WY$, —$CH_2PO_4WY$, —$CH_2PO_4Z$ or —$PO_3Z$.

In some embodiments of the invention, the phosphorylated pyrone analog of Formula II is of Formula VI wherein the compound comprises at least one phosphate group:

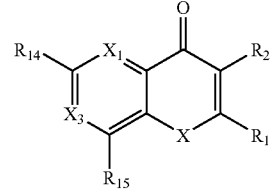

Formula VI wherein X, $X_1$, $X_3$, R', $R_1$, $R_2$, W, Y, and Z are as defined for Formula II; and
$R_{14}$ and $R_{15}$ are independently hydrogen, hydroxyl, carboxaldehyde, amino, $C_1$-$C_{10}$ alkyl, $C_2$-$C_{10}$ alkynyl, $C_2$-$C_{10}$ alkenyl, carboxyl, carbohydrate, ester, acyloxy, nitro, halogen, $C_1$-$C_{10}$ aliphatic acyl, $C_6$-$C_{10}$ aromatic acyl, $C_6$-$C_{10}$ aralkyl acyl, $C_6$-$C_{10}$alkylaryl acyl, alkoxy, amine, aryl, $C_3$-$C_{10}$heterocyclyl, heteroaryl, $C_3$-$C_{10}$cycloalkyl, —$OPO_3WY$, —$OCH_2PO_4WY$, —$OCH_2PO_4Z$ or —$OPO_3Z$.

In some embodiments, $R_{14}$ is hydrogen. In some embodiments, $R_{14}$ is hydroxyl. In some embodiments, $R_{14}$ is carboxaldehyde. In some embodiments, $R_{14}$ is unsubstituted amine. In some embodiments, $R_{14}$ is substituted amine. In some embodiments, $R_{14}$ is unsubstituted $C_1$-$C_{10}$ alkyl. In some embodiments, $R_{14}$ is substituted $C_1$-$C_{10}$ alkyl. In some embodiments, $R_{14}$ is unsubstituted $C_2$-$C_{10}$ alkynyl. In some embodiments, $R_{14}$ is substituted $C_2$-$C_{10}$ alkynyl. In some embodiments, $R_{14}$ is unsubstituted $C_2$-$C_{10}$ alkenyl. In some embodiments, $R_{14}$ is substituted $C_2$-$C_{10}$ alkenyl. In some embodiments, $R_{14}$ is carboxyl. In some embodiments, $R_{14}$ is unsubstituted carbohydrate. In some embodiments, $R_{14}$ is substituted carbohydrate. In some embodiments, $R_{14}$ is unsubstituted ester. In some embodiments, $R_{14}$ is substituted ester. In some embodiments, $R_{14}$ is unsubstituted acyloxy. In some embodiments, $R_{14}$ is substituted acyloxy. In some embodiments, $R_{14}$ is nitro. In some embodiments, $R_{14}$ is halogen. In some embodiments, $R_{14}$ is unsubstituted $C_1$-$C_{10}$ aliphatic acyl. In some embodiments, $R_{14}$ is substituted $C_1$-$C_{10}$ aliphatic acyl. In some embodiments, $R_{14}$ is unsubstituted $C_6$-$C_{10}$ aromatic acyl. In some embodiments, $R_{14}$ is substituted $C_6$-$C_{10}$ aromatic acyl. In some embodiments, $R_{14}$ is unsubstituted $C_6$-$C_{10}$ aralkyl acyl. In some embodiments, $R_{14}$ is substituted $C_6$-$C_{10}$ aralkyl acyl. In some embodiments, $R_{14}$ is unsubstituted $C_6$-$C_{10}$ alkylaryl acyl. In some embodiments, $R_{14}$ is substituted $C_6$-$C_{10}$ alkylaryl acyl. In some embodiments, $R_{14}$ is unsubstituted alkoxy. In some embodiments, $R_{14}$ is substituted alkoxy. In some embodiments, $R_{14}$ is unsubstituted aryl. In some embodiments, $R_{14}$ is substituted aryl. In some embodiments, $R_{14}$ is unsubstituted $C_3$-$C_{10}$heterocyclyl. In some embodiments, $R_{14}$ is substituted $C_3$-$C_{10}$heterocyclyl. In some embodiments, $R_{14}$ is unsubstituted heteroaryl. In some embodiments, $R_{14}$ is unsubstituted $C_3$-$C_{10}$cycloalkyl. In some embodiments, $R_{14}$ is substituted $C_3$-$C_{10}$cycloalkyl. In some embodiments, $R_{14}$ is —$OPO_3WY$. In some embodiments, $R_{14}$ is —$OCH_2PO_4WY$. In some embodiments, $R_{14}$ is —$OCH_2PO_4Z$. In some embodiments, $R_{14}$ is —$OPO_3Z$.

In some embodiments, $R_{15}$ is hydrogen. In some embodiments, $R_{15}$ is hydroxyl. In some embodiments, $R_{15}$ is carboxaldehyde. In some embodiments, $R_{15}$ is unsubstituted amine. In some embodiments, $R_{15}$ is substituted amine. In some embodiments, $R_{15}$ is unsubstituted $C_1$-$C_{10}$ alkyl. In some embodiments, $R_{15}$ is substituted $C_1$-$C_{10}$ alkyl. In some embodiments, $R_{15}$ is unsubstituted $C_2$-$C_{10}$ alkynyl. In some embodiments, $R_{15}$ is substituted $C_2$-$C_{10}$ alkynyl. In some embodiments, $R_{15}$ is unsubstituted $C_2$-$C_{10}$ alkenyl. In some embodiments, $R_{15}$ is substituted $C_2$-$C_{10}$ alkenyl. In some embodiments, $R_{15}$ is carboxyl. In some embodiments, $R_{15}$ is unsubstituted carbohydrate. In some embodiments, $R_{15}$ is substituted carbohydrate. In some embodiments, $R_{15}$ is unsubstituted ester. In some embodiments, $R_{15}$ is substituted ester. In some embodiments, $R_{15}$ is unsubstituted acyloxy. In some embodiments, $R_{15}$ is substituted acyloxy. In some embodiments, $R_{13}$ is nitro. In some embodiments, $R_{13}$ is halogen. In some embodiments, $R_{15}$ is unsubstituted $C_1$-$C_{10}$ aliphatic acyl. In some embodiments, $R_{15}$ is substituted $C_1$-$C_{10}$ aliphatic acyl. In some embodiments, $R_{15}$ is unsubstituted $C_6$-$C_{10}$ aromatic acyl. In some embodiments, $R_{15}$ is substituted $C_6$-$C_{10}$ aromatic acyl. In some embodiments, $R_{15}$ is unsubstituted $C_6$-$C_{10}$ aralkyl acyl. In some embodiments, $R_{15}$ is substituted $C_6$-$C_{10}$ aralkyl acyl. In some embodiments, $R_{15}$ is unsubstituted $C_6$-$C_{10}$ alkylaryl acyl. In some embodiments, $R_{15}$ is substituted $C_6$-$C_{10}$ alkylaryl acyl. In some embodiments, $R_{15}$ is unsubstituted alkoxy. In some embodiments, $R_{15}$ is substituted alkoxy. In some embodiments, $R_{15}$ is unsubstituted aryl. In some embodiments, $R_{15}$ is substituted aryl. In some embodiments, $R_{15}$ is unsubstituted $C_3$-$C_{10}$heterocyclyl. In some embodiments, $R_{15}$ is substituted $C_3$-$C_{10}$heterocyclyl. In some embodiments, $R_{15}$ is unsubstituted heteroaryl. In some embodiments, $R_{15}$ is unsubstituted $C_3$-$C_{10}$cycloalkyl. In some embodiments, $R_{15}$ is substituted $C_3$-$C_{10}$cycloalkyl. In some embodiments, $R_{15}$ is —$OPO_3WY$. In some embodiments, $R_{15}$ is —$OCH_2PO_4WY$. In some embodiments, $R_{15}$ is —$OCH_2PO_4Z$. In some embodiments, $R_{15}$ is —$OPO_3Z$.

In some embodiments of the invention, the phosphorylated pyrone analog of Formula VI is of Formula XXXII or Formula XXXIII wherein the compound comprises at least one phosphate group:

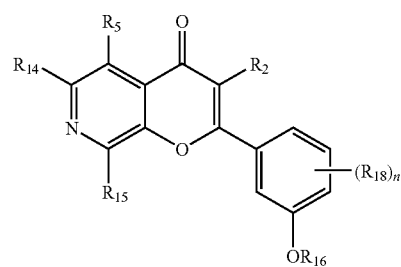

Formula XXXII

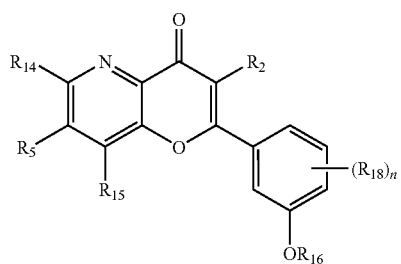

Formula XXXIII wherein $R_2$, $R_5$, $R_{18}$, n, W, Y, and Z are as defined for Formula II and $R_{14}$ and $R_{15}$ are as defined for Formula V; and
$R_{16}$ is hydrogen, —$PO_3WY$, —$CH_2PO_4WY$, —$CH_2PO_4Z$ or —$PO_3Z$.

In some embodiments of the invention, the phosphorylated pyrone analog of Formula VI is of Formula XXXIV wherein the compound comprises at least one phosphate group:

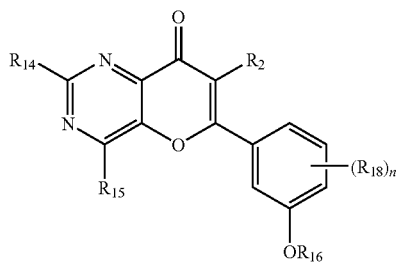

Formula XXXIV wherein $R_2$, $R_{18}$, n, W, Y, and Z are as defined for Formula II and $R_{14}$ and $R_{15}$ are as defined for Formula V; and
$R_{16}$ is hydrogen, —$PO_3WY$, —$CH_2PO_4WY$, —$CH_2PO_4Z$ or —$PO_3Z$.

A useful class of phosphorylated polyphenols is the phosphorylated flavonoids. Flavonoids, the most abundant polyphenols in the diet, can be classified into subgroups based on differences in their chemical structures. Compounds useful in the invention include phosphorylated compounds of the basic flavonoid structure, shown below (formula XXXV):

formula (XXXV)

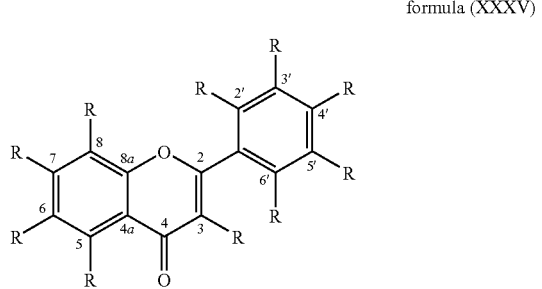

wherein the 2,3 bond may be saturated or unsaturated, and wherein each R can be independently selected from the group consisting of hydrogen, halogen, substituted or unsubstituted hydroxyl, substituted or unsubstituted amine, substituted or unsubstituted thiol, substituted or unsubstituted $C_1$-$C_{10}$ alkyl, substituted or unsubstituted $C_1$-$C_{10}$ alkynyl, substituted or unsubstituted $C_1$-$C_{10}$ alkenyl, substituted or unsubstituted aryl, substituted or unsubstituted heteroaryl, substituted or unsubstituted $C_5$-$C_{10}$ cycloalkyl, substituted or unsubstituted $C_5$-$C_{10}$ heterocycloalkyl, substituted or unsubstituted $C_1$-$C_{10}$ aliphatic acyl, substituted or unsubstituted $C_1$-$C_{10}$ aromatic acyl, trialkylsilyl, substituted or unsubstituted ether, carbohydrate, and substituted carbohydrate; and wherein at least one R is —$OPO_3XY$, or —$OPO_3Z$, wherein X and Y are independently selected from hydrogen, methyl, ethyl, alkyl, carbohydrate, and a cation, and wherein Z is a multivalent cation, and its pharmaceutically acceptable salts, esters, prodrugs, analogs, isomers, stereoisomers or tautomers thereof.

In some embodiments, the invention utilizes a phosphorylated pyrone analog such as a phosphorylated flavonoid where the molecule is planar. In some embodiments, the invention utilizes a phosphorylated flavonoid where the 2-3 bond is unsaturated. In some embodiments, the invention utilizes a phosphorylated flavonoid where the 3-position is hydroxylated or phosphorylated. In some embodiments, the invention utilizes a flavonoid where the 2-3 bond is unsaturated and the 3-position is hydroxylated or phosphorylated (e.g., flavonols).

In some embodiments, the invention utilizes one or more phosphorylated flavonoids selected from the group consisting of phosphorylated quercetin, phosphorylated isoquercetin, phosphorylated flavone, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, phosphorylated and phosphorylated epicatechin. In some embodiments, the invention utilizes one or more phosphorylated flavonoids selected from the group consisting of phosphorylated quercetin, phosphorylated fisetin, phoshorylated 5,7-dideoxyquercetin, phosphorylated isoquercetin, phosphorylated apigenin, phosphorylated rhoifolin, phosphorylated galangin, phosphorylated fisetin, phosphorylated morin, phosphorylated rutin, phosphorylated kaempferol, phosphorylated myricetin, phosphorylated naringenin, phosphorylated hesperetin, phosphorylated phloretin, and phosphorylated genistein, phosphorylated 5,7-dideoxyquercetin. Structures of the un-phosphorylated versions of these compounds are well-known in the art. See, e.g., Critchfield et al. (1994) Biochem. Pharmacol 7:1437-1445.

In some embodiments, the invention utilizes a phosphorylated flavonol. In some embodiments, the phosphorylated flavonol is selected from the group consisting of phosphorylated quercetin, phosphorylated fisetin, phosphorylated morin, phosphorylated rutin, phosphorylated myricetin, phosphorylated galangin, phosphorylated and phosphorylated kaempherol, and combinations thereof. In some embodiments, the phosphorylated flavonol is selected from the group consisting of phosphorylated quercetin, phosphorylated fisetin, phoshorylated 5,7-dideoxyquercetin, phosphorylated galangin, and phosphorylated kaempherol, and combinations thereof. In some embodiments, the phosphorylated flavonol is phosphorylated quercetin. In some embodiments, the phosphorylated flavonol is phosphorylated galangin. In some embodiments, the phosphorylated flavonol is phosphorylated kaempherol. In some embodiments, the phosphorylated flavonol is phosphorylated fisetin. In some embodiments, the phosphorylated flavonol is phosphorylated 5,7-dideoxyquercetin. In some embodiments, the phosphorylated flavonol is quercetin-3'-O-phosphate.

In some embodiments, the phosphorylated polyphenol comprises a compound with the structure of f (XXXV), its pharmaceutically or veterinarily acceptable salts, esters, or prodrugs: wherein each R is independently selected from the group of hydrogen, halogen, hydroxyl, —$OPO_3XY$, or —$OPO_3Z$, wherein X and Y are independently selected from hydrogen, methyl, ethyl, alkyl, carbohydrate, and a cation, wherein Z is a multivalent cation, and wherein at least one R is —$OPO_3XY$, or —$OPO_3Z$.

In some embodiments, the phosphorylated polyphenol of the invention can have the structure shown below (formula XXXVI):

formula (XXXVI)

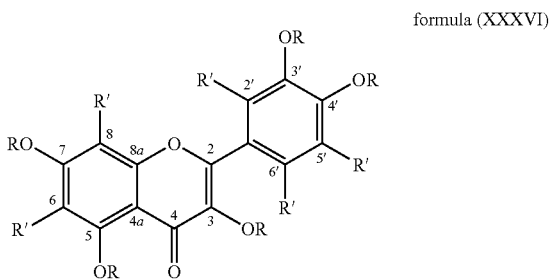

wherein each R' can be independently selected from the group consisting of hydrogen, substituted or unsubstituted $C_1$-$C_{10}$ alkyl, substituted or unsubstituted aryl, substituted or unsubstituted $C_1$-$C_{10}$ aliphatic acyl, substituted or unsubstituted $C_1$-$C_{10}$ aromatic acyl, trialkylsilyl, substituted or unsubstituted ether, carbohydrate, and substituted carbohydrate;

wherein each R can be independently selected from the group consisting of hydrogen, substituted or unsubstituted $C_1$-$C_{10}$ alkyl, substituted or unsubstituted aryl, substituted or unsubstituted $C_1$-$C_{10}$ aliphatic acyl, substituted or unsubstituted $C_1$-$C_{10}$ aromatic acyl, trialkylsilyl, substituted or unsubstituted ether, carbohydrate, and substituted carbohydrate; wherein at least one R is —OPO$_3$XY, or —OPO$_3$Z, wherein X and Y are independently selected from hydrogen, methyl, ethyl, alkyl carbohydrate, and a cation.

and its pharmaceutically acceptable salts, esters, prodrugs, analogs, isomers, stereoisomers or tautomers thereof. In addition, metabolites of the phosphorylated compounds of formula (XXXVI) including their glucouronides are phosphorylated compounds useful in the invention.

A particularly useful phosphorylated flavonol is phosphorylated quercetin. Quercetin may be used to illustrate formulations and methods useful in the invention, however, it is understood that the discussion of quercetin applies equally to other flavonoids, flavonols, and polyphenols useful in the invention, e.g., kaempferol and galangin. The basic structure of quercetin is the structure of formula (XXXVII) where $R_1$-$R_5$ are hydrogen. This form of quercetin can also be referred to as quercetin aglycone. Unless otherwise specified the term "quercetin", as used herein, can also refer to glycosides of quercetin, wherein one or more of the $R_1$-$R_5$ comprise a carbohydrate.

Useful phosphorylated polyphenols of the present invention are phosphorylated polyphenols of the structure of formula (XXXVII) or its pharmaceutically or veterinarily acceptable salts, glycosides, esters, or prodrugs:

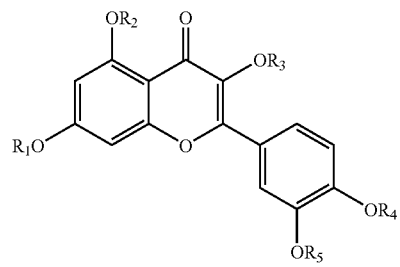

formula (XXXVII)

wherein $R_1$, $R_2$, $R_3$, $R_4$, and $R_5$ are independently selected from the group of hydrogen, —PO$_3$XY, and —PO$_3$Z, wherein X and Y are independently selected from hydrogen, methyl, ethyl, alkyl carbohydrate, and a cation, wherein Z is a multivalent cation, and wherein at least one of the $R_1$-$R_5$ is —PO$_3$XY, or —PO$_3$Z.

In some embodiments of the invention, the phosphorylated polyphenol can comprise a cyclic phosphate. In some embodiments, the invention is a composition comprising a compound of formula (XXXVIII), its pharmaceutically or veterinarily acceptable salts, glycosides, esters, or prodrugs:

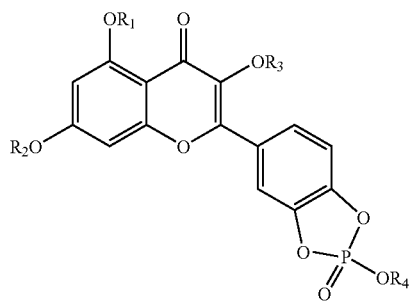

formula (XXXVIII)

wherein $R_1$, $R_2$, and $R_3$ are each independently selected from the group of hydrogen, —PO$_3$XY, and —PO$_3$Z, wherein X and Y are independently selected from hydrogen, methyl, ethyl, alkyl, carbohydrate, and a cation, wherein Z is a multivalent cation, and wherein $R_4$ is selected from the group of hydrogen, methyl, ethyl, alkyl, carbohydrate, and a cation.

A useful phosphorylated polyphenol of the invention comprises a compound of formula (XXXIX), or its pharmaceutically or veterinarily acceptable salts, glycosides, esters, or prodrugs:

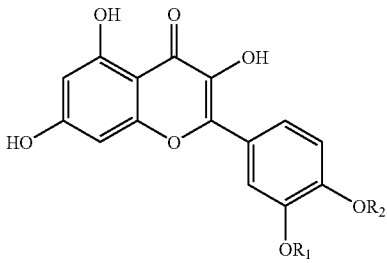

formula (XXXIX)

wherein $R_1$, and $R_2$ are each independently selected from the group consisting of hydrogen, —PO3XY, and —PO3Z, wherein X and Y are independently selected from hydrogen, methyl, ethyl, alkyl, carbohydrate, and a cation, wherein Z is a multivalent cation.

In some cases the monophosphate compound is useful, for example, wherein either $R_1$ or $R_2$ comprises a phosphate group. The monphosphate group can be, for example, either —PO3XY, and —PO3Z as described herein.

Thus, the compounds quercetin-3'-O-phosphate, or quercetin-4'-O-phosphate can be useful in the invention.

In some cases, the level of purity of the compound can dramatically affect its performance. In some embodiments the invention comprises quercetin-3'-O-phosphate at a purity of between about 90% and about 99.999%. In some embodiments the invention comprises quercetin-3'-O-phosphate at a purity of between about 95% and about 99.99%. In some embodiments the invention comprises quercetin-3'-O-phosphate at a purity of between about 98% and about 99.99%. In some embodiments the invention comprises quercetin-3'-O-phosphate at a purity of between about 99% and about 99.9%. In some embodiments the invention comprises quercetin-3'-O-phosphate at a purity of between about 99.5% and about 99.9%. In some embodiments the invention comprises quercetin-3'-O-phosphate at a purity of between about 99.8% and about 99.9%. In some embodiments the invention comprises quercetin-3'-O-phosphate at a purity greater than about 90%, 95%. 96%, 97%. 98%. 98.5%, 99%. 99.5%, 99.8%, 99.9%, 99.99%, 99.999% or greater. In some embodiments the invention comprises quercetin-3'-O-phosphate at a purity greater than about 90%. In some embodiments the invention comprises quercetin-3'-O-phosphate at a purity greater than about 95%. In some embodiments the invention comprises quercetin-3'-O-phosphate at a purity greater than about 98%. In some embodiments the invention comprises quercetin-3'-O-phosphate at a purity greater than about 99%. In some embodiments the invention comprises quercetin-3'-O-phosphate at a purity greater than about 99.5%. In some embodiments the invention comprises quercetin-3'-O-phosphate at a purity greater than about 99.8%.

In some cases, the level of purity of the compound can dramatically affect its performance. In some embodiments the invention comprises quercetin-4'-O-phosphate at a purity of between about 90% and about 99.999%. In some embodiments the invention comprises quercetin-4'-O-phosphate at a purity of between about 95% and about 99.99%. In some embodiments the invention comprises quercetin-4'-O-phosphate at a purity of between about 98% and about 99.99%. In some embodiments the invention comprises quercetin-4'-O-phosphate at a purity of between about 99% and about 99.9%. In some embodiments the invention comprises quercetin-4'-O-phosphate at a purity of between about 99.5% and about 99.9%. In some embodiments the invention comprises quercetin-4'-O-phosphate at a purity of between about 99.8% and about 99.9%. In some embodiments the invention comprises quercetin-4'-O-phosphate at a purity greater than about 90%, 95%. 96%, 97%, 98%. 98.5%, 99%. 99.5%, 99.8%, 99.9%, 99.99%, 99.999% or greater. In some embodiments the invention comprises quercetin-4'-O-phosphate at a purity greater than about 90%. In some embodiments the invention comprises quercetin-4'-O-phosphate at a purity greater than about 95%. In some embodiments the invention comprises quercetin-4'-O-phosphate at a purity greater than about 98%. In some embodiments the invention comprises quercetin-4'-O-phosphate at a purity greater than about 99%. In some embodiments the invention comprises quercetin-4'-O-phosphate at a purity greater than about 99.5%. In some embodiments the invention comprises quercetin-4'-O-phosphate at a purity greater than about 99.8%.

In some cases mixtures of quercetin-3'-O-phosphate and quercetin-4'-O-phosphate can be useful in the invention. The invention can comprise mixtures wherein quercetin-3'-O-phosphate is present at about 50% to about 100% and quercetin-4'-O-phosphate is present between about 50% and about 0%. The invention can comprise mixtures wherein quercetin-4'-O-phosphate is present at about 50% to about 100% and quercetin-3'-O-phosphate is present between about 50% and about 0%. In some cases the quercetin-3'-O-phosphate is present at about 80% to about 100% and the quercetin-4'-O-phosphate is present at between about 20% and about 0%. In some cases the quercetin-3'-O-phosphate is present at about 85% to about 100% and the quercetin-4'-O-phosphate is present at between about 15% and about 0%. In some cases the quercetin-3'-O-phosphate is present at about 90% to about 100% and the quercetin-4'-O-phosphate is present at between about 10% and about 0%. In some cases the quercetin-3'-O-phosphate is present at about 95% to about 100% and the quercetin-4'-O-phosphate is present at between about 5% and about 0%. In some cases the quercetin-3'-O-phosphate is present at about 97% to about 100% and the quercetin-4'-O-phosphate is present at between about 3% and about 0%. In some cases the quercetin-3'-O-phosphate is present at about 98% to about 100% and the quercetin-4'-O-phosphate is present at between about 2% and about 0%. In some cases the quercetin-3'-O-phosphate is present at about 99% to about 100% and the quercetin-4'-O-phosphate is present at between about 1% and about 0%.

In some embodiments, the phosphorylated quercetin is in a carbohydrate-derivatized form, e.g., a phosphorylated quercetin-O-saccharide. Phosphorylated quercetin-O-saccharides useful in the invention include, but are not limited to, phosphorylated quercetin 3-O-glycoside, phosphorylated quercetin 3-O-glucorhamnoside, phosphorylated quercetin 3-O-galactoside, phosphorylated quercetin 3-O-xyloside, and phosphorylated quercetin 3-O-rhamnoside. In some embodiments, the invention utilizes a phosphorylated quercetin 7-O-saccharide. The phosphorylated quercetin-O-saccharide may be phosphorylated on the hydroxyl positions directly attached to quercetin, or it may be phosphorylated on hydroxyl positions of the carbohydrate.

The term "pharmaceutically acceptable cation" as used herein refers to a positively charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, and guanidinium ions and protonated forms of lysine, choline and procaine.

The compounds presented herein may possess one or more chiral centers and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

In some embodiments, the invention utilizes a phosphorylated quercetin aglycone. In some embodiments, a combination of phosphorylated aglycones and phosphorylated carbohydrate-derivatized quercetins is used. It will be appreciated that the various forms of quercetin may have different properties useful in the compositions and methods of the invention, and that the route of administration can determine the choice of forms, or combinations of forms, used in the composition or method. Choice of a single form, or of combinations, is a matter of routine experimentation.

Thus, in some embodiments the invention features a composition or method utilizing phosphorylated quercetin, phosphorylated fisetin, phosphorylated 5,7-dideoxyquercetin and or its metabolites to reduce or eliminate one or more side or fetal effects of a substance, such as a therapeutic agent, e.g., an immunosuppressive.

In some embodiments, the phosphorylated flavonoid, e.g. phosphorylated quercetin, phosphorylated fisetin, phosphorylated 5,7-dideoxyquercetin is provided in a form for oral consumption. Oral bioavailability of phosphorylated quercetin O-saccharides may be superior to that of phosphorylated quercetin aglycones, or the saccharide derivative may have other properties useful in the invention. The bioavailability of the various components is dependent on 1) the site of carbohydrate moiety or moieties and ii) the pendant sugar unit. In addition it is believed that specific carriers can be responsible for the absorption of various quercetin glycosides, as well as specific intestinal betaglucosidases. After distribution in the body, the major metabolite, quercetin glucuronide (e.g., quercetin 3-O-glucoronide), may be found. Oral bioavailability can be sensitive to the presence of food factors.

In compositions for oral delivery of phosphorylated quercetin, carbohydrate-derivatized forms (also referred to herein as "phosphorylated quercetin saccharides") are used in some embodiments; various combinations of carbohydrate-derivatized forms and/or aglycone may be used in some embodiments. In some embodiments, phosphorylated quercetin-3-O-glycoside is used in an oral preparation of quercetin; in some embodiments, a pharmaceutically acceptable excipient is included in the composition. In some embodiments, phosphorylated quercetin 3-O-glucorhamnoside is used in an oral preparation of quercetin; in some embodiments, a pharmaceutically acceptable excipient is included in the composition. In some embodiments, a combination of phosphorylated quercetin-3-O-glycoside and phosphorylated quercetin 3-O-glucorhamnoside is used in an oral preparation of quercetin; in some embodiments, a pharmaceutically acceptable excipient is included in the composition. Other carbohydrate-derivatized forms of quercetin, or other forms of phosphorylated quercetin which are derivatives as described above, can also be used, based on their oral bioavailability, their metabolism, their incidence of gastrointestinal or other side effects, and other factors known in the art. Determining the bioavailability of phosphorylated quercetin in the form of derivatives including aglycones and glycosides is a matter of routine experimentation. See, e.g., Graefe et al., J. Clin. Pharmacol. (2001) 451:492-499; Arts et al. (2004) Brit. J. Nutr. 91:841-847; Moon et al. (2001) Free Rad. Biol. Med. 30:1274-1285; Hollman et al. (1995) Am. J. Clin. Nutr. 62:1276-1282; Jenaelle et al. (2005) Nutr. J. 4:1, and Cermak et al. (2003) J. Nutr. 133: 2802-2807, all of which are incorporated by reference herein in their entirety.

"Carbohydrate" as used herein, includes, but not limited to, monosaccharides, disaccharides, oligosaccharides, or polysaccharides. Monosaccharide for example includes, but not limited to, allose, altrose, mannose, gulose, Idose, glucose, galactose, talose, and fructose. Disaccharides for example includes, but not limited to, glucorhamnose, trehalose, sucrose, lactose, maltose, galactosucrose, N-acetyllactosamine, cellobiose, gentiobiose, isomaltose, melibiose, primeverose, hesperodinose, and rutinose. Oligosaccharides for example includes, but not limited to, raffinose, nystose, panose, cellotriose, maltotriose, maltotetraose, xylobiose, galactotetraose, isopanose, cyclodextrin (α-CD) or cyclomaltohexaose, β-cyclodextrin (β-CD) or cyclomaltoheptaose and γ-cyclodextrin (γ-CD) or cyclomaltooctaose. Polysaccharide for example includes, but not limited to, xylan, mannan, galactan, glucan, arabinan, pustulan, gellan, guaran, xanthan, and hyaluronan. Some examples include, but not limited to, starch, glycogen, cellulose, insulin, chitin, amylose and amylopectin. For further description of carbohydrate moieties, see U.S. Patent Publication No. 2006/0111308, in particular paragraphs [122] and PCT Publication No. WO0655672, in particular paragraphs [90]-[108].

In some of these embodiments, a pharmaceutically acceptable excipient is also included. In some embodiments, the phosphorylated polyphenols can be formulated with cyclodextrins. Cyclodextrins and their derivatives can be used in liquid formulations to enhance the aqueous solubility of hydrophobic compounds. Cyclodextrins are cyclic carbohydrates derived from starch. The unmodified cyclodextrins differ by the number of glucopyranose units joined together in the cylindrical structure. The parent cyclodextrins typically contain 6, 7, or 8 glucopyranose units and are referred to as alpha-, beta-, and gamma-cyclodextrin respectively. Each cyclodextrin subunit has secondary hydroxyl groups at the 2 and 3-positions and a primary hydroxyl group at the 6-position. The cyclodextrins may be pictured as hollow truncated cones with hydrophilic exterior surfaces and hydrophobic interior cavities. In aqueous solutions, these hydrophobic cavities can incorporate hydrophobic organic compounds, which can fit all, or part of their structure into these cavities. This process, sometimes referred to as inclusion complexation, may result in increased apparent aqueous solubility and stability for the complexed drug. The complex is stabilized by hydrophobic interactions and does not generally involve the formation of any covalent bonds.

Cyclodextrins can be derivatized to improve their properties. Cyclodextrin derivatives that are particularly useful for pharmaceutical applications include the hydroxypropyl derivatives of alpha-, beta- and gamma-cyclodextrin, sulfoalkylether cyclodextrins such as sulfobutylether beta-cyclodextrin, alkylated cyclodextrins such as the randomly methylated beta.-cyclodextrin, and various branched cyclodextrins such as glucosyl- and maltosyl-beta.-cyclodextrin. Chemical modification of the parent cyclodextrins (usually at the hydroxyl moieties) has resulted in derivatives with some-times improved safety while retaining or improving the complexation ability of the cyclodextrin. The chemical modifications, such as sulfoalkyl ether and hydroxypropyl, can result in rendering the cyclodextrins amorphous rather than crystalline, leading to improved solubility.

In some embodiments, the phosphorylated polyphenols for example phosphorylated pyrone analog such as a phosphorylated flavonoid, e.g. phosphorylated quercetin are formulated with sulfoalkyl ether derivatives. The sulfoalkyl ether -CDs are a class of negatively charged cyclodextrins, which vary in the nature of the alkyl spacer, the salt form, the degree of substitution and the starting parent cyclodextrin. A useful form of cyclodextrin is sulfobutylether-7-β-cyclodextrin, which is available under the trade name Captisol™ form CyDex, Inc. which has an average of about 7 substituents per cyclodextrin molecule. The anionic sulfobutyl ether substituents improves the aqueous solubility of the parent cyclodextrin. Reversible, non-covalent, complexation of flavonoids with the sulfobutylether-7-β-cyclodextrin. cyclodextrin can provide for increased solubility and stability of phosphorylated polyphenols in aqueous solutions.

III. BLOOD-TISSUE BARRIER

In some embodiments, the invention provides methods and compositions that modulate a blood tissue barrier (BTB) transport protein. BTB transport proteins play a role in the maintenance of barrier to foreign molecules and/or removal of substances from spaces (e.g. cells). A BTB barrier may be any structure that is capable of modulating the concentration of a substance (e.g., therapeutic agent) in a physiological compartment. The barrier can be a boundary between blood and a physiological compartment such as a cell, an organ, or a tissue. The barrier can be a cell membrane or a layer of cells. One example of such a barrier is the blood kidney barrier. In some embodiments, the phosphorylated polyphenol and/or its metabolite acts as a modulator of a BTB transport protein. In some embodiments, the phosphorylated polyphenol and/or its metabolite acts as a modulator of a BTB transport protein that is an ABC transport protein (see below). In some embodiments, the phosphorylated polyphenol and/or its metabolite acts as a BTB transport protein activator. In some embodiments, the phosphorylated polyphenol and/or its metabolite is a modulator of P-gP, e.g., an activator of P-gP (see below).

A. Blood-Tissue Barrier Transporters

Without being limited by theory, it is thought that the compositions and methods of the invention operate by modulating the transport of molecules across blood-tissue barriers, thus altering their concentration in one or more physiological compartments. There are many different types of BTB transporters, and it will be understood that compositions and methods of the invention may involve one or more than one BTB transporter. Other mechanisms may also be involved.

In some embodiments, the invention provides methods and compositions that modulate ATP Binding Cassette (ABC) transport proteins. ABC transport proteins is a superfamily of membrane transporters with similar structural features. These transport proteins are widely distributed in prokaryotic and eukaryotic cells. They are critical in the maintenance of barrier to foreign molecules and removal of waste from privileged spaces, and may be overexpressed in certain glial tumors conferring drug resistance to cytotoxic drugs. 48 members of the superfamily are described. There are 7 major subfamilies, which include ABC A-G. Subfamilies C, B, and G play a role in transport activity at, e.g., the blood brain barrier and blood-CSF barrier. ABC A substrates include lipids and cholesterol; ABC B transporters include P-glycoprotein (P-gP) and other multi drug resistance proteins (MRPs); ABC C contains MRP proteins; ABC E are expressed in ovary, testis and spleen; and ABC G contains breast cancer resistance protein (BCRP).

Other examples of blood-tissue barrier transporters that can be modulated by methods and compositions of the invention include organic anion transport systems (OAT), and the GABA transporters GAT-1 and GAT2/BGT-1. Substrate compounds for OATs include enkephalins and deltorphin II, anionic compounds, indomethacin, salicylic acid and cimetidine. OATs are inhibited by baclofen, tagamet, indomethacin, etc. and transport HVA (dopamine metabolite) and metabolites of norepinephrine, epinephrine, 5-HT3, and histamine.

GABA transporters are Na and Cl dependent, and are specific for GABA, taurine, β alanine, betaine, and nipecotic acid. GAT2 transporters are localized to abluminal and luminal surfaces of capillary endothelial cells. GAT-1 is localized to the outside of neurons and glia. GABA-transporter substrates include lorazepam, midazolam, diazepam, clonazepam and baclofen. Probenecid inhibits luminal membrane GABA transporters from capillary endothelial cells. GAT-1 is inhibited by Tiagabine.

P-glycoprotein

In some embodiments, the invention provides methods and compositions that modulate P-gP, e.g., that activate P-gP. P-gP, also known as ABCB1, forms a protective barrier to pump away by excreting compounds into, e.g., bile, urine, and intestinal lumen. Three isoforms have been identified in rodents (mdr1a, mdr1b, mdr2) and two in humans (MDR1 and MDR2). It is expressed in epithelium of the brain choroid plexus (which forms the blood cerebrospinal fluid barrier), as well as on the luminal surface of blood capillaries of the brain (blood-brain barrier) and other tissues known to have blood-tissue barriers, such as the placenta, the ovaries, and the testes.

In the brain, P-gP is expressed in multiple cell types within brain parenchyma including astrocytes and microglia and in luminal plasma membrane of capillary endothelium where it acts as a barrier to entry and efflux pump activity. P-gP transports a wide range of substrates out of cerebral endothelial cells into vascular lumen. P-gP is also expressed in the apical membrane of the choroid plexus and may transport substances into CSF.

P-gP substrates include molecules that tend to be lipophilic, planar molecules or uncharged or positively charged molecules. Non-limiting examples include organic cations, weak organic bases, organic anions and other uncharged compounds, including polypeptides and peptide derivatives, aldosterone, anthracyclines, colchicine, dexamethasone, digoxin, diltiazem, HIV protease inhibitors, loperamide, MTX, tacrolimus, morphine, ondansetron, phenyloin and β-blockers. Inhibitors of P-gP include quinidine, verapamil, rifampin, PSC 833 (see Schinkel, J. Clin Invest., 1996, herein incorporated by reference in its entirety) cyclosporine A, carbamazepine, and amitryptiline.

Multi-drug resistance protein (MRP) substrates include acetaminophen glucuronide, protease inhibitors, methotrexate and ampicillin. Inhibitors of MRP include buthionine sulphoximine, an inhibitor of glutathione biosynthesis.

Breast Cancer Resistant Protein (BCRP)

BCRP, an ATP-driven transporter, is highly expressed, e.g., in the placenta. Allikmets R., et al., Cancer Res. 58:5337-5339 (1998), herein incorporated by reference. BCRP is responsible for rendering tumor cells resistant to chemotherapeutic agents, such as topotecan, mitoxantrone, doxorubicin and daunorubicin. Allen J D, et al., Cancer Res. 59:4237-4241 (1999). BCRP has also been shown to restrict the passage of topotecan and mitoxantrone to the fetus in mice. Jonker J W et al., J. Natl. Cancer Inst. 92:1651-1656 (2000), herein incorporated by reference.

Monoamine Transporters

Monoamine transporters include serotonin transporter (SERT), norepinephrine transporter (NET) and the extraneuronal monoamine transporter (OCT3). Ramamoorthy S, et al., Placenta 14:449-461 (1993); Ramamoorthy S., et al., Biochem. 32:1346-1353 (1993); Kekuda R., et al., J. Biol. Chem. 273:15971-15979 (1998), all herein incorporated by reference.

Organic Cation Transporters

Organic Cation Transporters also exist, e.g., in the placenta. Placental Na+-driven organic cation transporter 2 (OCTN2) has been identified and localized to the basal membrane of the synctiotrophoblast. Wu X et al., J. Pharmacol. Exp. Ther. 290:1482-1492 (1999), herein incorporated by reference. Placental OCTN2 transports carnitine across the placenta in the direction of the material-to-fetal transfer. Ohashi R., et al., J. Pharmacol. Exp. Ther. 291:778-784 (1999), herein incorporated by reference. Studies have identified methamphetamine, quinidine, verapamil, pyrilamine, desipramine, dimethylamiloride, cimetidine, and procainimide as drug substrates for OCTN2. Wu X, et al., Biochem. Biophys. Res. Commun. 246:589-595 (1998); Wu X, et al., Biochim. Biophys. Acta 1466:315-327 (2000), herein incorporated by reference.

Monocarboxylate Transporters and the Dicarboxylate Transporters

Another type of BTB transporters include monocarboxylate (MCT) and dicarboxylate (NaDC3 transporters. Both MCT (e.g. lactate transport) and NaDC3 (e.g. succinate transport), which utilize electrochemical gradients for transport, are localized to the brush border membrane of the placenta, with MCT being expressed in the basal membrane to a lesser extent. Price N T, et al., Biochem. J. 329:321-328 (1998); Ganaphthy V, et al., Biochem J. 249:179-184 (1988); Balkovetz D F, et al., 263:13823-13830 (1988), all incorporated by reference herein. Valproic acid, a teratogenic substance, may be a substrate for MCT transfer, and compete with lactate for transport across the placental barrier. Nakamura H. et al., Pharm. Res. 19:154-161 (2002), herein incorporated by reference.

Further information on exemplary transporters that can be modulated in embodiments of the methods and compositions of the invention are provided in Tables 1 and 2, below.

TABLE 1

| Active Transporters found, e.g., in the Blood-Brain Barrier. | | |
|---|---|---|
| Active Transporter | Physiological Function in Blood-Brain Barrier | Exemplary Substrates |
| P-glycoprotein (P-gP) | Limits accumulation in kidney, islet cells, liver, and CNS of phospholipids, xenobiotics and other drugs; regulates absorption, distribution and elimination of drug substances. | Loperamide, tacrolimus, morphine, β endorphin, phenytoin, elavil, depakote, cyclosporine, protease inhibitors, digoxin, calcium channel blockers, vinca alkaloids, anthracyclines, ivermectin, aldosterone, hydrocortisone, dexamethasone, taxanes, domperidone, ondansetron |

TABLE 1-continued

Active Transporters found, e.g., in the Blood-Brain Barrier.

| Active Transporter | Physiological Function in Blood-Brain Barrier | Exemplary Substrates |
|---|---|---|
| Multidrug Resistance (MRP) Protein Family | MRP family members mediate ATP dependent transport of unconjugated, amphillic anions, and lipophillic compounds conjugated to glutathione, glucoronate, and sulfate; detoxification function s include extrusion of leukotriene metabolites; folate transport. | Acetaminophen glucuronide, protease inhibitors, methotrexate, ampicillin |
| GABA transporters (GAT-1 and GAT-2, BGT-1) | GAT1 drives GABA into neurons; mediates clearance of GABA from the brain | Lorazepam, midazolam, diazepam, clonazepam, baclofen |
| Organic Anion Transport (OAT) Systems | Limits thiopurine uptake; transports HVA (dopamine metabolite), and metabolites of norepinephrine, epinephrine, serotonin and histamine | opiate peptides, including enkephalin and deltorphin II, anionic compounds, indomethacin, salicylic acid, cimetide |

B. Blood Brain Barrier

Blood-tissue barriers may be illustrated by the blood brain barrier (BBB) and its mechanisms for controlling access to the CNS; however, it will be understood that the mechanisms described herein for the BBB are applicable, where appropriate, to other BTBs (especially in terms of transport proteins), and that the BBB is used as an illustrative example.

The access to the brain is controlled by at least two barriers, i.e., blood brain barrier (BBB) and blood-cerebrospinal fluid (CSF) barrier. As used herein, the term "blood brain-barrier" can encompass the blood-brain and blood-CSF barriers, unless otherwise indicated. The methods and compositions described herein are suitable for modulating the access of drugs and other substances into the brain. In some embodiments, the methods and compositions involve the modification of the blood brain barrier and/or blood-CSF barrier to prevent or reduce the entry of drugs into the central nervous system (CNS), e.g., by promoting efflux of the drugs from the CNS. In some embodiments, the compositions and methods of the invention utilize a modulator of a blood brain-barrier transport protein. In some embodiments, the compositions and methods of the invention utilize an activator of a blood brain-barrier transport protein.

The blood brain barrier regulates the transfer of substances between circulating blood and brain by facilitated transport and/or facilitated efflux. The interface on both luminal and abluminal surfaces contain physical and metabolic transporter components.

The exchange of substances between circulating blood and brain can be determined by evaluating octanol/H$_2$0 partition coefficient, facilitated transport, and/or facilitated efflux. The methods of measuring blood brain barrier integrity can be used to identify suitable central nervous system modulators for use in the methods and compositions described herein.

Various transporters exist to regulate rate of brain permeation for compounds with varying lipophilicity. Generally, hydrophilic nutrients, such as glucose and amino acids, are allowed entry into the physiological compartments of the methods and compositions disclosed herein. Conversely, compounds with low lipophilicity are pumped away from the physiological compartments by, for example, xenobiotic efflux transporters. These transporters are preferably modulated by the methods and compositions described herein to prevent entry of compounds and drugs into the central nervous system.

The blood CSF barrier is formed by the tight junctions of the epithelium of the choroid plexus and arachnoid membrane surrounding the brain and spinal cord. It is involved in micronutrient extraction, clearance of metabolic waste, and transport of drugs.

Mechanisms and routes of compounds into and out of brain include—paracellular aqueous pathway for water soluble agents, transcellular lipophilic pathway for lipid soluble agents, transport proteins for glucose, amino acids, purines, etc., specific receptor mediated endocytosis for insulin, transferrin, etc., adsorptive endocytosis for albumin, other plasma proteins, etc., and transporters (e.g., blood-brain barrier transport proteins) such as P-glycoprotein (P-gP), multi-drug resistance proteins (MRP), organic anion transporter (OAT) efflux pumps, gamma-aminobutyric acid (GABA) transporters and other transporters that modulate transport of drugs and other xenobiotics. Methods and compositions of the invention may involve modulation of one or more of these transporters. Preferably, the central nervous system modulators affect one or more of these mechanisms and routes to extrude drugs from the central nervous system.

The methods and compositions described herein also modulate other barriers, such as neuronal transport barriers, as well as other barriers.

Active Transporters

Another embodiment of the methods and compositions disclosed herein is use of a phosphorylated polyphenol, e.g. a phosphorylated pyrone analog such as a phosphorylated flavonoid, such as a phosphorylated quercetin and/or its metabolite in manipulating active transport of drugs, chemicals and other substances across the placental barrier. Active transport across the placental barrier, as opposed to facilitated diffusion or passive transport, requires energy, usually in the form of adenosine triphosphate (ATP) or through energy stored in the transmembrane electrochemical gradient provided by $Na^+$, $Cl^-$ or $H^+$. Because of the input of energy, active transport systems may work against a concentration gradient, however, saturation of the transporters can occur.

Extensive studies have been conducted regarding placental transport systems of nutrients, such as amino acids, vitamins and glucose. See Hahn T, et al., Early Pregnancy 2:168-182 (1996); Moe A J, Am. J. Physiol. 268:C1321-1331 (1995); Bissonnette J M, Mead Johnson Symp. Perinat. Dev. Med., 18:21-23 (1981), all incorporated herein by reference. Active transport of drugs occurs through the same transport systems, most likely due to structurally similarities between the transported drugs and endogenous substrates. Syme et al. (2004).

Active drug transporters are located either in the maternal-facing brush border (apical) membrane or the fetal-facing basolateral (basal) membrane where they pump drugs into or out of the synctiotrophoblast. Table 2 summarizes the active transporters that have been identified in the placenta.

TABLE 2

Active transporters found, e.g., in Placenta.

| Active Transporter | Physiological Function in Placenta | Exemplary Substrates |
|---|---|---|
| P-glycoprotein (P-gP) | Fetal-to-maternal transfer of hydrophobic cationic compounds | Digoxin, cyclosporine, saquinavir, vincristine, vinblastine, paclitaxel, dexamethasone, terfenadine, sirolimus, quinidine, ondansetron, loperamide |
| Multidrug resistance protein 1 (MRP1) | Fetal-to-maternal transfer of glutathione, sulfate and glucuronide conjugates (dianionic sulfated bile salts) | Methotrexate, etoposide, vincristine, cisplatin, vinblastine, HIV protease inhibitors |
| Multidrug resistance protein 2 (MRP2) | Fetal-to-maternal transfer of glutathione, sulfate and glucuronide conjugates (dianionic sulfated bile salts, bilirubin glucuronide, estradiol glucuronide) | Etoposide, cisplatin, doxorubicin, vincristine, vinblastine, methotrexate, paracetamol, glucuronide, grepafloxacin, ampilicillin |
| Multidrug resistance protein 3 (MRP3) | Fetal-to-maternal transfer of anionic conjugates | Methotrexate, etoposide |
| Breast cancer resistant protein (BCRP) | Unknown | Topotecan, mitoxantrone, doxorubicin, daunorubicin |
| Serotonin transporter (SERT) | Serotonin transfer | Amphetamines |
| Norepinephrine transporter (NET) | Dopamine and norepinephrine transfer | Amphetamines |
| Extraneuronal monoamine transporter (OCT3) | Serotonin, dopamine, norepinephrine, histamine transfer | Amphetamines, imipramine, desipramine, clonidine, cimetidine |
| Organic cation transporters (OCTN) | Maternal-to-fetal transfer of carnitine | Methamphetamine, quinidine, verapamil, pyrilamine |
| Monocarboxylate transporters | Fetal-to-maternal transfer of lactate and pyruvate | Valproic acid |
| Dicarboxylate transporters | Maternal-to-fetal transfer of succinate and α-ketoglutarate | Unknown |
| Sodium/multivitamin transporter (SMVT) | Maternal-to-fetal transfer of biotin and pantothenate | Carbamazepine, primidone |

IV. SUBSTANCES WHOSE EFFECTS ARE ENHANCED AND/OR WHOSE SIDE EFFECTS ARE DIMINISHED WHEN COMBINED WITH A PHOSPHORYLATED POLYPHENOL

In one aspect, the invention provides compositions and methods to reduce or eliminate one or more side effects of a substance. The substance may be produced in the subject in a normal or abnormal condition (e.g., beta amyloid in Alzheimer's disease). The substance may be an agent that is introduced into an animal, e.g., a therapeutic agent (e.g., an immunosuppressive to decrease rejection in organ transplant). It will be appreciated that some therapeutic agents are also agents produced naturally in an animal, and the two groups are not mutually exclusive. In some embodiments, the compositions and methods retain or enhance a desired effect of the substance, e.g., a peripheral effect. The methods and compositions of the invention apply to any therapeutic agent for which it is desired to reduce one or more side effects of the agent and/or enhance one or more of the therapeutic effects of the agent. In some embodiments, the compositions and methods of the invention utilize an immunomodulator such as an immunosuppressive agent. In some embodiments, the immunosuppressive agent is an calcineurin inhibitor. In some embodiments, the immunosuppressive is a non-calcineurin inhibitor. It will be appreciated that some agents that have primarily an immunosuppressive effect also have other therapeutic effects, while some agents that have primarily a non-immunosuppressive therapeutic effect also provide some degree of immunosuppression. The invention encompasses these therapeutic agents as well.

Hence, in some embodiments, the methods and compositions of the present invention can be used to modulate the effects of one or more of a variety of therapeutic agents. In some embodiments, the dosage of the therapeutic agent will be modulated according to the effect of the side effect modulator. For instance, less therapeutic agent may be needed to reach optimal effect when co-administered with the side effect modulator. In other embodiments co-administering the side effect modulator with a therapeutic agent will allow for chronically administering the drug without drug escalation and/or without dependence on the drug. In another embodiment co-administering the side effect modulator will allow for the elimination of a therapeutic agent from a physiological compartment, i.e. wash out drug in an overdose situation or to wake up a patient faster after anesthesia. In some embodiments, the physiological compartment is a central nervous system. In some embodiments, the physiological compartment is a fetal compartment.

The "side effect" of the therapeutic agent for which modulation is sought may be any effect associated with the agent that occurs in addition to the therapeutic effect. In some embodiments, the compositions and methods of the invention are used to decrease undesirable side effects and or increase desirable side effects or therapeutic effects of a therapeutic agent. Side effects are often specific to the agent, and are well-known in the art for various therapeutic agents. The effect may be acute or chronic. The effect may be biochemical, cellular, at the tissue level, at the organ level, at the multi-organ level, or at the level of the entire organism. The effect may manifest in one or more objective or subjective manners, any of which may be used to measure the effect.

An exemplary side effect, associated with many types of therapeutic agents, e.g., calcineurin inhibitor, is a central nervous system (CNS) effect. The term "central nervous system (CNS) effect," as used herein, encompasses any effect of a substance in the CNS. For some substances that may be normally or abnormally produced in the CNS, such as amyloid beta, the effect may be a pathological effect. In some embodiments, the side effect of a substance can be drowsiness, impaired concentration, sexual dysfunction, sleep disturbances, habituation, dependence, alteration of mood, respiratory depression, nausea, vomiting, lowered appetite, lassitude, lowered energy, dizziness, memory impairment, neuronal dysfunction, neuronal death, visual disturbances, impaired mentation, tolerance, addiction, hallucinations, lethargy, myoclonic jerking, or endocrinopathies, or combinations thereof.

Other exemplary side effects include hypogonadism (e.g., lowered testosterone) and hyperglycemia associated with some therapeutic agents, e.g., immunosuppressants agents such as calcineurin inhibitors, e.g., tacrolimus. In some embodiments, the side effect is a renal and/or urogenital side effect, for example, nephrotoxicity, renal function impairment, creatinine increase, urinary tract infection, oliguria, cystitis haemorrhagic, hemolytic-uremic syndrome or micturition disorder, as well as other effects mention herein, or combinations thereof. In some embodiments, side effect is a hepatic, pancreatic and/or gastrointestinal side effect such as necrosis, hepatotoxicity, liver fatty, venoocclusive liver disease, diarrhea, nausea, constipation, vomiting, dyspepsia, anorexia, or LFT abnormal, as well as other effects mention herein, or combinations thereof. Other side effects are described, for example in U.S. published Patent Applications US2006/0111308 and US2008/0161248; and PCT published Patent Applications WO/06055672 and WO/08083160, all of which are incorporated by reference herein in their entirety.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

The term "in need of treatment" encompasses both therapeutic and prophylactic treatment. Thus, for example, and animal would be in need of treatment if the treatment would provide a prophylactic benefit, for instance where the animal is at risk of developing a disease or condition.

The term "physiological compartment" as used herein includes physiological structures, such as organs or organ groups or the fetal compartment, or spaces whereby a physiological or chemical barrier exists to exclude compounds or agents from the internal portion of the physiological structure or space. Such physiological compartments include the central nervous system, the fetal compartment and internal structures contained within organs, such as the ovaries and testes.

Therapeutic agents that may be used in compositions and methods of the invention include immunosuppressive agents, such as calcineurin inhibitors, e.g. tacrolimus, sirolimus, and the like, other immunomodulators, antineoplastics, amphetamines, antihypertensives, vasodilators, barbiturates, membrane stabilizers, cardiac stabilizers, glucocorticoids, antilipedemics, antiglycemics, cannabinoids, antidipressants, antineuroleptics, chemotherapeutic agents, antiinfectives, tolerogen, immunostimulants, drug acting on the blood and the blood-forming organs, hematopoietic agent, growth factor, mineral, and vitamin, anticoagulant, thrombolytic, antiplatelet drug, hormone, hormone antagonist, pituitary hormone, thyroid and antithyroid drug, estrogen and progestin, androgen, adrenocorticotropic hormone; adrenocortical steroid and synthetic analogs, insulin, oral hypoglycemic agents, calcium, phosphate, parathyroid hormone, vitamin D, calcitonin, and other compounds. Therapeutic agents of use in the invention are further described in U.S. Patent Publication No. US2006/0111308, in particular at paragraphs [0123]-[0164]; and PCT Publication No. WO/06055672, in particular at paragraphs [00109]-[00145].

In some embodiments the therapeutic agent whose side effect is reduced and/or whose effectiveness is improved in the presence of the phosphorylated pyrone analog is an immunosuppressant. The immunosuppressants can be a cyclosporin (Neoral, Sandimmune, SangCya), an azathioprine (Imuran), a corticosteroid such as prednisolone (Deltasone, Orasone), basiliximab (Simulect), daclizumab (Zenapax), muromonab CD3 (Orthoclone OKT3), tacrolimus (Prograf®), ascomycin, pimecrolimus (Elidel), azathioprine (Imuran), cyclosporin (Sandimmune, Neoral), glatiramer acetate (Copaxone), mycophenolate (CellCept), sirolimus (Rapamune), voclosporin In some embodiments the therapeutic agent is a calcineurin inhibitor such as tacrolimus (Prograf®), The therapeutic agent can be a selective estrogen receptor modulator (SERM), such as tamoxifen.

The therapeutic agent can be an antilipedimic agent such as an HMG-CoA inhibitor such as lovastatin, simvastatin, pravastatin, fluvastatin, or atorvastatin The therapeutic agent can be an antihyperglycemic agent (antiglycemic, hypoglycemic agent) such as glyburide, glipizide, gliclazide, or glimepride; a meglitinide such as repaglinide or netaglinide, a biguanide such as metformin, a thiazolidinedione, an α-glucosidase inhibitor such as acarbose or miglitol, glucagon, somatostatin, or diazoxide.

The therapeutic agent can be, in some embodiments, a cannabinoid.

The therapeutic agent can be an antidepressant. In some embodiments, antidepressants cause the side effects of high blood sugar and diabetes. The compounds and methods of the invention can be used, for example to reduce these side effects. In some embodiments the therapeutic agent is an antidepressant selected from the group of aripiprazone (Abilify), nefazodone (Serzone), escitalopram oxalate (Lexapro), sertraline (Zoloft), escitalopram (Lexapro), fluoxetine (Prozac), bupropion (Wellbutrin, Zyban), paroxetine (Paxil), venlafaxine (Effexor), trazodone (Desyrel), amitriptyline (Elavil), citalopram (Celexa), duloxetine (Cymbalta), mirtazapine (Remeron), nortriptyline (Pamelor), imipramine (Tofranil), amitriptyline (Elavil), clomipramine (Anafranil), doxepin (Adapin), trimipramine (Surmontil), amoxapine (Asenidin), desipramine (Norpramin), maprotiline (Ludiomil), protryptiline (Vivactil), citalopram (Celexa), fluvoxamine (Luvox), phenelzine (Nardil), trancylpromine (Pamate), selegiline (Eldepryl).

In some embodiments the therapeutic agent is an antineuropathic agent such as gabapentin.

The therapeutic agent can be an anticonvulsant. In some cases, it can be an anticonvulsant that also has efficacy in the treatment of pain. The therapeutic agent can be, for example, acetazolamide (Diamox), carbamazepine (Tegretol), clobazam (Frisium), clonazepam (Klonopin/Rivotril), clorazepate (Tranxene-SD), diazepam (Valium), divalproex sodium (Depakote), ethosuximide (Zarontin), ethotoin (Peganone), felbamate (Felbatol), fosphenyloin (Cerebyx), gabapentin (Neurontin), lamotrigine (Lamictal), levetiracetam (Keppra), lorezepam (Ativan), mephenyloin (Mesantoin), metharbital (Gemonil), methsuximide (Celontin). Methazolamide (Neptazane), oxcarbazepine (Trileptal), phenobarbital, phenyloin (Dilantin/Epanutin), phensuximide (Milontin), pregabalin (Lyrica), primidone (Mysoline), sodium valproate (Epilim), stiripentol (Diacomit), tiagabine (Gabitril), topiramate (Topamax), trimethadione (Tridione), valproic acid (Depakene/Convulex), vigabatrin (Sabril), zonisamide (Zonegran), or cefepime hydrochloride (Maxipime).

Thus compositions and methods of the invention encompass the use of one or more therapeutic agents in combination with a phosphorylated pyrone analog such as a phosphorylated flavonoid, such as a phosphorylated quercetin, phosphorylated fisetin, or phosphorylated 5,7-dideoxyquercetin, that reduces a side effect of the therapeutic agent.

One embodiment of the invention is a composition comprising an ionic complex comprising an opiate and a phosphorylated polyphenol. In some embodiments the ionic compound comprises a cationic opiate associated with an anionic phosphorylated polyphenol. In some embodiments, the compound comprises a salt of the opiate and the polyphenol. In some embodiments the ionic complex is between a phosphorylated polyphenol, e.g. a phosphorylated pyrone analog such as a phosphorylated flavonoid and morphine. In some embodiments, the ionic complex the ionic complex of a phosphorylated quercetin and oxycodone. In some embodiments, the ionic complex is the ionic complex of a phosphorylated quercetin and hydrocodone. In some embodiments, the ionic complex is the ionic complex of a phosphorylated quercetin and fentanyl. In some embodiments, the ionic complex is the ionic complex of a phosphorylated quercetin and levorphenol. In some embodiments, the ionic complex is the ionic complex of a phosphorylated quercetin and oxymorphone. Another embodiment of the invention is a composition comprising an ionic complex comprising an immunosuppressant and a phosphorylated polyphenol. In some embodiments, the ionic complex is the ionic complex of a phosphorylated quercetin and mycophenolate.

In some embodiments, the ionic complex of the opiate or immunosuppressant and a phosphorylated polyphenol is in a solid form. In some embodiments, the ionic complex of the opiate or immunosuppressant and a phosphorylated polyphenol is in a crystalline form, an amorphous form, or a mixture of crystalline and amorphous forms. In some embodiments the ionic complex is in a crystalline or amorphous form containing waters of hydration.

In some embodiments, the ionic complex is present in a composition where the molar ratio of one or more of the opiate or immunosuppressant to the phosphorylated polyphenol, e.g. a phosphorylated pyrone analog such as a phosphorylated flavonoid, such as a phosphorylated quercetin is about 0.0001:1 to 1:1. Without limiting the scope of the invention, the molar ratio of the immunosuppressant or opiate to the phosphorylated polyphenol, e.g. a phosphorylated pyrone analog such as a phosphorylated flavonoid, such as a phosphorylated quercetin can be about 0.0001:1 to about 10:1, or about 0.001:1 to about 5:1, or about 0.01:1 to about 5:1, or about 0.1:1 to about 2:1, or about 0.2:1 to about 2:1, or about 0.5:1 to about 2:1, or about 0.1:1 to about 1:1.

In some embodiments, the compositions and methods of the invention utilize an antihypertensive agent. In some embodiments, the compositions and methods of the invention utilize an immunosuppressive agent. The therapeutic agent may also be a chemotherapeutic agent, a vasodilator, a cardiac glycoside, a diuretic agent, a bronchodilator, a corticosteroid, a sedative-hypnotic, an antiepileptic drug, a general anesthetic, a skeletal muscle relaxant, an antipsychotic agent, an anti-hyperlipidemic agent, a non-steroidal antiinflammatory drug, an antidiabetic agent, an antimicrobial agent, an antifungal agent, an antiviral agent, or an antiprotozoal agent. It will be appreciated that there is some overlap between these groups, e.g., some agents that have primarily an immunosuppressive effect also have other therapeutic effects, while some agents that have primarily a non-immunosuppressive effect also provide some degree of analgesia. The invention encompasses these therapeutic agents as well. Additional suitable drugs may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments the therapeutic agent is an immunomodulator, e.g., an immunosuppressive agent such as a calcineurin inhibitor. In some embodiments, the compositions and methods of the invention utilize cyclosporin A (CsA). In some embodiments, the compositions and methods of the invention utilize tacrolimus. In some embodiments, the calcineurin inhibitor is tacrolimus analog. In some embodiments, the tacrolimus analog is selected from the group consisting of meridamycin, 31-O-Demethyl-FK506; L-683,590, L-685,818; 32-O-(1-hydroxyethylindol-5-yl)ascomycin; ascomycin; C18-OH-ascomycin; 9-deoxo-31-O-demethyl-FK506; L-688,617; A-119435; AP1903; rapamycin; dexamethasone-FK506 heterodimer; 13-O-demethyl tacrolimus; and FK 506-dextran conjugate. In some embodiments, the immunosuppressive agent is sirolimus, tacrolimus, mycophenolate, methadone, cyclosporin, prednisone, or voclosporin.

V. COMPOSITIONS

In one aspect the invention provides compositions that include a phosphorylated polyphenol e.g. phosphorylated pyrone analog such as a phosphorylated flavonoid, such as a phosphorylated quercetin, phosphorylated fisetin, or phosphorylated 5,7-dideoxyquercetin, that reduces or eliminates side effect of one or more substances. In some embodiments, the substance is a therapeutic agent with which the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is co-administered. "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present, and combinations thereof.

In some embodiments, the invention provides compositions containing a combination of a therapeutic agent and an agent that reduces or eliminates a side effect of the therapeutic agent. In some embodiments the invention provides pharmaceutical compositions that further include a pharmaceutically acceptable excipient. In some embodiments, the pharmaceutical compositions are suitable for oral administration. In some embodiments, the pharmaceutical compositions are suitable for transdermal administration. In some embodiments, the pharmaceutical compositions are suitable for injection. Other forms of administration are also compatible with embodiments of the pharmaceutical compositions of the invention, as described herein.

In some embodiments, the reduction or elimination of side effects is due to the modulation of a BTB transport protein by a phosphorylated polyphenol e.g. phosphorylated pyrone analog such as a phosphorylated flavonoid, such as a phosphorylated quercetin, phosphorylated fisetin, or phosphorylated 5,7-dideoxyquercetin and/or its metabolite. In some embodiments, the BTB transport protein is an ABC transport protein. In some embodiments, the BTB transport protein modulator is a BTB transport protein activator. In some embodiments, the BTB transport protein modulator is a modulator of P-gP.

In some embodiments, the side effect modulator comprises a phosphorylated polyphenol and/or its metabolite that acts as a BTB transport protein modulator. In other embodiments, the side effect modulator comprises a phosphorylated polyphenol and/or its metabolite which acts to lower a side effect of a therapeutic agent through a non-BTB transport protein-mediated mechanism, or that acts to lower a side effect of a therapeutic agent through a BTB transport protein-mediated mechanism and a non-BTB transport protein-mediated mechanism, is used. In some embodiments utilizing a phosphorylated polyphenol, the phosphorylated polyphenol is a phosphorylated pyrone analog such as a phosphorylated flavonoid. In some embodiments utilizing a phosphorylated polyphenol, the phosphorylated polyphenol is selected from the group consisting of phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, and phosphorylated epicatechin. In some embodiments utilizing a polyphenol, the polyphenol is a phosphorylated flavonol. In certain embodiments, the phosphorylated flavonol is selected from the group consisting of phosphorylated quercetin, phosphorylated fisetin, phosphorylated 5,7-dideoxyquercetin, phosphorylated galangin, and phosphorylated kaempferol, or combinations thereof. In some embodiments, the phosphorylated flavonol is phosphorylated quercetin. In some embodiments, the phosphorylated flavonol is phosphorylated galangin. In some embodiments, the phosphorylated flavonol is phosphorylated kaempferol. In some embodiments, the phosphorylated flavonol is phosphorylated fisetin. In some embodiments, the phosphorylated flavonol is phosphorylated 5,7-dideoxyquercetin. In some embodiments, the phosphorylated flavonol is quercetin-3'-O-phosphate.

In embodiments in which the side effect is a side effect of the therapeutic agent that is reduced is selected from the group consisting of drowsiness, impaired concentration, sexual dysfunction, sleep disturbances, habituation, dependence, alteration of mood, respiratory depression, nausea, vomiting, lowered appetite, lassitude, lowered energy, dizziness, memory impairment, neuronal dysfunction, neuronal death, visual disturbance, impaired mentation, tolerance, addiction, hallucinations, lethargy, myoclonic jerking, endocrinopathies, and combinations thereof. In some embodiments, the side effect of the therapeutic agent that is reduced is selected from the group consisting of impaired concentration and sleep disturbances. In some embodiments, the side effect of the therapeutic agent that is reduced is impaired concentration. In some embodiments, the side effect of the therapeutic agent that is reduced is sleep disturbances. In some embodiments, the side effect is a renal and/or urogenital side effect selected from the group consisting of nephrotoxicity, renal function impairment, creatinine increase, urinary tract infection, oliguria, cystitis haemorrhagic, hemolytic-uremic syndrome or micturition disorder, as well as other effects mention herein, and combinations thereof. In some embodiments, the side effect is a hepatic, pancreatic and/or gastrointestinal side effect selected from the group consisting of hepatic necrosis, hepatotoxicity, liver fatty, venoocclusive liver disease, diarrhea, nausea, constipation, vomiting, dyspepsia, anorexia, and LFT abnormal, as well as other effects mention herein, and combinations thereof In some embodiments, the therapeutic agent is an immunosuppressant. The immunosuppressant can be, for example, a calcineurin inhibitor, e.g., tacrolimus or a tacrolimus analog. The immunosuppressant can be, for example, sirolimus, tacrolimus, mycophenolate, methadone, cyclosporin, prednisone, or voclosporin. In some embodiments, the therapeutic agent is an agent selected from the group of: antivirals, antibiotics, antineoplastics, amphetamines, antihypertensives, vasodilators, barbiturates, membrane stabilizers, cardiac stabilizers, glucocorticoids, antilipedemics, antiglycemics, cannabinoids, antidipressants, antineuroleptics, and antiinfectives. In some embodiments, the therapeutic agent is an antihypertensive. In some embodiments, the therapeutic agent is an antiinfective.

In some embodiments, the invention provides a composition containing a therapeutic agent and an phosphorylated polyphenol e.g. phosphorylated pyrone analog such as a phosphorylated flavonoid, such as a phosphorylated quercetin, phosphorylated fisetin, phosphorylated 5,7-dideoxyquercetin, where the therapeutic agent is present in an amount sufficient to exert a therapeutic effect and the phosphorylated polyphenol e.g. phosphorylated pyrone analog such as a phosphorylated flavonoid, such as a phosphorylated quercetin, phosphorylated fisetin, phosphorylated 5,7-dideoxyquercetin and/or its metabolite is present in an amount sufficient to decrease a side effect of the therapeutic agent by a measurable amount, compared to the side effect without the phosphorylated polyphenol, when the composition is administered to an animal. In some embodiments, a side effect of the therapeutic agent is decreased by an average of at least about 1, 5, 10, 15, 20, 25, 30, 35, 40, 45, 50, 55, 60, 65, 70, 75, 80, 85, 90, 95, or more than 95%, compared to the side effect without the phosphorylated polyphenol. In some embodiments, a side effect of the therapeutic agent is decreased by an average of at least about 5%, compared to the side effect without the phosphorylated polyphenol. In some embodiments, a side effect of the therapeutic agent is decreased by an average of at least about 10%, compared to the side effect without the phosphorylated polyphenol. In some embodiments, a side effect of the therapeutic agent is decreased by an average of at least about 15%, compared to the side effect without the phosphorylated polyphenol. In some embodiments, a side effect of the therapeutic agent is decreased by an average of at least about 20%, compared to the side effect without the phosphorylated polyphenol. In some embodiments, a side effect is substantially eliminated compared to the side effect without the phosphorylated polyphenol. "Substantially eliminated" as used herein encompasses no measurable or no statistically significant side effect (one or more side effects) of the therapeutic agent, when administered in combination with the phosphorylated polyphenol, e.g. phosphorylated pyrone analog such as a phosphorylated flavonoid, such as a phosphorylated quercetin, phosphorylated fisetin, or phosphorylated 5,7-dideoxyquercetin.

Thus, in some embodiments, the invention provides compositions that contain a phosphorylated polyphenol, e.g., a phosphorylated pyrone analog such as a phosphorylated flavonoid, such as a phosphorylated quercetin, phosphorylated fisetin, or phosphorylated 5,7-dideoxyquercetin, and an immunosuppressive agent, e.g., tacrolimus or sirolimus, where the immunosuppressive agent is present in an amount sufficient to exert an immunosuppressive effect and the phosphorylated polyphenol, e.g. phosphorylated pyrone analog such as a phosphorylated flavonoid, such as a phosphorylated quercetin, phosphorylated fisetin, or phosphorylated 5,7-dideoxyquercetin is present in an amount sufficient to decrease side effect of the immunosuppressive agent by a measurable amount, compared to the side effect without the phosphorylated polyphenol, when the composition is administered to an animal. For further description of immunosuppressive agents that may be used in the compositions of the invention, see U.S. Patent Publication No. US2006/0111308, particularly at paragraphs [0130]-[0154], and PCT published Patent Application WO/06055672, particularly at paragraphs [00116]-[00136]. The measurable amount may be an average of at least about 1, 5, 10, 15, 20, 25, 30, 35, 40, 45, 50, 55, 60, 65, 70, 75, 80, 85, 90, 95, or more than 95%, compared to the side effect without the phosphorylated polyphenol. In some embodiments, the side effect is disturbance of concentration. In some embodiments, the side effect is sleep disturbances.

In some embodiments, the invention provides compositions that contain a phosphorylated flavonol that is phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin, or a combination thereof.

In some embodiments, the invention provides compositions that contains phosphorylated quercetin, phosphorylated fisetin, or phosphorylated 5,7-dideoxyquercetin and an immunosuppressant, e.g., tacrolimus (FK-506) where the immunosuppressant, e.g., tacrolimus is present in an amount sufficient to exert an immunosuppressant effect and the phosphorylated quercetin, phosphorylated fisetin, or phosphorylated 5,7-dideoxyquercetin is present in an amount sufficient to decrease a side effect, or hyperglycemia of the immunosuppressant, e.g., tacrolimus by a measurable amount, compared to the side effect without the phosphorylated quercetin, phosphorylated fisetin, or phosphorylated 5,7-dideoxyquercetin when the composition is administered to an animal. The measurable amount may be an average of at least about 1, 5, 10, 15, 20, 25, 30, 35, 40, 45, 50, 55, 60, 65, 70, 75, 80, 85, 90, 95, or more than 95%, compared to the side effect without the phosphorylated polyphenol. The side effect may be any side effect as described herein. In some embodiments, the side effect is hyperglycemia. In some embodiments, the side effect is a tissue specific effect.

In some embodiments, the phosphorylated polyphenol, e.g. phosphorylated pyrone analog such as a phosphorylated flavonoid, such as a phosphorylated quercetin, phosphorylated fisetin, or phosphorylated 5,7-dideoxyquercetin and or its metabolite is a side effect modulator, e.g. BTB transport protein modulator, which is present in an amount sufficient to decrease a side effect of the therapeutic agent by a measurable amount and to increase a therapeutic effect of the therapeutic agent by a measurable amount, compared to the side effect and therapeutic effect without the side effect modulator, e.g. BTB transport protein modulator, when the composition is administered to an animal. In some embodiments, a therapeutic effect of the therapeutic agent is increased by an average of at least about 1, 5, 10, 15, 20, 25, 30, 35, 40, 45, 50, 55, 60, 65, 70, 75, 80, 85, 90, 95, or more than 95%, compared to the therapeutic effect without the side effect modulator, e.g. BTB transport protein modulator. In some embodiments, a therapeutic effect of the therapeutic agent is increased by an average of at least about 5%, compared to the therapeutic effect without the side effect modulator, e.g. BTB transport protein modulator. In some embodiments, a therapeutic effect of the therapeutic agent is increased by an average of at least about 10%, compared to the therapeutic effect without the side effect modulator, e.g. BTB transport protein modulator. In some embodiments, a therapeutic effect of the therapeutic agent is increased by an average of at least about 15%, compared to the therapeutic effect without the side effect modulator, e.g. BTB transport protein modulator. In some embodiments, a therapeutic effect of the therapeutic agent is increased by an average of at least about 20%, compared to the therapeutic effect without the side effect modulator, e.g. BTB transport protein modulator. In some embodiments, a therapeutic effect of the therapeutic agent is increased by an average of at least about 30%, compared to the therapeutic effect without the side effect modulator, e.g. BTB transport protein modulator. In some embodiments, a therapeutic effect of the therapeutic agent is increased by an average of at least about 40%, compared to the therapeutic effect without the side effect modulator, e.g. BTB transport protein modulator. In some embodiments, a therapeutic effect of the therapeutic agent is increased by an average of at least about 50%, compared to the therapeutic effect without the side effect modulator, e.g. BTB transport protein modulator.

In some embodiments, the invention provides compositions containing a phosphorylated polyphenol, e.g. phosphorylated pyrone analog such as a phosphorylated flavonoid, such as phosphorylated quercetin, phosphorylated fisetin, or phosphorylated 5,7-dideoxyquercetin, present in an amount sufficient to decrease side effect of a therapeutic agent by an average of at least about 5% and to increase a therapeutic effect of the therapeutic agent by an average of at least about 5%, when the composition is administered to an animal in combination with the therapeutic agent, compared to the side effect and therapeutic effect without the phosphorylated polyphenol. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease a side effect of a therapeutic agent by an average of at least about 10% and to increase a therapeutic effect of the therapeutic agent by an average of at least about 10%, when the composition is administered to an animal in combination with the therapeutic agent, compared to the side effect and therapeutic effect when the therapeutic agent is administered without the a phosphorylated polyphenol, e.g. phosphorylated pyrone analog such as a phosphorylated flavonoid such as phosphorylated quercetin, phosphorylated fisetin, or phosphorylated 5,7-dideoxyquercetin. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease a side effect of a therapeutic agent by an average of at least about 20% and to increase a therapeutic effect of the therapeutic agent by an average of at least about 20%, when the composition is administered to an animal in combination with the therapeutic agent, compared to the side effect and therapeutic effect when the therapeutic agent is administered without the a phosphorylated polyphenol, e.g. phosphorylated pyrone analog such as a phosphorylated flavonoid such as phosphorylated quercetin, phosphorylated fisetin, or phosphorylated 5,7-dideoxyquercetin. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease a side effect of a therapeutic agent by an average of at least about 10% and to increase a therapeutic effect of the therapeutic agent by an average of at least about 20%, when the composition is administered to an animal in combination with the therapeutic agent, compared to the side effect and therapeutic effect when the therapeutic agent is administered without the a phosphorylated polyphenol, e.g. phosphorylated pyrone analog such as a phosphorylated flavonoid such as phosphorylated quercetin, phosphorylated fisetin, or phosphorylated 5,7-dideoxyquercetin. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease a side effect of a therapeutic agent by an average of at least about 10% and to increase a therapeutic effect of the therapeutic agent by an average of at least about 30%, when the composition is administered to an animal in combination with the therapeutic agent, compared to the side effect and therapeutic effect when the therapeutic agent is administered without the phosphorylated polyphenol. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease aside effect of a therapeutic agent by an average of at least about 10% and to increase a therapeutic effect of the therapeutic agent by an average of at least about 40%, when the composition is administered to an animal in combination with the therapeutic agent, compared to the side effect and therapeutic effect when the therapeutic agent is administered without the phosphorylated polyphenol. In some embodiments, the invention provides compositions containing a phosphorylated polyphenol, e.g. phosphorylated pyrone analog such as a phosphorylated flavonoid such as phosphorylated quercetin, phosphorylated fisetin, or phosphorylated 5,7-dideoxyquercetin present in an amount sufficient to decrease a side effect of a therapeutic agent by an average of at least about 10% and to increase a therapeutic effect of the therapeutic agent by an average of at least about 50%, when the composition is administered to an animal in combination with the therapeutic agent, compared to the side effect and therapeutic effect when the therapeutic agent is administered without the a phosphorylated polyphenol, e.g. phosphorylated pyrone analog such as a phosphorylated flavonoid such as phosphorylated quercetin, phosphorylated fisetin, or phosphorylated 5,7-dideoxyquercetin.

In exemplary embodiments, the invention provides a composition that contains a phosphorylated polyphenol that is phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin, or combinations thereof, and an immunosuppressive, such as an calcineurin inhibitor, e.g., tacrolimus or sirolimus, where the immunosuppressive agent is present in an amount sufficient to exert an immunosuppressive effect, and the phosphorylated polyphenol is present in an amount effective to decrease a side effect of the immunosuppressive agent by a measurable amount (e.g., an average of at least about 1, 5, 10, 15, 20, 25, 30, 35, 40, 45, 50, 55, 60, 65, 70, 75, 80, 85, 90, 95, or more than 95%) and to increase the immunosuppressive effect of the immunosuppressive agent by a measurable amount (e.g., an average of at least about 1, 5, 10, 15, 20, 25, 30, 35, 40, 45, 50, 55, 60, 65, 70, 75, 80, 85, 90, 95, or more than 95%). The side effect may be any side effect as described herein. In some embodiments, the side effect is hyperglycemia. In some embodiments, the side effect is a renal side effect. In some embodiments, the side effect is nephrotoxicity. In some embodiments, the side effect is decrease in metabolic function. In yet further exemplary embodiments, the invention provides a composition that contains a phosphorylated flavonol that is phosphorylated quercetin, phosphorylated fisetin, phosphorylated 5,7-dideoxyquercetin, phosphorylated galangin, or phosphorylated kaempferol and an immunosuppressive that is tacrolimus, sirolimus, mycophenolate, methadone, cyclosporin, prednisone, or voclosporin, where the immunosuppressive is present in an amount sufficient to exert an immunosuppressive effect, and the phosphorylated flavonol is present in an amount effective to decrease a side effect of the immunosuppressive agent by a measurable amount (e.g., an average of at least about 1, 5, 10, 15, 20, 25, 30, 35, 40, 45, 50, 55, 60, 65, 70, 75, 80, 85, 90, 95, or more than 95%) and to increase the immunosuppressive effect of the immunosuppressive agent by a measurable amount (e.g., an average of at least about 1, 5, 10, 15, 20, 25, 30, 35, 40, 45, 50, 55, 60, 65, 70, 75, 80, 85, 90, 95, or more than 95%). The side effect may be any side effect as described herein. In some embodiments, the side effect is hyperglycemia. In some embodiments, the side effect is a renal side effect. In some embodiments, the side effect is nephrotoxicity. In some embodiments, the side effect is decrease in metabolic function.

An "average" as used herein is preferably calculated in a set of normal human subjects, this set being at least about 3 human subjects, preferably at least about 5 human subjects, preferably at least about 10 human subjects, even more preferably at least about 25 human subjects, and most preferably at least about 50 human subjects.

In some embodiments, the invention provides a composition that contains a therapeutic agent and a phosphorylated polyphenol e.g. phosphorylated pyrone analog such as a phosphorylated flavonoid, such as a phosphorylated quercetin, phosphorylated fisetin, or phosphorylated 5,7-dideoxyquercetin. In some embodiments, the concentration of the therapeutic agents is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v in the composition. In some embodiments, the concentration of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v in the composition.

In some embodiments, a concentration of the therapeutic agent is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v in the composition. In some embodiments, a concentration of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17 The invention provides methods of treating tissue rejection, using therapeutic agents and the phosphorylated compositions of the invention. Any suitable type of tissue rejection, whether acute or chronic, may be treated by the methods of the invention. Thus, in some embodiments, the invention provides a method of treating an animal for graft protection by administering to an animal at risk of tissue rejection an effective amount of an immunosuppressive agent, e.g. an calcineurin inhibitor such as tacrolimus or sirolimus and an amount of a phosphorylated polyphenol e.g. phosphorylated pyrone analog such as a phosphorylated flavonoid, such as a phosphorylated quercetin, phosphorylated fisetin, or phosphorylated 5,7-dideoxyquercetin sufficient to reduce a side effect of the immunosuppressive agent.

In some embodiments, a concentration of the therapeutic agent is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v in the composition. In some embodiments, a concentration of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v in the composition.

In some embodiments, a concentration of the therapeutic agent is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v in the composition. In some embodiments, a concentration of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v in the composition.

In some embodiments, an amount of the therapeutic agent is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g in the composition. In some embodiments, an amount of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g in the composition.

In some embodiments, an amount of the therapeutic agent is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g in the composition. In some embodiments, an amount of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g in the composition.

In some embodiments, an amount the therapeutic agent is in the range of 0.0001-10 g, 0.0005-9 g, 0.001-8 g, 0.005-7 g, 0.01-6 g, 0.05-5 g, 0.1-4 g, 0.5-4 g, or 1-3 g in the composition. In some embodiments, an amount of the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is in the range of 0.0001-10 g, 0.0005-9 g, 0.001-8 g, 0.005-7 g, 0.01-6 g, 0.05-5 g, 0.1-4 g, 0.5-4 g, or 1-3 g in the composition.

In some embodiments, a molar ratio of the therapeutic agent to the phosphorylated polyphenol e.g. phosphorylated pyrone analog such as a phosphorylated flavonoid, such as a phosphorylated quercetin, phosphorylated fisetin, or phosphorylated 5,7-dideoxyquercetin can be 0.0001:1 to 1:1. Without limiting the scope of the invention, the molar ratio of one or more of the therapeutic agents to the phosphorylated polyphenol e.g. phosphorylated pyrone analog such as a phosphorylated flavonoid, such as a phosphorylated quercetin, phosphorylated fisetin, or phosphorylated 5,7-dideoxyquercetin can be about 0.0001:1 to about 10:1, or about 0.001:1 to about 5:1, or about 0.01:1 to about 5:1, or about 0.1:1 to about 2:1, or about 0.2:1 to about 2:1, or about 0.5:1 to about 2:1, or about 0.1:1 to about 1:1. Without limiting the scope of the present invention, the molar ratio of one or more of the therapeutic agents to the phosphorylated pyrone analog such as a phosphorylated flavonoid, such as a phosphorylated quercetin, phosphorylated fisetin, or phosphorylated 5,7-dideoxyquercetin can be about $0.03 \times 10^{-5}:1$, $0.04 \times 10^{-5}:1$, $0.1 \times 10^{-5}:1$, $0.2 \times 10^{-5}:1$, $0.3 \times 10^{-5}:1$, $0.4 \times 10^{-5}:1$, $0.5 \times 10^{-5}:1$, $0.8 \times 10^{-5}:1$, $0.1 \times 10^{-4}:1$, $0.2 \times 10^{-4}:1$, $0.3 \times 10^{-4}:1$, $0.4 \times 10^{-4}:1$, $0.5 \times 10^{4}:1$, $0.8 \times 10^{-4}:1$, $0.1 \times 10^{-3}:1$, $0.2 \times 10^{-3}:1$, $0.3 \times 10^{-3}:1$, $0.4 \times 10^{-3}:1$, $0.5 \times 10^{-3}:1$, $0.8 \times 10^{-3}:1$, $0.1 \times 10^{-2}:1$, $0.2 \times 10^{-2}:1$, $0.3 \times 10^{-2}:1$, $0.4 \times 10^{-2}:1$, $0.5 \times 10^{-2}:1$, $0.6 \times 10^{-2}:1$, $0.8 \times 10^{-2}:1$, 0.01:1, 0.1:1; 0.2:1, 0.3:1, 0.4:1, 0.5:1, 0.6:1, 0.7:1, 0.8:1, 0.9:1, 1:1, 2:1, 3:1, 4:1, or 5:1.

In some embodiments, the therapeutic agent is tacrolimus, sirolimus, mycophenolate, methadone, cyclosporin, prednisone, or voclosporin A. Pharmaceutical Compositions The phosphorylated polyphenols of the invention are usually administered in the form of pharmaceutical compositions. The drugs described above are also administered in the form of pharmaceutical compositions. When the transport protein modulators and the drugs are used in combination, both components may be mixed into a preparation or both components may be formulated into separate preparations to use them in combination separately or at the same time.

This invention therefore provides pharmaceutical compositions that contain, as the active ingredient, a phosphorylated polyphenol e.g. phosphorylated pyrone analog such as a phosphorylated flavonoid, such as a phosphorylated quercetin, phosphorylated fisetin, or phosphorylated 5,7-dideoxyquercetin or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

This invention further provides pharmaceutical compositions that contain, as the active ingredient, a phosphorylated polyphenol e.g. phosphorylated pyrone analog such as a phosphorylated flavonoid, such as a phosphorylated quercetin, phosphorylated fisetin, or phosphorylated 5,7-dideoxyquercetin which acts as a side effect modulator, e.g. BTB transport protein modulator or a pharmaceutically acceptable salt and/or coordination complex thereof, a therapeutic agent or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

Such compositions are prepared in a manner well known in the pharmaceutical art.

Pharmaceutical compositions for oral administration In some embodiments, the invention provides a pharmaceutical composition for oral administration containing a combination of a therapeutic agent and a phosphorylated polyphenol e.g. phosphorylated pyrone analog such as a phosphorylated flavonoid, such as a phosphorylated quercetin, phosphorylated fisetin, or phosphorylated 5,7-dideoxyquercetin and a pharmaceutical excipient suitable for oral administration. In some embodiment, the phosphorylated polyphenol reduces or eliminates a side effect of the therapeutic agent. In some embodiments, the phosphorylated polyphenol reduces or eliminates the side effect of the therapeutic agent is a BTB transport protein modulator, as described elsewhere herein.

In some embodiments, the invention provides a solid pharmaceutical composition for oral administration containing:

(i) an effective amount of a therapeutic agent;

(ii) an effective amount of a phosphorylated polyphenol capable of reducing or eliminating one or more side effects of the therapeutic agent; and (iii) a pharmaceutical excipient suitable for oral administration.

In some embodiments, the composition further contains:

(iv) an effective amount of a second therapeutic agent.

In some embodiments, the pharmaceutical composition may be a solid pharmaceutical composition suitable for oral consumption.

In some embodiments, the therapeutic agent is an immunosuppressive agent. In some embodiments, the therapeutic agent is a calcineurin inhibitor. In some embodiments, the therapeutic agent tacrolimus or sirolimus. In some embodiments, the phosphorylated polyphenol is capable of reducing or eliminating one or more side effects of the therapeutic agent is a BTB transport protein modulator, e.g., a BTB transport protein activator.

In some embodiments, the invention provides a solid pharmaceutical composition for oral administration containing:

(i) an effective amount of a therapeutic agent that is tacrolimus, sirolimus, mycophenolate, methadone, cyclosporin, prednisone, voclosporin, oxycodone, gabapentin, pregabalin, hydrocodone, fentanyl, hydromorphone, levorphenol, morphine, methadone, mycophenolate, tramadol, hydromorphine, topiramate, diacetyl morphine, codeine, olanzapine, hydrocortisone, prednisone, sufentanyl, alfentanyl, carbamazepine, lamotrigine, doxepin, or haloperidol;

(ii) an effective amount of a phosphorylated polyphenol that is phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin; and (iii) a pharmaceutical excipient suitable for oral administration.

In some embodiments, the composition further contains (iv) an effective amount of a second therapeutic agent. Exemplary second therapeutic agents include aspirin, acetaminophen, and ibuprofen.

In some embodiments, the invention provides a solid pharmaceutical composition for oral administration containing:

(i) an effective amount of a therapeutic agent that is tacrolimus, sirolimus, mycophenolate, methadone, cyclosporin, prednisone, or voclosporin;

(ii) an effective amount of a phosphorylated polyphenol that is phosphorylated quercetin, phosphorylated fisetin, phosphorylated 5,7-dideoxyquercetin, phosphorylated galangin, or phosphorylated kaempferol; and (iii) a pharmaceutical excipient suitable for oral administration.

In some embodiments, the composition further contains (iv) an effective amount of a second therapeutic agent. Exemplary second therapeutic agents include aspirin, acetaminophen, and ibuprofen.

In some embodiments, the pharmaceutical composition may be a liquid pharmaceutical composition suitable for oral consumption.

In some embodiments, the invention provides a solid pharmaceutical composition for oral administration containing an effective amount of sirolimus, an amount of phosphorylated quercetin, phosphorylated fisetin, or phosphorylated 5,7-dideoxyquercetin that is effective in reducing or eliminating a side effect of sirolimus, and a pharmaceutically acceptable excipient. In some embodiments, the composition further includes an effective amount of acetaminophen. In some embodiments, the invention provides a liquid pharmaceutical composition for oral administration containing an effective amount of sirolimus, an amount of phosphorylated quercetin, phosphorylated fisetin, or phosphorylated 5,7-dideoxyquercetin that is effective in reducing or eliminating a side effect of sirolimus, and a pharmaceutically acceptable excipient. In some embodiments, the composition further includes an effective amount of acetaminophen.

In some embodiments, the invention provides a solid pharmaceutical composition for oral administration containing sirolimus at about 1-160 mg, phosphorylated quercetin, phosphorylated fisetin, or phosphorylated 5,7-dideoxyquercetin at about 10-1000 mg and a pharmaceutically acceptable excipient. In some embodiments, the invention provides a liquid pharmaceutical composition for oral administration containing sirolimus at about 1-200 mg/ml, phosphorylated quercetin, phosphorylated fisetin, or phosphorylated 5,7-dideoxyquercetin at about 10-1000 mg/ml and a pharmaceutically acceptable excipient. In some embodiments, the composition further includes acetaminophen at about 10-750 mg/ml.

In some embodiments, the invention provides a solid pharmaceutical composition for oral administration containing an effective amount of tacrolimus, an amount of phosphorylated quercetin, phosphorylated fisetin, or phosphorylated 5,7-dideoxyquercetin that is effective in reducing or eliminating a side effect of tacrolimus, and a pharmaceutically acceptable excipient. In some embodiments, the invention provides a liquid pharmaceutical composition for oral administration containing an effective amount of tacrolimus, an amount of phosphorylated quercetin, phosphorylated fisetin, or phosphorylated 5,7-dideoxyquercetin that is effective in reducing or eliminating a side effect of tacrolimus, and a pharmaceutically acceptable excipient.

In some embodiments, the invention provides a solid pharmaceutical composition for oral administration containing tacrolimus at about 1-160 mg, phosphorylated quercetin, phosphorylated fisetin, or phosphorylated 5,7-dideoxyquercetin at about 10-1000 mg and a pharmaceutically acceptable excipient. In some embodiments, the composition further includes acetaminophen at about 200-750 mg. In some embodiments, the invention provides a liquid pharmaceutical composition for oral administration containing tacrolimus at about 1-200 mg/ml, phosphorylated quercetin, phosphorylated fisetin, or phosphorylated 5,7-dideoxyquercetin at about 10-1000 mg/ml and a pharmaceutically acceptable excipient.

In some embodiments, the invention provides a solid pharmaceutical composition for oral administration containing an effective amount of cyclosporin, an amount of phosphorylated quercetin, phosphorylated fisetin, or phosphorylated 5,7-dideoxyquercetin that is effective in reducing or eliminating a side effect of cyclosporin, and a pharmaceutically acceptable excipient. In some embodiments, the invention provides a liquid pharmaceutical composition for oral administration containing an effective amount of cyclosporin, an amount of phosphorylated quercetin, phosphorylated fisetin, or phosphorylated 5,7-dideoxyquercetin that is effective in reducing or eliminating a side effect of cyclosporin, and a pharmaceutically acceptable excipient.

In some embodiments, the invention provides a solid pharmaceutical composition for oral administration containing cyclosporin at about 100-800 mg, phosphorylated quercetin, phosphorylated fisetin, or phosphorylated 5,7-dideoxyquercetin at about 10-1000 mg and a pharmaceutically acceptable excipient. In some embodiments, the invention provides a liquid pharmaceutical composition for oral administration containing cyclosporin at about 5-500 mg/ml, phosphorylated quercetin, phosphorylated fisetin, or phosphorylated 5,7-dideoxyquercetin at about 10-1000 mg/ml and a pharmaceutically acceptable excipient.

Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the therapeutic agent and/or phosphorylated phenol e.g. phosphorylated pyrone analog such as a phosphorylated flavonoid, such as a phosphorylated quercetin, phosphorylated fisetin, or phosphorylated 5,7-dideoxyquercetin and to minimize precipitation of the therapeutic agent and/or phosphorylated phenol e.g. phosphorylated pyrone analog such as a phosphorylated flavonoid, such as a phosphorylated quercetin, phosphorylated fisetin, or phosphorylated 5,7-dideoxyquercetin. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methyl pyrrolidones, monooctanoin, diethylene glycol monoethyl ether, and water.

In some embodiments, the oral formulation is made from the aqueous composition of sulfoalkyl ether cyclodextrin-flavonoid such as Captisol™ and a phosphorylated polyphenol, for example phosphorylated pyrone analog such as a phosphorylated flavonoid, e.g. phosphorylated quercetin. The oral formulation can be an aqueous liquid for oral administration, or may be a solid formulation that is produced by drying the aqueous composition, for example by freeze-drying or lyophilization. Lyophilization is a freeze-drying process in which water is sublimed from the composition after it is frozen. The particular advantages of the lyophilization process are that biologicals and pharmaceuticals that are relatively unstable in aqueous solution can be dried without elevated temperatures (thereby eliminating the adverse thermal affects) and then stored in the dry state where there are few stability problems. Once the aqueous composition is dried, it can be handled, for example, as a dried powder. The dried powder can be further formulated into oral pharmaceutical compositions as described herein.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, is ascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for infection. In some embodiments, the invention provides a pharmaceutical composition for injection containing a combination of a therapeutic agent and a phosphorylated phenol e.g. phosphorylated pyrone analog such as a phosphorylated flavonoid, such as a phosphorylated quercetin, phosphorylated fisetin, or phosphorylated 5,7-dideoxyquercetin, and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

In some embodiments, the injectable formulation is made from the aqueous composition of sulfoalkyl ether cyclodextrin-flavonoid such as Captisol™ and a phosphorylated polyphenol, for example phosphorylated pyrone analog such as a phosphorylated flavonoid, e.g. phosphorylated quercetin. Where the pharmaceutical composition for injection is made from the aqueous composition of sulfoalkyl ether cyclodextrin-flavonoid, pharmaceutical composition for injection can be made either as a liquid formulation or, may be dissolved into solution, and processed to form a solid formulation produced by removal of liquid from the liquid composition, for example by freeze drying or lyophilization. Having a dried, solid formulation can be advantageous for increasing the shelf-life. The solid formulation can then be re-dissolved into solution for injection The dried powder can be further formulated into pharmaceutical composition for injection as described herein.

Sterile injectable solutions are prepared by incorporating phosphorylated polyphenol and/or the therapeutic agent in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a combination of a therapeutic agent and phosphorylated phenol e.g. phosphorylated pyrone analog such as a phosphorylated flavonoid, such as a phosphorylated quercetin, phosphorylated fisetin, or phosphorylated 5,7-dideoxyquercetin, and a pharmaceutical excipient suitable for transdermal delivery. In some embodiments, the phosphorylated phenol e.g. phosphorylated pyrone analog such as a phosphorylated flavonoid, such as a phosphorylated quercetin, phosphorylated fisetin, or phosphorylated 5,7-dideoxyquercetin is capable of reducing or eliminating the side effect of the therapeutic agent. In some embodiments, the phosphorylated phenol e.g. phosphorylated pyrone analog such as a phosphorylated flavonoid, such as a phosphorylated quercetin, phosphorylated fisetin, or phosphorylated 5,7-dideoxyquercetin is a BTB transport protein modulator. Components and amounts of agents in the compositions are as described herein.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another preferred formulation for use in the methods of the present invention employs transdermal delivery devices ("patches"). Such transdermal patches may be used to provide continuous or discontinuous infusion of the transport protein modulator in controlled amounts, either with or without therapeutic agent. Thus, in some embodiments the invention provides a transdermal patch incorporating a phosphorylated phenol e.g. phosphorylated pyrone analog such as a phosphorylated flavonoid, such as phosphorylated quercetin, phosphorylated fisetin, or phosphorylated 5,7-dideoxyquercetin. In some embodiments the invention provides a transdermal patch incorporating a phosphorylated phenol e.g. phosphorylated pyrone analog such as a phosphorylated flavonoid, such as a phosphorylated quercetin, phosphorylated fisetin, or phosphorylated 5,7-dideoxyquercetin in combination with a therapeutic agent, e.g. an immunosuppressant such as a calcineurin inhibitor.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

B. Kits

The invention also provides kits. The kits include a phosphorylated phenol e.g. phosphorylated pyrone analog such as a phosphorylated flavonoid, such as a phosphorylated quercetin, phosphorylated fisetin, or phosphorylated 5,7-dideoxyquercetin, in suitable packaging. Other components that may be included are written material that can include instructions for use, discussion of clinical studies, listing of side effects, and the like. The kit may further contain a therapeutic agent that has a side effect. In some embodiments, the phosphorylated phenol e.g. phosphorylated pyrone analog such as a phosphorylated flavonoid, such as a phosphorylated quercetin, phosphorylated fisetin, or phosphorylated 5,7-dideoxyquercetin is provided as separate compositions in separate containers within the kit. In some embodiments, the therapeutic agent and the phosphorylated phenol e.g. phosphorylated pyrone analog such as a phosphorylated flavonoid, such as a phosphorylated quercetin, phosphorylated fisetin, or phosphorylated 5,7-dideoxyquercetin are provided as a single composition within a container in the kit. Suitable packaging and additional articles for use (e.g., measuring cup for liquid preparations, foil wrapping to minimize exposure to air, and the like) are known in the art and may be included in the kit.

VI. METHODS

In another aspect, the invention provides methods, including methods of treatment, methods of decreasing the concentration of a substance in a physiological compartment (e.g., methods of delaying the onset or preventing chronic neurodegenerative diseases), methods of enhancing a therapeutic effect of a substance, methods of delaying, preventing, reducing or eliminating tolerance or dependence in an animal that is administered a substance, methods of drug wash-out, and methods for identifying modulators of blood-brain barrier transport proteins.

For simplicity, some methods will be described in terms of reduction of a side effect of a substance. It is understood that the methods apply equally to exclusion of a substance from the fetal compartment, or reduction of fetal effects of a substance.

The term "animal" or "animal subject" as used herein includes humans as well as other mammals. The methods generally involve the administration of one or more drugs for the treatment of one or more diseases. Combinations of agents can be used to treat one disease or multiple diseases or to modulate the side-effects of one or more agents in the combination.

The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A. Methods of Treating Conditions

In some embodiments, the invention provides a method of treating a condition by administering to an animal in need of treatment an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin sufficient to reduce or eliminate a side effect of the therapeutic agent. In some embodiments, the activator reduces or eliminates a plurality of side effects of the therapeutic agent. In some embodiments the animal is a mammal, e.g., a human.

The therapeutic agent and the phosphorylated phenol e.g. phosphorylated pyrone analog such as a phosphorylated flavonoid, such as a phosphorylated quercetin, phosphorylated fisetin, or phosphorylated 5,7-dideoxyquercetin are co-administered. "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present. Thus, in some embodiments, the phosphorylated phenol e.g. phosphorylated pyrone analog such as a phosphorylated flavonoid, such as a phosphorylated quercetin, phosphorylated fisetin, or phosphorylated 5,7-dideoxyquercetin are administered in a single composition. In some embodiments, the therapeutic agent and the phosphorylated phenol e.g. phosphorylated pyrone analog such as a phosphorylated flavonoid, such as a phosphorylated quercetin, phosphorylated fisetin, or phosphorylated 5,7-dideoxyquercetin are admixed in the composition. Typically, the therapeutic agent is present in the composition in an amount sufficient to produce a therapeutic effect, and the phosphorylated phenol e.g. phosphorylated pyrone analog such as a phosphorylated flavonoid, such as a phosphorylated quercetin, phosphorylated fisetin, or phosphorylated 5,7-dideoxyquercetin is present in the composition in an amount sufficient to reduce a side effect of the therapeutic agent. In some embodiments, the therapeutic agent is present in an amount sufficient to exert a therapeutic effect and the phosphorylated phenol e.g. phosphorylated pyrone analog such as a phosphorylated flavonoid, such as a phosphorylated quercetin, phosphorylated fisetin, or phosphorylated 5,7-dideoxyquercetin is present in an amount sufficient to decrease a side effect of the therapeutic agent by an average of at least about 5, 10, 15, 20, 25, 30, 40, 50, 60, 70, 80, 90, more than 90%, or substantially eliminate a side effect compared to the effect without the phosphorylated phenol e.g. phosphorylated pyrone analog such as a phosphorylated flavonoid, such as a phosphorylated quercetin, phosphorylated fisetin, or phosphorylated 5,7-dideoxyquercetin.

In some embodiments the methods of the invention are used to reduce the side effect and/or increase the effectiveness of an immunosuppressant. The immunosuppressant can be a cyclosporin (Neoral, Sandimmune, SangCya), an azathioprine (Imuran), a corticosteroid such as prednisolone (Deltasone, Orasone), basiliximab (Simulect), daclizumab (Zenapax), muromonab CD3 (Orthoclone OKT3), tacrolimus (Prograf®), ascomycin, pimecrolimus (Elidel), azathioprine (Imuran), cyclosporin (Sandimmune, Neoral), glatiramer acetate (Copaxone), mycophenolate (CellCept), sirolimus (Rapamune), voclosporin In some embodiments methods of the invention are used to reduce the side effect and/or increase the effectiveness of a calcineurin inhibitor such as tacrolimus (Prograf®), The methods of the invention can be used to reduce the side effect and/or increase the effectiveness of a selective estrogen receptor modulator (SERM), such as tamoxifen.

The methods of the invention can be used to reduce the side effect and/or increase the effectiveness of an antilipedimic agent such as an HMG-CoA inhibitor such as lovastatin, simvastatin, pravastatin, fluvastatin, or atorvastatin The methods of the invention can be used to reduce the side effect and/or increase the effectiveness of an antihyperglycemic agent (antiglycemics, hypoglycemic agents) such as glyburide, glipizide, gliclazide, or glimepride; a meglitinide such as repaglinide or netaglinide, a biguanide such as metformin, a thiazolidinedione, an α-glucosidase inhibitor such as acarbose or miglitol, glucagon, somatostatin, or diazoxide.

The methods of the invention can be used to reduce the side effect and/or increase the effectiveness of a cannabinoid.

The methods of the invention can be used to reduce the side effect and/or increase the effectiveness of an antidepressant. In some embodiments, antidepressants cause the side effects of high blood sugar and diabetes. The methods of the invention can be used, for example to reduce these side effects. In some embodiments the therapeutic agent is an antidepressant selected from the group of aripiprazone (Abilify), nefazodone (Serzone), escitalopram oxalate (Lexapro), sertraline (Zoloft), escitalopram (Lexapro), fluoxetine (Prozac), bupropion (Wellbutrin, Zyban), paroxetine (Paxil), venlafaxine (Effexor), trazodone (Desyrel), amitriptyline (Elavil), citalopram (Celexa), duloxetine (Cymbalta), mirtazapine (Remeron), nortriptyline (Pamelor), imipramine (Tofranil), amitriptyline (Elavil), clomipramine (Anafranil), doxepin (Adapin), trimipramine (Surmontil), amoxapine (Asenidin), desipramine (Norpramin), maprotiline (Ludiomil), protryptiline (Vivactil), citalopram (Celexa), fluvoxamine (Luvox), phenelzine (Nardil), trancylpromine (Parnate), selegiline (Eldepryl).

The methods of the invention can be used to reduce the side effect and/or increase the effectiveness of an antineuropathic agent such as gabapentin.

The methods of the invention can be used to reduce the side effect and/or increase the effectiveness of an anticonvulsant. In some cases, it can be an anticonvulsant that also has efficacy in the treatment of pain. The therapeutic agent can be, for example, acetazolamide (Diamox), carbamazepine (Tegretol), clobazam (Frisium), clonazepam (Klonopin/Rivotril), clorazepate (Tranxene-SD), diazepam (Valium), divalproex sodium (Depakote), ethosuximide (Zarontin), ethotoin (Peganone), felbamate (Felbatol), fosphenyloin (Cerebyx), gabapentin (Neurontin), lamotrigine (Lamictal), levetiracetam (Keppra), lorezepam (Ativan), mephenyloin (Mesantoin), metharbital (Gemonil), methsuximide (Celontin). Methazolamide (Neptazane), oxcarbazepine (Trileptal), phenobarbital, phenyloin (Dilantin/Epanutin), phensuximide (Milontin), pregabalin (Lyrica), primidone (Mysoline), sodium valproate (Epilim), stiripentol (Diacomit), tiagabine (Gabitril), topiramate (Topamax), trimethadione (Tridione), valproic acid (Depakene/Convulex), vigabatrin (Sabril), zonisamide (Zonegran), or cefepime hydrochloride (Maxipime).

In some cases, the phosphorylated phenols of the invention are administered to diminish or eliminate a side effect of a therapeutic agent. In some cases where the phosphorylated phenol is administered to eliminate a side effect of a therapeutic agent it is the metabolite of the phosphorylated phenol that is partly or fully responsible for the elimination of the side effect. Where the metabolite of the phosphorylated polyphenol is responsible for the effect, the phosphorylated polyphenol can be acting as a prodrug.

A prodrug is a precursor which will undergo metabolic activation in vivo to the active drug. The phosphorylated compounds of the present invention can act as prodrugs, for example, where the phosphate moiety is cleaved in vivo to yield an active compound. Non-specific phosphatases such as alkaline phosphatases in mammals are capable of dephosphorylating phosphate prodrugs into the biologically active forms. The phosphorylation can aid in the administration of drug of low water solubility to warm blooded animals for therapeutic purposes under conditions of more effective absorption and bioavailability by formulation into a water soluble biolabile form (See, for example, Krogsgaard-Larsen, P. and Bundegaard, H., eds., A textbook of Drug Design and Drug Development, Harvard Academic Publishers, p. 148, 1991). In some cases, more specific phosphatases, and phosphatases localized in particular areas of an animal, such as in vascular endothelial cells can be utilized to control the timing and location of de-phosphorylation and release of the drug from the prodrug form (see, for example, U.S. Patent Application 20060100179.

In some embodiments, the phosphorylated polyphenol will have higher water solubility than the non-phosphorylated polyphenol. In some embodiments the phosphorylated polyphenol will have multiple phosphates and will have higher water solubility than the polyphenol with fewer phosphate groups. For example, quercetin aglycone has relatively low solubility in water, and relatively low solubility in the blood. The addition of a phosphate to quercetin will tend to improve the solubility of the quercetin in water and in the blood and thus increase its bioavailability. The addition of the phosphate group can increase water solubility by adding polarity, by adding an ionic substituent, and in some cases due to geometrical (molecular shape) factors. In some embodiments of the invention, the phosphorylated polyphenol is at least about 10%, 20%, 25%, 30%, 40%, 50%, 60%, 75%, 90%, or 100% or at least about 2, 3, 4 5, 10, 20, 50, 100, 1,000, or 10,000 times more water soluble than the corresponding non-phosphorylated polyphenol. In some embodiments of the invention, the phosphorylated polyphenol is at least about 10%, 20%, 25%, 30%, 40%, 50%, 60%, 75%, 90%, or 100% or at least about 2, 3, 4 5, 10, 20, 50, 100, 1,000, or 10,000 times more soluble in a bodily fluid than the corresponding non-phosphorylated polyphenol. Methods for determining solubility are well known in the art. Where the fluid is clear, optical methods may be used for determining solubility. It is also possible to determine solubility by a direct measurement of the dissolved component, for example by HPLC. The solubility may be dependent on pH. In some embodiments the pH of the solution is neutral pH. In some embodiments the pH is between 6.8 and 7.2, in some embodiments the pH is between 6.5 and 7.5, in some embodiments the pH is between 6.0 and 7.0, in some embodiments the pH is between 5 and 9, in some embodiments the pH is between 4 and 10, in some embodiments the pH is between 3 and 11, in some embodiments the pH is between 2 and 12. The biological fluids of the present invention can be any fluid in an animal. Non-limiting examples of biological fluids are: blood, lymph, saliva, mucus, gastric juice, urine, aqueous humor, and semen.

One embodiment of the invention is a method for the treatment of an animal by oral administration of a therapeutic agent and a phosphorylated polyphenol, e.g. phosphorylated pyrone analog such as a phosphorylated flavonoid, such as a phosphorylated quercetin, phosphorylated fisetin, or phosphorylated 5,7-dideoxyquercetin that is greater than about 10%, 20%, 25%, 30%, 40%, 50%, 60%, 75%, 90%, or 100% or about 2, 3, 4 5, 10, 20, 50, 100, 1,000, or 10,000 times more soluble in water than the corresponding non-phosphorylated polyphenol. One embodiment of the invention is a method for the treatment of an animal by oral administration of a therapeutic agent and a phosphorylated polyphenol, e.g. phosphorylated pyrone analog such as a phosphorylated flavonoid, such as a phosphorylated quercetin, phosphorylated fisetin, or phosphorylated 5,7-dideoxyquercetin that is greater than about 10%, 20%, 25%, 30%, 40%, 50%, 60%, 75%, 90%, or 100% or greater than about 2, 3, 4 5, 10, 20, 50, 100, 1,000, or 10,000 times more soluble in a bodily fluid than the corresponding non-phosphorylated polyphenol. In some embodiments the therapeutic agent is an immunosuppressive agent, e.g. a calcineurin inhibitor such as tacrolimus or sirolimus.

In some embodiments, the increased water solubility will result in increased solubility of the polyphenol in a bodily fluid. In some embodiments, the increased solubility in a bodily fluid will result in greater bioavailability of the phosphorylated polyphenol than for the corresponding non-phosphorylated polyphenol.

In some embodiments, the phosphorylated polyphenol will provide a longer half-life of drug effect than for a non-phosphorylated polyphenol. For example, and without being limited by mechanism, where a phosphorylated phenol is not an active BTB transport protein modulator, and its de-phosphorylated form is active as a BTB transport protein modulator, the amount of active form can depend on the rate of de-phosphorylation. If the rate of de-phosphorylation is relatively slow, the de-phosphorylation process can act to delay the delivery of the active form. Under these conditions, the phosphorylated form acts as a kind of reservoir for the active form of the drug, thus extending the half life of drug effect. It will be understood by those of skill in the art that the relative rates of de-phosphorylation and the relative rates of absorption, clearance, and volume of distribution of the phosphorylated and de-phosphorylated forms can influence the half life of drug effect for the drug. In some embodiments, the de-phosphorylation of the phosphorylated form can be used as a tool to control the timing and the area to which the active compound is delivered, allowing the control of the target concentration and of the maintenance dose.

In some embodiments, the phosphorylated form is also an active form, i.e., dephosphorylation is not necessary in order to achieve the desired modulation of side effects of a therapeutic agent. The phosphorylated form may be more active, equally active, or less active than the dephosphorylated form, and the effects of the phosphorylated form may be due to a combination of its own effect and the effect and timing of appearance of the dephosphorylated from. However, it will be understood that the modulation of one or more side effects and/or therapeutic effects of a therapeutic agent by the phosphorylated pyrone analogs, as described herein, is not limited by the mechanism by which it is achieved.

In some embodiments, the therapeutic agent and the phosphorylated polyphenol are administered, at least in part, as an ionic complex between an opiate or an immunomodulator and a phosphorylated polyphenol. In some cases, the administration of the ionic complex results in higher solubility and greater bioavailability than where the compounds are administered without comprising an ionic complex.

Administration of the therapeutic agent and the phosphorylated phenol e.g. phosphorylated pyrone analog such as a phosphorylated flavonoid, such as a phosphorylated quercetin, phosphorylated fisetin, or phosphorylated 5,7-dideoxyquercetin may be any suitable means. If the agents are administered as separate compositions, they may be administered by the same route or by different routes. If the agents are administered in a single composition, they may be administered by any suitable route. In some embodiments, the agents are administered as a single composition by oral administration. In some embodiments, the agents are administered as a single composition by transdermal administration. In some embodiments, the agents are administered as a single composition by injection.

In some embodiments, the phosphorylated phenol e.g. phosphorylated pyrone analog such as a phosphorylated flavonoid, such as a phosphorylated quercetin, phosphorylated fisetin, or phosphorylated 5,7-dideoxyquercetin is a side effect modulator, e.g. BTB transport protein modulator. BTB transport protein modulators are as described herein. In some embodiments, a phosphorylated polyphenol is used. In some embodiments, a phosphorylated pyrone analog such as a phosphorylated flavonoid is used. In some embodiments, the phosphorylated pyrone analog such as a phosphorylated flavonoid is phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin. In some embodiments, the phosphorylated pyrone analog such as a phosphorylated flavonoid is phosphorylated quercetin, phosphorylated fisetin, phosphorylated 5,7-dideoxyquercetin, phosphorylated kaempferol, or phosphorylated galangin. In some embodiments, the phosphorylated pyrone analog such as a phosphorylated flavonoid is phosphorylated quercetin. In some embodiments, the phosphorylated pyrone analog such as a phosphorylated flavonoid is phosphorylated fisetin. In some embodiments, the phosphorylated pyrone analog such as a phosphorylated flavonoid is phosphorylated 5,7-dideoxyquercetin. In some embodiments, the phosphorylated pyrone analog such as a phosphorylated flavonoid is quercetin-3'-O-phosphate. Dosages are as provided for compositions. Typically, the daily dosage of the side effect modulator, e.g. BTB transport protein modulator will be about 0.5-100 mg/kg.

The therapeutic agent may be any therapeutic agent described herein. In some embodiments, the therapeutic agent is an immunosuppressant, antineoplastic, amphetamine, antihypertensive, vasodilator, barbiturate, membrane stabilizer, cardiac stabilizer, glucocorticoid, chemotherapeutic agent, or antiinfective, immunomodulator, tolerogen, immunostimulants, drug acting on the blood and the blood-forming organs, hematopoietic agent, growth factor, mineral, and vitamin, anticoagulant, thrombolytic, antiplatelet drug, hormone, hormone antagonist, pituitary hormone, thyroid and antithyroid drug, estrogen and progestin, androgen, adrenocorticotropic hormone; adrenocortical steroid and synthetic analogs, insulin, oral hypoglycemic agents, calcium, phosphate, parathyroid hormone, vitamin D, calcitonin, and other compounds.

The methods of the invention may be used for treatment of any suitable condition, e.g., diseases of the heart, circulation, lipoprotein metabolism, hemostasis and thrombosis, respiratory system, kidney, gastrointestinal tract, endocrine system, reproductive system, or hemopoietic system, where one or more therapeutic agents are used that have side effect. For example, in some embodiments, the methods of the invention include the treatment of hypertension in an animal by administering to an animal in need of treatment an effective amount of an antihypertensive and an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect of the hypertensive. Another exemplary embodiment is the treatment or prevention of infection in an animal by administering to an animal in need of treatment or prevention of infection an effective amount of an antiinfective agent and an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect of the antiinfective agent.

Another exemplary embodiment is the treatment or prevention of cancer in an animal by administering to an animal in need of treatment or prevention of cancer an effective amount of an chemotherapeutic agent such as tamoxifen and an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect of the chemotherapeutic agent.

Another exemplary embodiment is the treatment of graft rejection in an animal by administering to an animal in need of prevention or treatment an effective amount of an immunosuppressive agent, e.g., an calcineurin inhibitor such as sirolimus or tacrolimus, and an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect or endocrine effect of the immunosuppressive agent.

Another exemplary embodiment is the prevention of organ rejection in an animal by administering to an animal that has received or will receive an organ transplant an effective amount of a calcineurin inhibitor such as tacrolimus or a tacrolimus analog and an effective amount of a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect, e.g., a hyperglycemic effect or a side effect of the calcineurin inhibitor.

When a therapeutic agent and a phosphorylated phenol e.g. phosphorylated pyrone analog such as a phosphorylated flavonoid, such as a phosphorylated quercetin, phosphorylated fisetin, or phosphorylated 5,7-dideoxyquercetin that reduces or eliminates a side effect of the therapeutic agent are used in combination, any suitable ratio of the two agents, e.g., molar ratio, wt/wt ration, wt/volume ratio, or volume/volume ratio, as described herein, may be used.

In some embodiments of the methods of the invention, the invention provides a method of treating a condition by administering to an animal suffering from the condition an effective amount of tacrolimus and an amount of a BTB transport protein modulator sufficient to change the concentration of tacrolimus in a physiological compartment. In some embodiments of the methods of the invention the physiological compartment is selected from the group consisting of blood, lymph nodes, spleen, peyer's patches, lungs, heart kidney, pancreas liver, and gull bladder. In some embodiments of the methods of the invention the BTB transport modulator decrease the clearance of tacrolimus from a compartment where the drug is exerting therapeutic effect.

B. Methods of Modulating the Concentration of a Substance in a Physiological Compartment The invention provides methods for reducing the concentration of a substance in a physiological compartment by selectively increasing efflux of the substance from the physiological compartment to an external environment. The physiological compartment preferably is a central nervous system or a fetal compartment.

In some embodiments, compositions of the invention may be administered chronically to an individual in order to prevent, delay the appearance, or slow or halt the progression of a chronic neurodegenerative condition. In some embodiments, compositions of the invention may be administered chronically to an individual in order to remove from the CNS one or more substances associated with a chronic neurodegenerative condition. In some embodiments, the neurodegenerative condition is prion disease, Alzheimer's disease (AD), Parkinson's disease (PD), Huntington's disease (HD), ALS, multiple sclerosis, transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, or retinal degeneration. In some embodiments, the neurodegenerative disease is AD. In some embodiments, the substance associated with a neurodegenerative disease is amyloid beta. In some embodiments, a phosphorylated pyrone analog such as a phosphorylated flavonoid is administered to the individual, such as phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin. In some embodiments, the individual is a human and is chronically administered an amount of phosphorylated quercetin, phosphorylated fisetin, or phosphorylated 5,7-dideoxyquercetin effective in removing amyloid beta from the CNS. In some embodiments, the phosphorylated quercetin, phosphorylated fisetin, or phosphorylated 5,7-dideoxyquercetin is administered in a pharmaceutical composition with a pharmaceutically acceptable excipient at a dose of 100 mg-10,000 mg per day. Other dosages of phosphorylated quercetin, phosphorylated fisetin, or phosphorylated 5,7-dideoxyquercetin, as described herein, may also be used.

In some embodiments, the invention provides a method of increasing the concentration of a therapeutic agent in a non- CNS compartment by the administration of a phosphorylated polyphenols, e.g. phosphorylated pyrone analog such as a phosphorylated flavonoid such as phosphorylated quercetin, phosphorylated fisetin, or phosphorylated 5,7-dideoxyquercetin. While not being bound by theory, a BTB transport protein activator can result in the exclusion of a compound or removal of compound from the CNS compartment. Because the compartments of the body are interconnected, where the compound, such as a therapeutic agent, is excluded from the CNS compartment, there can be more of the compound available to the periphery than where the compound is distributed into the periphery as well. In some embodiments, the concentration of therapeutic agent in a non-CNS compartment is at least about 1, 5, 10, 15, 20, 25, 30, 35, 40, 45, 50, 55, 60, 65, 70, 75, 80, 85, 90, 95, or more than 95% higher than without the administration of a phosphorylated polyphenol, e.g. phosphorylated pyrone analog such as a phosphorylated flavonoid such as phosphorylated quercetin, phosphorylated fisetin, or phosphorylated 5,7-dideoxyquercetin.

In some embodiments of the methods of the invention, the invention provides a method of treating a condition by administering to an animal suffering from the condition an effective amount of tacrolimus and an amount of a BTB transport protein modulator sufficient to change the concentration of tacrolimus in a physiological compartment. In some embodiments of the methods of the invention the physiological compartment is selected from the group consisting of blood, lymph nodes, spleen, peyer's patches, lungs, heart kidney, pancreas liver, and gull bladder. In some embodiments of the methods of the invention the BTB transport modulator decrease the clearance of tacrolimus from a compartment where the drug is exerting therapeutic effect.

C. Methods of Treating Pain

The invention provides methods of treating pain such as acute or chronic pain, using therapeutic agents and the phosphorylated compositions of the invention. Any suitable type of pain, whether acute or chronic, may be treated by the methods of the invention. Thus, in some embodiments, the invention provides a method of treating an animal for pain by administering to an animal in pain an effective amount of an opioid analgesic agent, e.g. an opioid receptor agonist such as oxycodone or morphine and an amount of a polyphenol e.g. phosphorylated pyrone analog such as a phosphorylated flavonoid, such as a phosphorylated quercetin, phosphorylated fisetin, or phosphorylated 5,7-dideoxyquercetin sufficient to reduce a side effect of the opioid agent. Further description of types of pain, opioid agents and treatment of pain may be found in U.S. Patent Publication No. US2006/0111308 and PCT Publication No. WO/06055672, incorporated by reference herein in their entirety.

D. Wash-Out Methods

The invention further provides methods of reversing one or more side effects of a substance by administering a phosphorylated polyphenol e.g. phosphorylated pyrone analog such as a phosphorylated flavonoid, such as a phosphorylated quercetin, phosphorylated fisetin, or phosphorylated 5,7-dideoxyquercetin to an animal that has received an amount of the substance sufficient to produce one or more side effects. The methods are especially useful in a situation where it is desired to rapidly reverse one or more side effects of a substance, e.g., in an overdose situation or to enhance recovery from general anesthesia. Any suitable phosphorylated polyphenol e.g. phosphorylated pyrone analog such as a phosphorylated flavonoid, such as a phosphorylated quercetin, phosphorylated fisetin, or phosphorylated 5,7-dideoxyquercetin described herein may be used.

In some embodiments, the invention provides a method for reversing a side effect of an agent in a human by administering to the human an amount of a phosphorylated polyphenol e.g. phosphorylated pyrone analog such as a phosphorylated flavonoid, such as a phosphorylated quercetin, phosphorylated fisetin, or phosphorylated 5,7-dideoxyquercetin sufficient to partially or completely reverse a central nervous system effect of the agent, where the human has received an amount of said agent sufficient to produce a central nervous system effect. In some embodiments, the agent is a general anesthetic. Examples of general anesthetics include, but not limited to, desflurane, dexmedetomidine, diazepam, droperidol, enflurane, etomidate, halothane, isoflurane, ketamine, lorazepam, methohexital, methoxyflurane, midazolam, nitrous oxide propofol, sevoflurane, and thiopental. In some embodiments, the human has received an overdose of the agent producing the side effect. In some embodiments, the individual continues to experience peripheral effects of the agent. In some embodiments, the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is a side effect modulator, e.g. BTB transport protein modulator. In some embodiments, the phosphorylated pyrone analog such as a phosphorylated flavonoid is phosphorylated quercetin, phosphorylated isoquercetin, phosphorylated flavon, phosphorylated chrysin, phosphorylated apigenin, phosphorylated rhoifolin, phosphorylated diosmin, phosphorylated galangin, phosphorylated fisetin, phosphorylated morin, phosphorylated rutin, phosphorylated kaempferol, phosphorylated myricetin, phosphorylated taxifolin, phosphorylated naringenin, phosphorylated naringin, phosphorylated hesperetin, phosphorylated hesperidin, phosphorylated chalcone, phosphorylated phloretin, phosphorylated phlorizdin, phosphorylated genistein, phosphorylated 5,7-dideoxyquercetin, phosphorylated biochanin A, phosphorylated catechin, or phosphorylated epicatechin. In some embodiments, the phosphorylated pyrone analog such as a phosphorylated flavonoid is phosphorylated quercetin. In some embodiments, the phosphorylated pyrone analog such as a phosphorylated flavonoid is phosphorylated fisetin. In some embodiments, the phosphorylated pyrone analog such as a phosphorylated flavonoid is phosphorylated 5,7-dideoxyquercetin. In some embodiments, the phosphorylated pyrone analog such as a phosphorylated flavonoid is quercetin-3'-O-phosphate. Typically, the phosphorylated pyrone analog such as a phosphorylated flavonoid, such as a phosphorylated quercetin will be administered by injection, e.g., intravenously or intraperitoneally, in a dose sufficient to partially or completely reverse a side effect of the substance. Such a dose in a human can be, e.g., about 0.1-100 gm, or about 0.5-50 gm, or about 1-20 gm, or 1, 2, 3, 4, 5, 6, 7, 8, 9, 10, 12, 14, 16, 18, or 20 gm. In general, the dose can be 0.01-1.5 gm/kg.

E. Administration

The methods of the invention involve the administration of a phosphorylated polyphenol e.g. phosphorylated pyrone analog such as a phosphorylated flavonoid, such as a phosphorylated quercetin, phosphorylated fisetin, or phosphorylated 5,7-dideoxyquercetin. In some embodiments, a therapeutic agent that produces a side effect is administered in combination with a phosphorylated polyphenol e.g. phosphorylated pyrone analog such as a phosphorylated flavonoid, such as a phosphorylated quercetin, phosphorylated fisetin, or phosphorylated 5,7-dideoxyquercetin that reduces a side effect of the therapeutic agent. In some embodiments, other agents are also administered, e.g., other therapeutic agents. When two or more agents are co-administered, they may be co-administered in any suitable manner, e.g., as separate compositions, in the same composition, by the same or by different routes of administration.

In some embodiments, the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is administered in a single dose. This may be the case, e.g., in wash-out methods where the agent is introduced into an animal to quickly, for example to lower the side effect of a substance already present in the body. Typically, such administration will be by injection, e.g., intravenous injection, in order to introduce the agent quickly. However, other routes may be used as appropriate. A single dose of a phosphorylated polyphenol e.g. phosphorylated pyrone analog such as a phosphorylated flavonoid, such as a phosphorylated quercetin, phosphorylated fisetin, or phosphorylated 5,7-dideoxyquercetin may also be used when it is administered with the substance (e.g., a therapeutic agent that produces a side effect) for treatment of an acute condition.

In some embodiments, the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is administered in multiple doses. Dosing may be about once, twice, three times, four times, five times, six times, or more than six times per day. Dosing may be about once a month, once every two weeks, once a week, or once every other day. In one embodiment the drug is an immunosuppressive. In another embodiment the immunosuppressive compound and the transport protein activator are administered together about once per day to about 6 times per day. In another embodiment the administration of the immunosuppressive compound and the transport protein activator continues for less than about 7 days. In yet another embodiment the administration continues for more than about 6, 10, 14, 28 days, two months, six months, or one year. In some cases, continuous dosing is achieved and maintained as long as necessary, e.g., intravenous administration of immunosuppressive in a post-operative situation.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic pain.

An effective amount of a phosphorylated polyphenol and an effective amount of a drug may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The phosphorylated polyphenol e.g. phosphorylated pyrone analog such as a phosphorylated flavonoid, such as a phosphorylated quercetin, phosphorylated fisetin, or phosphorylated 5,7-dideoxyquercetin and the therapeutic agent may be administered in dosages as described herein (see, e.g., Compositions). Dosing ranges for therapeutic agents are known in the art. Dosing for the phosphorylated polyphenol e.g. phosphorylated pyrone analog such as a phosphorylated flavonoid, such as a phosphorylated quercetin, phosphorylated fisetin, or phosphorylated 5,7-dideoxyquercetin may be found by routine experimentation. For a phosphorylated pyrone analog such as a phosphorylated flavonoid, e.g., phosphorylated quercetin, phosphorylated fisetin, or phosphorylated 5,7-dideoxyquercetin, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of quercetin is about 100, 200, 300, 400, 500, 600, 700, 800, 900, or 1000 mg. In some embodiments, the daily dose of quercetin is 100 mg. In some embodiments, the daily dose of quercetin is 500 mg. In some embodiments, the daily dose of quercetin is 1000 mg. Daily dose range may depend on the form of phosphorylated pyrone analog such as a phosphorylated flavonoid, e.g., the carbohydrate moieties attached to the phosphorylated pyrone analog such as a phosphorylated flavonoid, and/or factors with which the phosphorylated pyrone analog such as a phosphorylated flavonoid is administered, as described herein.

In some embodiments, the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is administered two to three times a day with an oral dose of about 500 mg or an intravenous dose of about 150 mg. In some embodiments the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is administered about one hour or about 30 minutes prior to administration of the therapeutic agent. In some embodiments the phosphorylated polyphenol e.g. phosphorylated pyrone analog such as a phosphorylated flavonoid, such as a phosphorylated quercetin, phosphorylated fisetin, or phosphorylated 5,7-dideoxyquercetin is administered such that it is in the bloodstream 30 minutes prior to administration of the therapeutic agent. This timing may be accomplished by administering the phosphorylated polyphenol and the therapeutic agent separately, or by administering the quercetin and agent in the same composition that is formulated such that quercetin reaches the bloodstream before the therapeutic agent.

The serum half-life for, e.g., quercetin aglycone, is known to be about 19-25 hours. Where a phosphorylated polyphenol of the invention has a serum half life in the same range, single dose accuracy is not crucial.

When a phosphorylated polyphenol e.g. phosphorylated pyrone analog such as a phosphorylated flavonoid such as phosphorylated quercetin, phosphorylated fisetin, or phosphorylated 5,7-dideoxyquercetin, is administered as a BTB transport modulator in a composition that comprises one or more therapeutic agents, and the therapeutic agent has a shorter half-life than BTB transport modulator, unit dose forms of the therapeutic agent and the BTB transport modulator may be adjusted accordingly. Thus, for example, if phosphorylated phenol with a serum half life similar to that of quercetin is given in a composition also containing, e.g., tramadol, a typical unit dose form is, e.g., 50 mg tramadol/100 mg phosphorylated phenol, or 50 mg tramadol/500 mg phosphorylated phenol. See e.g., Compositions.

Table 3 below, provides exemplary dosing schemes for selected immunosuppressive agents and quercetin phosphate. These dosages are provided by way of example only and do not limit the invention.

| Therapeutic Agent (A) + Phosphorylated Quercetin (QP) | Per Dose (A:QP)* | | Per Day(A:QP) | |
|---|---|---|---|---|
| | ~mole:mole | ~mg:mg | ~mole:mole | ~mg:mg |
| Tacrolimus | 0.006:1 | 10:1000 | 0.01:1 | 30:2000 |
| Sirolimus | 0.1:1 | 100:1000 | 0.2:1-0.3:1 | 400-600:2000 |
| Cyclosporin | 0.07:1 | 80:1000 | 0.1:1 | 240:2000 |
| Mycophenolate | 0.04:1 | 40:1000 | 0.2:1 | 400:2000 |
| Prednisone | 0.6:1 | 300:1000 | 0.8:1 | 900:2000 |
| | 1.75:1 | 900:1000 | 2.6:1 | 2700:2000 |

*2000 mg phosphorylated quercetin daily, given in two divided doses, e.g., with two doses of the immunosuppressive. Some doses of immunosuppressive are given without phosphorylated quercetin.

EXAMPLES

Example 1

Method of synthesis of Phosphorylated Quercetin (Cyclic and Ring-Opened)

2-hydroxy-4-(3,5,7-trihydroxy-4-oxo-4H-chromen-2-yl) phenyl dihydrogen phosphate. A suspension of quercetin (1 g, 3.31 mmol) and triethylamine (2.3 mL, 16.5 mmol) in dichloromethane (100 mL) at room temperature is treated dropwise with a 10% solution of phosphorus oxychloride in dichloromethane (3.6 mL, 3.97 mmol). The resulting mixture is stirred overnight to afford a heterogeneous mixture along will a brown sticky precipitate. The LCMS of the solution showed clean conversion to a single species with the correct mass for the cyclic phosphate. The solution is separated and the solvent is removed in vacuo to give a yellow solid (presumably the TEA salt of cyclic phosphate). Some of the solid is taken and dissolved in water and a few drops of acetonitrile. Allowing this solution to sit overnight results in the hydrolytic ring opening of the cyclic phosphate to give acyclic phosphate as a yellow solid.

Example 2

Method of Synthesis of Quercetin-3'-O-phosphate

Quercetin dihydrate (30 g. 0.089 mol, 1 eq.) is added to dichloromethane (3 L) followed by triethylamine (69 mL, 0.49 mol, 5.5 eq.) in one portion. The mixture is stirred for 15 min, then phosphorus oxychloride (9.95 mL, 0.107 mol, 1.2 eq.) is added in one portion (mild exotherm). The mixture is heated to reflux for 15 min, the heat is removed and the mixture is stirred for 18 h at room temperature. The solution is decanted away from the gummy, black residue and is concentrated under vacuum.

The resultant solid from concentration of the decantate is added acetonitrile (500 mL) followed by water (50 mL) then 1N hydrochloric acid (approx. 20 mL) until a pH of about 5 is achieved. The solution is concentrated to a volume of about 120 mL. The residue is purified with a 600 g, C-18 reverse phase column with 60 mL injections in a gradient. The gradient is 100% water (1 L), 9:1 water:MeOH (1 L), 8:2 water: MeOH (1 L), 7:3 water:MeOH (1 L), 1:1 water:MeOH. The desired product begins to elute after about 500 mL of 1:1 water:MeOH. The fractions are combined and concentrated. The residue is dissolved in water (40 mL) and solid potassium carbonate (approx. 3 g) is added until pH=8. The pH is adjusted to about 2 with 50% sulfuric acid resulting in the formation of a precipitate. The solid is collected, which contained approximately 10% TEA. The solid is suspended in water (50 mL), and the pH is adjusted to about 8 with solid potassium carbonate to produce a yellow solution. The resultant yellow solution is treated dropwise with 50% sulfuric acid until a pH of about 2 is reached, resulting in the precipitation of a solid. The solid is collected and slurried in water (75 mL). The solid is collected and dried giving 4 g, representing 12% of quercetin-3'-O-phosphate. As described above, the quercetin-3'-O-phosphate is soluble at about 4 g in 50 mL of water at about pH 8, representing a solubility of 80 mg per mL. The identity of the compound is confirmed using $^1$H NMR, $^{31}$P NMR, and Mass Spectrometry, which gave an m/Z peak at (M+H)$^+$ of 383.1.

Example 3

Stability of Quercetin-3'-O-phosphate in Water

Quercetin-3'-O-phosphate is dissolved in water at about pH 8. After 24 hours in water at pH 8, no degradation is seen by NMR after 24 hours at ambient temperature.

Example 4

Blood Glucose Levels in Rats Co-Administered with Quercetin-3'-O-phosphate and Tacrolimus One set of 5 rats is treated from day 1 to day 25 with inert vehicle 2 intraperitoneally and treated from day 11 to day 25 with inert vehicle 1 intraperitoneally. A second set of 5 rats is treated from day 1 to day 25 with tacrolimus (Prograf®) at 0.5 mg/kg, and treated from day 11 to day 25 with inert vehicle 2. A third set 5 of rats is treated from day 1 to day 25 with tacrolimus (Prograf®) intraperitoneally at 0.5 mg/kg, and treated from day 11 to day 25 intraperitoneally with quercetin-3'-O-phosphate (Q-Phosphate) at 114 mg/kg. The blood glucose level in the rats is measured on days 1, 10, 15, 20, and 25. The results are shown in Tables 4-6 below and in FIG. 1. The results show that phosphorylated pyrone analogs such as Q-phosphate can attenuate tacrolimus induced hyperglycemia.

TABLE 4

Blood glucose levels in rats administered vehicle 1 and vehicle 2

| Treatment (mg/kg) i.p. once daily from Day 11 to Day 25 | Treatment (mg/kg) i.p. once daily from Day 1 to Day 25 | Rat number | Blood glucose (g/l) | | | | |
|---|---|---|---|---|---|---|---|
| | | | Day 1 | Day 10 | Day 15 | Day 20 | Day 25 |
| Vehicle 1 | Vehicle 2 | 1 | 1.26 | 1.32 | 1.21 | 1.01 | 1.21 |
| | | 2 | 1.43 | 1.27 | 1.30 | 0.93 | 1.13 |
| | | 3 | 1.20 | 0.95 | 1.26 | 1.27 | 1.16 |
| | | 4 | 1.51 | 1.36 | 1.30 | 1.12 | 1.08 |
| | | 5 | 1.44 | 1.39 | 1.30 | 1.26 | 1.27 |
| | Mean | | 1.37 | 1.26 | 1.27 | 1.12 | 1.17 |
| | ±s.e.m. | | 0.06 | 0.08 | 0.02 | 0.07 | 0.03 |
| | Mean change from Day 1 | | | −0.11 | −0.10 | −0.25 | −0.20 |

TABLE 5

Blood glucose levels in rats administered vehicle 1 and tacrolimus

| Treatment (mg/kg) i.p. once daily from Day 11 to Day 25 | Treatment (mg/kg) i.p. once daily from Day 1 to Day 25 | Rat number | Blood glucose (g/l) | | | | |
|---|---|---|---|---|---|---|---|
| | | | Day 1 | Day 10 | Day 15 | Day 20 | Day 25 |
| Vehicle 1 | Prograf ® 0.5 | 6 | 1.16 | 1.40 | 2.31 | 2.97 | 1.69 |
| | | 7 | 1.22 | 1.09 | 1.97 | 2.41 | 2.98 |
| | | 8 | 1.47 | 2.25 | 3.02 | 2.77 | 3.96 |
| | | 9 | 1.16 | 1.30 | 3.72 | 2.79 | 0.97 |
| | | 10 | 1.34 | 1.39 | 1.67 | 3.70 | 3.16 |
| | Mean | | 1.27 | 1.49 | 2.54 | 2.93 | 2.55 |
| | ±s.e.m. | | 0.06 | 0.20 | 0.37 | 0.21 | 0.54 |
| | Mean change from Day 1 | | | +0.22 | +1.27 | +1.66 | +1.28 |
| | Mean change from all vehicle control | | −0.10 | +0.23 | +1.27 | +1.81 | +1.38 |

TABLE 6

Blood glucose levels in rats administered Q-Phosphate and tacrolimus

| Treatment (mg/kg) i.p. once daily from Day 11 to Day 25 | Treatment (mg/kg) i.p. once daily from Day 1 to Day 25 | Rat number | Blood glucose (g/l) | | | | |
|---|---|---|---|---|---|---|---|
| | | | Day 1 | Day 10 | Day 15 | Day 20 | Day 25 |
| Q-Phosphate 114 | Prograf ® 0.5 | 11 | 1.41 | 2.19 | 3.16 | 3.67 | 2.04 |
| | | 12 | 1.36 | 1.51 | 1.83 | 3.58 | 2.67 |
| | | 13 | 1.30 | 2.10 | 1.42 | 1.67 | 1.23 |
| | | 14 | 1.18 | 1.50 | 2.07 | 1.99 | 2.34 |
| | | 15 | 1.19 | 2.41 | 2.90 | 3.28 | 2.54 |
| | Mean | | 1.29 | 1.94 | 2.28 | 2.84 | 2.16 |
| | ±s.e.m. | | 0.05 | 0.19 | 0.33 | 0.42 | 0.26 |
| | Mean change from Day 1 | | | +0.65 | +0.99 | +1.55 | +0.87 |
| | Mean change from Prograf ® control | | +0.02 | +0.45 | −0.26 | −0.09 | −0.39 |

Example 5

Figure 2:
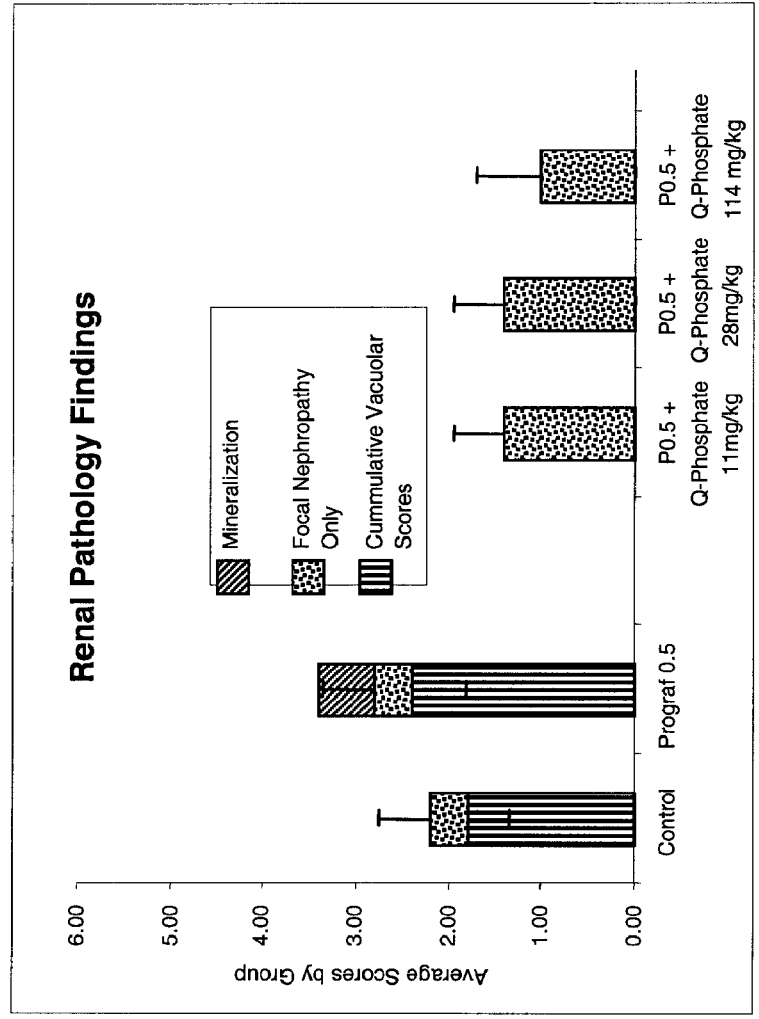
FIG. 2 is a graph of renal pathology scores for kidney tissue from rats showing protection of tacrolimus induced kidney damage by phosphorylated quercetin.

Renal Pathology in Rats Co-Administered with Quercetin-3'-O-phosphate and Tacrolimus Tissue is removed from the kidney of rats treated with tacrolimus (Prograf®) at 0.5 mg/kg and inert vehicle, and from rats treated with tacrolimus (Prograf®) at 0.5 mg/kg and quercetin-3'-O-phosphate (Q-Phosphate) at 11 mg/kg, 28 mg/kg, and at 114 mg/kg for 25 days. The tissue from rats treated with tacrolimus and vehicle show significant vacuolation. The tissue from rats treated with Q-Phosphate and tacrolimus show no vacuoles. FIG. 2 shows renal pathology scores for the tissues. These results indicate that Q-phosphate is exerting a significant protective effect with respect to the kidneys when co-administered with tacrolimus.

Example 6

In-Vitro Toxicity Screening of Quercetin-3'-O-phosphate

A secondary pharmacological screening of molecules of interest at a fixed concentration is often practiced in the pharmaceutical industry in order to evaluate the effect of the compound on secondary targets that could result in untoward toxicity in-vivo. These secondary screens are well known in the art and can be carried out by labs which specialize in these tests such as MDS-Panlabs and CEREP. A secondary toxicity screen is performed with Quercetin-3'-O-phosphate at a concentration of 10 µM against 122 targets in enzyme, radioligand binding, and cellular assays by MDS Pharma Services by methods well known in the art. Inhibition is found in only the following targets (percent inhibition at 10 µM in parentheses): ATPase, Na+/K+, Heart, Pig (65%), Nitric Oxide Synthase, Endothelial (eNOS) (72%), Protein Tyrosine Kinase, FGFR2 (94%), Protein Tyrosine Kinase, FGFR1 (96%), Protein Tyrosine Kinase, Insulin Receptor (91%), Protein Tyrosine Kinase, (82%), Protein Tyrosine Kinase, ZA70 (ZAP-70) (74%), UDP Glucuronosyltransferase, UGT1A1 (52%), Adenosine $A_1$ (50%), Adrenergic $\alpha_{2A}$ (57%), Dopamine $D_{47}$ (51%), Peripheral Benzodiazepine Receptor (PBR) (53%), Transporter, Monoamine rabbit (68%), Serotonin (5-Hydroxytryptamine) 5-$HT_{1A}$ (62%).

The compound is additionally tested in Adenosine$_{A1}$, Adrenergic$_{A2A}$, DopamineD$_{25}$, Histamine $H_1$-, and μ-Opiate GTPγS functional assays using a concentration of 10 μM. The compound demonstrated 48% antagonist activity in the Adenosine$_{A1}$ assay, and marked negative inhibition in the Adrenergic$_{A2A}$ assay, potentially indicating PAF-5 could be acting as an inverse agonist in this assay.

The findings of this toxicology screen indicate that Quercetin-3'-O-phosphate has low toxicity properties, especially in light of the fact that the concentration tested, 10 μM, is high as compared to a therapeutic dose (e.g. greater than ~100 times).

Example 7

Preparation of Quercetin-3'-O-phosphate (Alternative Method)

Quercetin dihydrate (90 g. 266 mmol, 1.0 eq.) is added to dimethylformamide (900 mL), followed by triethylamine (210 mL, 1463 mmol, 5.5 eq.) in one portion. The mixture is cooled to about −1° C. by acetone/dry ice bath while stirring. Phosphorus oxychloride (30 mL, 319 mmol, 1.2 eq.) is slowly added via an addition funnel keeping the internal temperature below about 5° C. The mixture is carefully kept between −1° C. and 5° C. until the addition of phosphorus oxychloride completed. The acetone/dry ice bath is then removed and replace by an ice/water bath. The mixture is slowly warmed to room temperature over 18 h. To the solution is added 10% HCl (approx. 140 mL) until pH=5. The solution is concentrated and the solid is dissolved in water (approx. 160 mL).

The solution is purified over a 600 g, C-18 reverse phase column with 60 mL per injection. After each injection, the column is eluted with the following gradient. (i) 100% deionized water (3 L), (ii) 10% MeOH in water (1 L), (iii) 20% MeOH in water (1 L), (iv) 30% MeOH in water (1 L), and (v) 1:1 water:MeOH (1 L). The desired product lutes in the 1 L fraction of 1:1 water:MeOH. This fraction is concentrated in vacuo.

The fractions containing the desired product are concentrated to approximately 1.5 L volume, solid sodium carbonate is added slowly until reaching pH 9 and the solution is stirred at room temperature for 15 min. The solution is cooled to 3° C. and 50% sulfuric acid added slowly until attaining pH 2. The solution is kept in the cold bath for 1 h and fine yellow solid precipitates.

The mixture is aliquoted into centrifuge bottles with 220 g in each bottle. The mixture is centrifuged and the supernatant is decanted. The yellow solids are suspended in 1 N HCl (200 mL) and centrifuged, the supernatant is decanted. The yellow solid is suspended in deionized water (200 mL), centrifuged and the supernatant decanted. The resultant solid is resuspended into deionized water, centrifuged and the supernatant decanted. The wet solid is frozen and lyophilized.

The crude dried material is suspended in anhydrous methanol and collected to afford the desired product. The filtrate contains other isomeric O-phosphates All of the methods disclosed and claimed herein can be made and executed without undue experimentation in light of the present disclosure. It will be apparent to those of skill in the art that variations may be applied without departing from the concept, spirit and scope of the invention. More specifically, it will be apparent that certain agents that both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. Quercetin-3'-O-phosphate as a pharmaceutically acceptable salt at a purity of greater than 90%.

2. The quercetin-3'-O-phosphate salt of claim 1 at a purity of greater than 95%.

3. The quercetin-3'-O-phosphate salt of claim 1 at a purity of greater than 98%.

4. The quercetin-3'-O-phosphate salt of claim 1 at a purity of greater than 99%.

5. The quercetin-3'-O-phosphate salt of claim 1 at a purity of greater than 99.8%.

6. A composition in discrete dosage form, comprising quercetin-3'-O-phosphate as a pharmaceutically acceptable salt at a purity of greater than 90%, and at least one pharmaceutically acceptable excipient.

7. The composition of claim 6, wherein the quercetin-3'-O-phosphate salt is at a purity of greater than 95%.

8. The composition of claim 6, wherein the quercetin-3'-O-phosphate salt is at a purity of greater than 98%.

9. The composition of claim 6, wherein the quercetin-3'-O-phosphate salt is at a purity of greater than 99%.

10. The composition of claim 6, wherein the quercetin-3'-O-phosphate salt is at a purity of greater than 99.8%.

11. The composition of claim 6, wherein the composition is formulated for oral administration.

12. The composition of claim 11, wherein the composition is in the form of a tablet or capsule.

13. The composition of claim 6, further comprising a therapeutic agent.

14. The composition of claim 13, wherein the therapeutic agent is an immunosuppressant, antiviral, antibiotic, antineoplastic, amphetamine, antihypertensive, vasodilator, barbiturate, membrane stabilizer, cardiac stabilizer, glucocorticoid, antilipedemic, antiglycemic, cannabinoid, antidepressant, antineuroleptic, antiinfective, immunomodulator or chemotherapeutic agent.

15. The composition of claim 13, wherein the therapeutic agent is an immunosuppressant.

16. The composition of claim 13, wherein the therapeutic agent is a calcineurin inhibitor.

17. The composition of claim 13, wherein the therapeutic agent is tacrolimus, sirolimus, mycophenolate, methadone, cyclosporin, prednisone, voclosporin, oxycodone, gabapentin, pregabalin, hydrocodone, fentanyl, hydromorphone, levorphenol, morphine, methadone, mycophenolate, tramadol, hydromorphine, topiramate, diacetyl morphine, codeine, olanzapine, hydrocortisone, prednisone, sufentanyl, alfentanyl, carbamazepine, lamotrigine, doxepin, or haloperidol.

18. The composition of claim 13, wherein the therapeutic agent is tacrolimus, sirolimus, mycophenolate, methadone, cyclosporin, prednisone, or voclosporin.

19. The composition of claim 13, wherein the therapeutic agent is tacrolimus.

20. The composition of claim 13, wherein the therapeutic agent is cyclosporin.

21. A kit comprising:
(a) quercetin-3'-O-phosphate as a pharmaceutically acceptable salt at a purity of greater than 90%;
(b) a therapeutic agent; and
(c) instructions for use of the quercetin-3'-O-phosphate salt, the therapeutic agent, or both.

22. The kit of claim 21, wherein the quercetin-3'-O-phosphate salt is at a purity of greater than 95%.

23. The kit of claim 21, wherein the quercetin-3'-O-phosphate salt is at a purity of greater than 98%.

24. The kit of claim 21, wherein the quercetin-3'-O-phosphate salt is at a purity of greater than 99%.

25. The kit of claim 21, wherein the quercetin-3'-O-phosphate salt is at a purity of greater than 99.8%.

26. The kit of claim 21, wherein the therapeutic agent is an immunosuppressant, antiviral, antibiotic, antineoplastic, amphetamine, antihypertensive, mvasodilator, barbiturate, membrane stabilizer, cardiac stabilizer, glucocorticoid, antilipedemic, antiglycemic, cannabinoid, antidepressant, antineuroleptic, antiinfective, immunomodulator or chemotherapeutic agent.

27. The kit of claim 21, wherein the therapeutic agent is an immunosuppressant.

28. The kit of claim 21, wherein the therapeutic agent is a calcineurin inhibitor.

29. The kit of claim 21, wherein the therapeutic agent is tacrolimus, sirolimus, mycophenolate, methadone, cyclosporin, prednisone, voclosporin, oxycodone, gabapentin, pregabalin, hydrocodone, fentanyl, hydromorphone, levorphenol, morphine, methadone, mycophenolate, tramadol, hydromorphine, topiramate, diacetyl morphine, codeine, olanzapine, hydrocortisone, prednisone, sufentanyl, alfentanyl, carbamazepine, lamotrigine, doxepin, or haloperidol.

30. The kit of claim 21, wherein the therapeutic agent is tacrolimus, sirolimus, mycophenolate, methadone, cyclosporin, prednisone, or voclosporin.

31. The kit of claim 21, wherein the therapeutic agent is tacrolimus.

32. The kit of claim 21, wherein the therapeutic agent is cyclosporin.

33. The quercetin-3'-O-phosphate salt of any one of claims 1 through 5, wherein the quercetin-3'-O-phosphate salt is a sodium or a potassium phosphate salt.

34. The quercetin-3'-O-phosphate salt of claim 33, wherein the quercetin-3'-O-phosphate salt is a monosodium or a monopotassium phosphate salt.

35. The quercetin-3'-O-phosphate salt of claim 34, wherein the quercetin-3'-O-phosphate salt is the monosodium phosphate salt.

36. The quercetin-3'-O-phosphate salt of claim 34, wherein the quercetin-3'-O-phosphate salt is the monopotassium phosphate salt.

37. The composition of any one of claims 6 through 20, wherein the quercetin-3'-O-phosphate salt is a sodium or a potassium phosphate salt.

38. The composition of claim 37, wherein the quercetin-3'-O-phosphate salt is a monosodium or a monopotassium phosphate salt.

39. The composition of claim 38, wherein the quercetin-3'-O-phosphate salt is the monosodium phosphate salt.

40. The composition of claim 38, wherein the quercetin-3'-O-phosphate salt is the monopotassium phosphate salt.

41. The kit of any one of claims 21 through 32, wherein the quercetin-3'-O-phosphate salt is a sodium or a potassium phosphate salt.

42. The kit of claim 41, wherein the quercetin-3'-O-phosphate salt is a monosodium or a monopotassium phosphate salt.

43. The kit of claim 42, wherein the quercetin-3'-O-phosphate salt is the monosodium phosphate salt.

44. The kit of claim 42, wherein the quercetin-3'-O-phosphate salt is the monopotassium phosphate salt.

* * * * *

UNITED STATES PATENT AND TRADEMARK OFFICE
CERTIFICATE OF CORRECTION

PATENT NO. : 7,947,733 B2  Page 1 of 1
APPLICATION NO. : 12/182992
DATED : May 24, 2011
INVENTOR(S) : Wendye Robbins et al.

It is certified that error appears in the above-identified patent and that said Letters Patent is hereby corrected as shown below:

Title Page, Item (75):
"Wendye Robbins, San Francisco, CA (US); Ving Lee, Los Altos, CA (US)" should read,
--Wendye Robbins, South San Francisco, CA (US); Ving Lee, Los Altos, CA (US)--.

Title Page, Item (73):
"Limerick BioPharma, South San Francisco, CA (US)" should read, --Limerick BioPharma, Inc., South San Francisco, CA (US)--.

Signed and Sealed this
Fourth Day of December, 2012

David J. Kappos
*Director of the United States Patent and Trademark Office*